(12) United States Patent
Poltaretskyi et al.

(10) Patent No.: US 12,051,198 B2
(45) Date of Patent: Jul. 30, 2024

(54) PRE-MORBID CHARACTERIZATION OF ANATOMICAL OBJECT USING STATISTICAL SHAPE MODELING (SSM)

(71) Applicant: HOWMEDICA OSTEONICS CORP., Mahwah, NJ (US)

(72) Inventors: Sergii Poltaretskyi, Plougonvelin (FR); Jean Chaoui, Locmaria Plouzané (FR); Maximilien Mayya, Brest (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 346 days.

(21) Appl. No.: 17/435,978

(22) PCT Filed: Mar. 18, 2020

(86) PCT No.: PCT/US2020/023361
§ 371 (c)(1),
(2) Date: Sep. 2, 2021

(87) PCT Pub. No.: WO2020/205248
PCT Pub. Date: Oct. 8, 2020

(65) Prior Publication Data
US 2022/0156924 A1 May 19, 2022

Related U.S. Application Data

(60) Provisional application No. 62/826,362, filed on Mar. 29, 2019, provisional application No. 62/826,172, (Continued)

(51) Int. Cl.
*G06T 7/00* (2017.01)
*G06T 7/35* (2017.01)
*G06T 7/50* (2017.01)

(52) U.S. Cl.
CPC .............. *G06T 7/0012* (2013.01); *G06T 7/35* (2017.01); *G06T 7/50* (2017.01); *G06T 2207/20021* (2013.01); *G06T 2207/30008* (2013.01)

(58) Field of Classification Search
CPC ........... G06T 7/0012; G06T 7/35; G06T 7/50; G06T 2207/20021; G06T 2207/30008;
(Continued)

(56) References Cited

U.S. PATENT DOCUMENTS 7,542,791 B2  6/2009 Mire et al.
8,160,325 B2  4/2012 Zug et al.
(Continued)

FOREIGN PATENT DOCUMENTS

EP  2471483 A1  7/2012
EP  1858430 B1  10/2013
(Continued)

OTHER PUBLICATIONS

Yamazaki et al., "Estimation of Implant Position After Total Knee Arthroplasty Using 2D/3D Image Registration," Japanese Society of Medical Imaging and Technology convention proceedings (CD-ROM), vol. 30, 2011 (Applicant points out, in accordance with MPEP 609.04(a), that the year of publication, 2011, is sufficiently earlier than the effective U.S. filing date, so that the particular month of publication is not in issue.) 6 pp.
(Continued)

*Primary Examiner* — Qian Yang
(74) *Attorney, Agent, or Firm* — Shumaker & Sieffert, P.A.

(57) ABSTRACT

Techniques are described for determining a pre-morbid shape of an anatomical object. Processing circuitry may determine an aligned shape based on image data with under- or over-segmentation. The processing circuitry may utilize
(Continued)

the aligned shape and a shape model such as a mean shape model of the anatomical object to register the aligned shape to the shape model and generate information indicative of the pre-morbid shape of the anatomical object.

26 Claims, 18 Drawing Sheets

Related U.S. Application Data filed on Mar. 29, 2019, provisional application No. 62/826,410, filed on Mar. 29, 2019.

(58) Field of Classification Search
CPC .... G06T 2207/30052; A61B 2034/102; A61B 34/10; A61F 2/30942
See application file for complete search history.

(56) References Cited

U.S. PATENT DOCUMENTS

| | | | |
|---|---|---|---|
| 8,175,683 B2 | 5/2012 | Roose | |
| 8,214,016 B2 | 7/2012 | Lavallee et al. | |
| 8,231,634 B2 | 7/2012 | Mahfouz et al. | |
| 8,382,765 B2 | 2/2013 | Axelson et al. | |
| 8,532,807 B2 | 9/2013 | Metzger | |
| 8,617,174 B2 | 12/2013 | Axelson, Jr. et al. | |
| 8,634,618 B2 | 1/2014 | Zug et al. | |
| 8,764,836 B2 | 7/2014 | De Wilde et al. | |
| 8,830,233 B2 | 9/2014 | Friedland et al. | |
| 8,884,618 B2 | 11/2014 | Mahfouz | |
| 8,898,043 B2 | 11/2014 | Ashby et al. | |
| 8,903,530 B2 | 12/2014 | Metzger | |
| 8,971,606 B2 | 3/2015 | Chaoui et al. | |
| 8,990,052 B2 | 3/2015 | Lavallee et al. | |
| 9,095,375 B2 | 8/2015 | Haimerl et al. | |
| 9,301,812 B2 | 4/2016 | Kehres et al. | |
| 9,345,548 B2 | 5/2016 | Schoenefeld et al. | |
| 9,408,698 B2 | 8/2016 | Miles et al. | |
| 9,504,579 B2 | 11/2016 | Mahfouz et al. | |
| 9,649,170 B2 | 5/2017 | Park et al. | |
| 9,684,768 B2 | 6/2017 | Lavallee et al. | |
| 9,713,539 B2 | 7/2017 | Haimerl et al. | |
| 9,717,508 B2 | 8/2017 | Iannotti et al. | |
| 9,737,367 B2 | 8/2017 | Steines et al. | |
| 9,741,263 B2 | 8/2017 | Iannotti et al. | |
| 9,757,238 B2 | 9/2017 | Metzger | |
| 9,814,533 B2 | 11/2017 | Park et al. | |
| 9,836,891 B2 | 12/2017 | Hatanaka et al. | |
| 9,913,691 B2 | 3/2018 | Brooks | |
| 10,019,551 B2 | 7/2018 | Zellner et al. | |
| 10,102,309 B2 | 10/2018 | McKinnon et al. | |
| 10,130,378 B2 | 11/2018 | Bryan | |
| 10,159,513 B2 | 12/2018 | Pavlovskaia et al. | |
| 10,172,715 B2 | 1/2019 | De Wilde et al. | |
| 10,182,870 B2 | 1/2019 | Park et al. | |
| 10,262,084 B2 | 4/2019 | Lavallee et al. | |
| 10,537,390 B2 | 1/2020 | Varadarajan et al. | |
| 10,600,515 B2 | 3/2020 | Otto et al. | |
| 10,667,867 B2 | 6/2020 | Gangwar et al. | |
| 10,675,063 B2 | 6/2020 | Pavlovskaia et al. | |
| 10,722,310 B2 | 7/2020 | Luby | |
| 10,762,623 B2 | 9/2020 | Geebelen et al. | |
| 10,922,448 B2 | 2/2021 | McKinnon et al. | |
| 10,973,535 B2 | 4/2021 | Iannotti et al. | |
| 10,973,580 B2 | 4/2021 | Berend et al. | |
| 11,033,335 B2 | 6/2021 | Zhang | |
| 11,051,830 B2 | 7/2021 | Jaramaz et al. | |
| 11,071,592 B2 | 7/2021 | McGuan et al. | |
| 11,083,525 B2 | 8/2021 | Varadarajan et al. | |
| 11,166,764 B2 | 11/2021 | Roh et al. | |
| 11,253,323 B2 | 2/2022 | Hughes et al. | |
| 11,278,413 B1 | 3/2022 | Lang | |
| 11,298,188 B2 | 4/2022 | Kehres et al. | |
| 11,298,189 B2 | 4/2022 | Kelman et al. | |
| 11,337,762 B2 | 5/2022 | McKinnon et al. | |
| 11,344,370 B2 | 5/2022 | Park et al. | |
| 11,410,769 B1 | 8/2022 | Yildirim | |
| 11,419,680 B2 | 8/2022 | Knotaxis et al. | |
| 11,432,931 B2 | 9/2022 | Lang | |
| 11,443,846 B2 | 9/2022 | Schoenefeld et al. | |
| 11,488,721 B2 | 11/2022 | Otto et al. | |
| 11,490,965 B2 | 11/2022 | Bischoff et al. | |
| 11,490,966 B2 | 11/2022 | Roche et al. | |
| 11,596,479 B2 | 3/2023 | McGuan et al. | |
| 11,621,086 B2 | 4/2023 | Spanberg et al. | |
| 11,622,818 B2 | 4/2023 | Siemionow et al. | |
| 11,653,976 B2 | 5/2023 | Bonny et al. | |
| 11,660,197 B1 | 5/2023 | Lang | |
| 11,717,412 B2 | 8/2023 | Casey et al. | |
| 11,751,946 B2 | 9/2023 | Gangwar et al. | |
| 11,766,268 B2 | 9/2023 | Iannotti et al. | |
| 11,847,755 B2 | 12/2023 | Park et al. | |
| 2004/0066958 A1* | 4/2004 | Chen | A61B 6/466 |
| | | | 382/128 |
| 2009/0089034 A1 | 4/2009 | Penney et al. | |
| 2010/0256504 A1 | 10/2010 | Moreau-Gaudry et al. | |
| 2011/0176746 A1 | 7/2011 | Bucki | |
| 2014/0303938 A1 | 10/2014 | Schoenfeld et al. | |
| 2014/0303990 A1 | 10/2014 | Schoenefeld et al. | |
| 2016/0367264 A1 | 12/2016 | Geebelen | |
| 2017/0035513 A1 | 2/2017 | Mahfouz et al. | |
| 2017/0143494 A1 | 5/2017 | Mahfouz | |
| 2017/0252047 A1 | 9/2017 | Dalla Pria | |
| 2017/0367766 A1 | 12/2017 | Mahfouz | |
| 2018/0225823 A1* | 8/2018 | Zhou | G06T 7/11 |
| 2018/0325526 A1 | 11/2018 | Haddad | |
| 2019/0029757 A1 | 1/2019 | Roh et al. | |
| 2019/0090952 A1 | 3/2019 | Bonny et al. | |
| 2019/0142519 A1 | 5/2019 | Siemionow et al. | |
| 2019/0365473 A1 | 12/2019 | Kehres et al. | |
| 2020/0104614 A1 | 4/2020 | Rui | |
| 2020/0113632 A1 | 4/2020 | Varadarajan et al. | |
| 2020/0281728 A1 | 9/2020 | Kulper et al. | |
| 2021/0030477 A1 | 2/2021 | Zuhars et al. | |
| 2021/0128179 A1 | 5/2021 | Dupuis et al. | |
| 2021/0196290 A1 | 7/2021 | Iannotti et al. | |
| 2021/0307833 A1 | 10/2021 | Farley et al. | |
| 2021/0315642 A1 | 10/2021 | McGuan et al. | |
| 2021/0322130 A1 | 10/2021 | Penney et al. | |
| 2021/0330389 A1 | 10/2021 | Varadarajan et al. | |
| 2022/0054197 A1 | 2/2022 | Plessers et al. | |
| 2022/0110685 A1 | 4/2022 | McGuan et al. | |
| 2022/0125515 A1 | 4/2022 | McGuan et al. | |
| 2022/0148454 A1 | 5/2022 | Jaramaz et al. | |
| 2022/0183757 A1 | 6/2022 | Caldera et al. | |
| 2022/0202497 A1 | 6/2022 | Janna et al. | |
| 2022/0249168 A1 | 8/2022 | Besier et al. | |
| 2022/0257321 A1 | 8/2022 | Kehres et al. | |
| 2022/0273450 A1 | 9/2022 | Steines et al. | |
| 2022/0346968 A1 | 11/2022 | Pettersson et al. | |
| 2022/0351828 A1 | 11/2022 | Chaoui | |
| 2022/0370142 A1 | 11/2022 | Schoenefeld et al. | |
| 2022/0387110 A1 | 12/2022 | Chaoui | |
| 2023/0045575 A1 | 2/2023 | Lang et al. | |
| 2023/0085093 A1 | 3/2023 | Chaoui et al. | |
| 2023/0094903 A1 | 3/2023 | Harris, Jr. et al. | |
| 2023/0139531 A1 | 5/2023 | Roche et al. | |
| 2023/0181257 A1 | 6/2023 | McGuan et al. | |
| 2023/0248435 A1 | 8/2023 | Bonny et al. | |
| 2023/0317298 A1 | 10/2023 | Spanberg et al. | |
| 2023/0346397 A1 | 11/2023 | Iannotti et al. | |
| 2023/0372018 A1 | 11/2023 | Gangwar et al. | |

FOREIGN PATENT DOCUMENTS

| | | | |
|---|---|---|---|
| EP | 2770919 | B1 | 8/2017 |
| EP | 2303192 | B1 | 11/2018 |
| EP | 3481318 | B1 | 9/2022 |
| JP | 2006212294 | A | 8/2006 |
| JP | 2011041656 | A | 3/2011 |
| JP | 2011517579 | A | 6/2011 |
| JP | 2012518519 | A | 8/2012 |
| JP | 2016178986 | A | 10/2016 |

(56) References Cited

FOREIGN PATENT DOCUMENTS

| | | |
|---|---|---|
| JP | 2017521164 A | 8/2017 |
| WO | 2009106816 A1 | 9/2009 |
| WO | 2014016895 A1 | 1/2014 |
| WO | 2016007936 A2 | 1/2016 |
| WO | 2022169678 A1 | 8/2022 |
| WO | 2023200562 A1 | 10/2023 |

OTHER PUBLICATIONS

Notice of Intent to Grant from counterpart Japanese Application No. 2021-558618 dated Jun. 6, 2023, 5 pp.

Written Opinion and Amendment, and translation thereof, from counterpart Japanese Application No. 2021-558618, filed Feb. 14, 2023, 22 pp.

"Blueprint 3d Planning Software + PSI," Wright Medical Group, retrieved from https://www.wright.com/blueprint-3d-planning-psi-system on Oct. 15, 2020, 9 pp.

"Chapter 4—Statistical Shape Models," dated Aug. 22, 2006, 17 pp, retrieved from http://www.cmlab.csie.ntu.edu.tw/~cyy/learning/papers/PCA_ASM.pdf.

"HoloLens 2," Microsoft Hololens, retrieved from https://www.microsoft.com/en-us/hololens, on Oct. 15, 2020, 5 pp.

Abler et al., "A statistical shape model to predict the premorbid glenoid cavity," Journal of Shoulder and Elbow Surgery, vol. 27, No. 10, Jun. 2018, 9 pp.

Abler et al., "A statistical shape model to predict the premorbid glenoid cavity: Supplementary Material," Oct. 2018. Retrieved from internet URL:https://ars.els-cdn.com/content/image/1-s2.0-S1058274618303082-mmc1.doxc; retrieved on May 8, 2020, 8 pp.

Boissonnat, J.D., "Shape Reconstruction from Planar Cross Sections," Computer Vision, Graphics, and Image Processing, vol. 44, No. 1, Oct. 1988, 29 pp.

Horn, B. K.P., "Closed-form solution of absolute orientation using unit quaternions," Journal of the Optical Society of America A, vol. 4, No. 4, Apr. 1987, 14 pp.

International Preliminary Report on Patentability from International Application No. PCT/US2020/023361, mailed Oct. 14, 2021, 8 pp.

International Search Report and Written Opinion of International Application No. PCT/US2020/023361, mailed May 19, 2020, 15 pp.

Marker et al., "Contour-Based Surface Reconstruction using Implicit Curve Fitting, and Distance Field Filtering and Interpolation," Volume Graphics, Jan. 2006, 9 pp.

Nguyen et al., "A new segmentation method for MRI images of the shoulder joint," Fourth Canadian Conference on Computer and Robot Vision (CRV'07), May 2007, 8 pp.

Plessers et al., "Virtual reconstruction of glenoid bone defects using a statistical shape model," Journal of Shoulder and Elbow Surgery, vol. 27, No. 1, Jan. 2018, 7 pp.

Poltaretskyi et al., "Prediction of the pre-morbid 3D anatomy of the proximal humerus based on statistical shape modelling," The Bone & Joint Journal, vol. 99-B, No. 7, Jul. 2017, 7 pp.

Sugio, T., "On dependency issue of predicting transform in TMC13," International Organisation for Standardisation, ISO/IEC JTC1/SC29/WG11 MPEG2019/m49630; Jul. 2019, 5 pp.

U.S. Appl. No. 17/435,998, filed Mar. 18, 2020, naming inventors Poltaretskyi et al.

U.S. Appl. No. 17/436,001, filed Mar. 18, 2020, naming inventors Poltaretskyi et al.

Vanden Bergeh et al., "Virtual anatomical reconstruction of large acetabular bone defects using a statistical shape model," Computer Methods in Biomechanics and Biomedical Engineering, vol. 20, No. 6, May 2017, 10 pp.

Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.

Wright, "BluePrint, 3d Planning + PSI," User Manual V2.1, Torier, CAW-8754, Nov. 2017, 18 pp.

Response to Communication Pursuant to Rules 161(1) and 162 EPC dated Nov. 8, 2021, from counterpart European Application No. 20717537.3, filed Apr. 26, 2022, 22 pp.

Office Action from counterpart Japanese Application No. 2021-558618 dated Nov. 22, 2022, 3 pp.

Cootes et al., "Active Shape Models—Their Training and Application," Computer Vision and Image Understanding, vol. 61, No. 1, Jan. 1995, pp. 38-59.

Cootes et al., "Statistical Models of Appearance for Computer Vision," University of Manchester, Mar. 8, 2004, 125 pp.

Stegmann et al., "A Brief Introduction to Statistical Shape Analysis," Informatics and Mathematical Modelling, Technical University of Denmark, Mar. 6, 2002, 15 pp.

\* cited by examiner

PRE-MORBID CHARACTERIZATION OF ANATOMICAL OBJECT USING STATISTICAL SHAPE MODELING (SSM)

This application is a national stage application under 35 U.S.C. § 371 of PCT Application No. PCT/US2020/023361, filed Mar. 18, 2020, which claims the benefit of U.S. Provisional Application No. 62/826,172 filed Mar. 29, 2019, U.S. Provisional Application No. 62/826,362 filed Mar. 29, 2019, and U.S. Provisional Application No. 62/826,410 filed Mar. 29, 2019. The entire contents of each of PCT Application No. PCT/US2020/023361, U.S. Provisional Application Nos. 62/826,172, U.S. Provisional Application No. 62/826,362, and U.S. Provisional Application No. 62/826,410 are incorporated herein by reference in their entirety.

BACKGROUND

Surgical joint repair procedures involve repair and/or replacement of a damaged or diseased joint. A surgical joint repair procedure, such as joint arthroplasty as an example, may involve replacing the damaged joint with a prosthetic that is implanted into the patient's bone. Proper selection or design of a prosthetic that is appropriately sized and shaped and proper positioning of that prosthetic are important to ensure an optimal surgical outcome. A surgeon may analyze damaged bone to assist with prosthetic selection, design and/or positioning, as well as surgical steps to prepare bone or tissue to receive or interact with a prosthetic.

SUMMARY

This disclosure describes example techniques to perform pre-morbid characterization of patient anatomy, such as one or more anatomical objects. Pre-morbid characterization refers to determining a predictor model that predicts characteristics (e.g., size, shape, location) of patient anatomy as the anatomy existed prior to damage to the patient anatomy or disease progression of the anatomy. In examples described in this disclosure, the predictor model may be a graphical shape model, such as a 3D volume, that a surgeon can view to assist in planning of an orthopaedical surgical procedure, e.g., to repair or replace an orthopedic joint, as one example.

In some examples, generating the pre-morbid characterization relies on imaging of the anatomical objects after the damage or disease progression. However, the damage or disease progression causes loss of portions of the anatomical objects that would be desirable to have for generating the pre-morbid characterization. Moreover, over-segmentation or under-segmentation, as described below, from imaging of the anatomical objects also causes loss of imaging data that is useable to perform the pre-morbid characterization.

This disclosure describes example techniques to determine a representation of a pre-morbid anatomical object (e.g., a predictor of the pre-morbid anatomical object) using statistical shape modeling (SSM), and particularly, determining a shape model representative of the patient pre-morbid anatomical object based on current patient anatomy, in accordance with a cost function.

In one example, the disclosure describes a method for determining a pre-morbid shape of an anatomical object of an orthopedic joint of a patient, the method comprising determining respective medialization values for each of a plurality of estimated shape models, wherein the plurality of estimated shape models is generated from a shape model, and wherein each of the medialization values is indicative of an amount by which each respective one of the estimated shape models is medialized relative to a current position of the anatomical object, determining respective cost values for each of the plurality of estimated shape models based at least in part on the respective determined medialization values for each of the plurality of estimated shape models, selecting an estimated shape model from the plurality of estimated shape model having a cost value of the respective cost values that satisfies a function for the cost value, and generating information indicative of the pre-morbid shape of the anatomical object based on the selected estimated shape model.

In one example, the disclosure describes a device for determining a pre-morbid shape of an anatomical object of an orthopedic joint of a patient, the device comprising a memory configured to store one or more of a shape model and a plurality of estimated shape model and processing circuitry. The processing circuitry is configured to determine respective medialization values for each of the plurality of estimated shape models, wherein the plurality of estimated shape models is generated from the shape model, and wherein each of the medialization values is indicative of an amount by which each respective one of the estimated shape models is medialized relative to a current position of the anatomical object, determine respective cost values for each of the plurality of estimated shape models based at least in part on the respective determined medialization values for each of the plurality of estimated shape models, select an estimated shape model from the plurality of estimated shape model having a cost value of the respective cost values that satisfies a function for the cost value, and generate information indicative of the pre-morbid shape of the anatomical object based on the selected estimated shape model.

In one example, the disclosure describes a computer-readable storage medium storing instructions thereon that when executed cause one or more processors to determine respective medialization values for each of a plurality of estimated shape models, wherein the plurality of estimated shape models is generated from a shape model, and wherein each of the medialization values is indicative of an amount by which each respective one of the estimated shape models is medialized relative to a current position of the anatomical object, determine respective cost values for each of the plurality of estimated shape models based at least in part on the respective determined medialization values for each of the plurality of estimated shape models, select an estimated shape model from the plurality of estimated shape model having a cost value of the respective cost values that satisfies a function for the cost value, and generate information indicative of a pre-morbid shape of an anatomical object based on the selected estimated shape model.

In one example, the disclosure describes a system for determining a pre-morbid shape of an anatomical object of an orthopedic joint of a patient, the system comprising means for determining respective medialization values for each of a plurality of estimated shape models, wherein the plurality of estimated shape models is generated from a shape model, and wherein each of the medialization values is indicative of an amount by which each respective one of the estimated shape models is medialized relative to a current position of the anatomical object, means for determining respective cost values for each of the plurality of estimated shape models based at least in part on the respective determined medialization values for each of the plurality of estimated shape models, means for selecting an estimated shape model from the plurality of estimated shape model having a cost value of the respective cost values that satisfies a function for the cost value, and means for generating information indicative of the pre-morbid shape of the anatomical object based on the selected estimated shape model.

In one example, the disclosure describes a method for determining a pre-morbid shape of an anatomical object of an orthopedic joint of a patient, the method comprising receiving an aligned shape and a shape model, performing an iterative closest point (ICP) loop, wherein performing the ICP loop comprises modifying the aligned shape, comparing the modified aligned shape to the shape model, determining a cost value based on the comparison, and repeating the modifying, comparing, and determining until the cost value satisfies a threshold value to generate a first order shape, wherein the first order shape comprises the modified aligned shape associated with the cost value that satisfies the threshold value, performing an elastic registration (ER) loop, wherein performing the ER loop comprises receiving the first order shape and the shape model, determining respective cost values for each of a first set of plurality of estimated shape models based on the first order shape and respective plurality of estimated shape models, wherein the plurality of estimated shape models is generated based on the shape model, and determining a first estimated shape model of the plurality of estimated shape models associated with a cost value of the respective cost values that satisfies a first threshold value, wherein the estimated shape model comprises a first order shape model, and repeatedly performing the ICP loop and the ER loop until a cost value generated from an iteration of the ER loop satisfies a second threshold value to determine the pre-morbid shape of the anatomical object, wherein repeatedly performing the ICP loop and the ER loop comprises receiving, for the ICP loop, an order shape model generated by a previous ER loop and an order shape generated by a previous ICP loop, generating, by the ICP loop, a current order shape based on the order shape model and the order shape, receiving, for the ER loop, the current order shape and at least one of shape model or the order shape model generated by the previous ER loop, generating a next set of plurality of estimated shape models based on at least one of the shape model or the order shape model generated by the previous ER loop, determining respective cost values for each of the second set of plurality of estimated shape models based on the order shape of the current order shape and respective second set of plurality of estimated shape models, and determining a current estimated shape model of the second set of plurality of estimated shape models associated with a cost value of the respective cost values that satisfies the first threshold value, wherein the current estimated shape model comprises a current order shape model generated by the ER loop.

In one example, the disclosure describes a device for determining a pre-morbid shape of an anatomical object of an orthopedic joint of a patient, the device comprising a memory configured to store a shape model and processing circuitry. The processing circuitry is configured to receive an aligned shape and a shape model, perform an iterative closest point (ICP) loop, wherein to perform the ICP loop, the processing circuitry is configured to modify the aligned shape, compare the modified aligned shape to the shape model, determine a cost value based on the comparison, and repeat the modifying, comparing, and determining until the cost value satisfies a threshold value to generate a first order shape, wherein the first order shape comprises the modified aligned shape associated with the cost value that satisfies the threshold value, perform an elastic registration (ER) loop, wherein to perform the ER loop, the processing circuitry is configured to receive the first order shape and the shape model, determine respective cost values for each of a first set of plurality of estimated shape models based on the first order shape and respective plurality of estimated shape models, wherein the plurality of estimated shape models is generated based on the shape model, and determine a first estimated shape model of the plurality of estimated shape models associated with a cost value of the respective cost values that satisfies a first threshold value, wherein the estimated shape model comprises a first order shape model, and repeatedly perform the ICP loop and the ER loop until a cost value generated from an iteration of the ER loop satisfies a second threshold value to determine the pre-morbid shape of the anatomical object, wherein to repeatedly perform the ICP loop and the ER loop, the processing circuitry is configured to receive, for the ICP loop, an order shape model generated by a previous ER loop and an order shape generated by a previous ICP loop, generate, by the ICP loop, a current order shape based on the order shape model and the order shape, receive, for the ER loop, the current order shape and at least one of shape model or the order shape model generated by the previous ER loop, generate a next set of plurality of estimated shape models based on at least one of the shape model or the order shape model generated by the previous ER loop, determine respective cost values for each of the second set of plurality of estimated shape models based on the order shape of the current order shape and respective second set of plurality of estimated shape models, and determine a current estimated shape model of the second set of plurality of estimated shape models associated with a cost value of the respective cost values that satisfies the first threshold value, wherein the current estimated shape model comprises a current order shape model generated by the ER loop.

In one example, the disclosure describes a computer-readable storage medium storing instructions thereon that when executed cause one or more processors to receive an aligned shape and a shape model, perform an iterative closest point (ICP) loop, wherein the instructions that cause the one or more processors to perform the ICP loop comprise instructions that cause the one or more processors to modify the aligned shape, compare the modified aligned shape to the shape model, determine a cost value based on the comparison, and repeat the modifying, comparing, and determining until the cost value satisfies a threshold value to generate a first order shape, wherein the first order shape comprises the modified aligned shape associated with the cost value that satisfies the threshold value, perform an elastic registration (ER) loop, wherein the instructions that cause the one or more processors to perform the ER loop comprise instructions that cause the one or more processors to receive the first order shape and the shape model, determine respective cost values for each of a first set of plurality of estimated shape models based on the first order shape and respective plurality of estimated shape models, wherein the plurality of estimated shape models is generated based on the shape model, and determine a first estimated shape model of the plurality of estimated shape models associated with a cost value of the respective cost values that satisfies a first threshold value, wherein the estimated shape model comprises a first order shape model, and repeatedly perform the ICP loop and the ER loop until a cost value generated from an iteration of the ER loop satisfies a second threshold value to determine a pre-morbid shape of an anatomical object, wherein the instructions that cause the one or more processors to repeatedly perform the ICP loop and the ER loop comprise instructions that cause the one or more processors to receive, for the ICP loop, an order shape model generated by a previous ER loop and an order shape generated by a previous ICP loop, generate, by the ICP loop, a current order shape based on the order shape model and the order shape, receive, for the ER loop, the current order shape and at least one of shape model or the order shape model generated by the previous ER loop, generate a next set of plurality of estimated shape models based on at least one of the shape model or the order shape model generated by the previous ER loop, determine respective cost values for each of the second set of plurality of estimated shape models based on the order shape of the current order shape and respective second set of plurality of estimated shape models, and determine a current estimated shape model of the second set of plurality of estimated shape models associated with a cost value of the respective cost values that satisfies the first threshold value, wherein the current estimated shape model comprises a current order shape model generated by the ER loop.

In one example, the disclosure describes a system for determining a pre-morbid shape of an anatomical object of an orthopedic joint of a patient, the system comprising means for receiving an aligned shape and a shape model, means for performing an iterative closest point (ICP) loop, wherein the means for performing the ICP loop comprises means for modifying the aligned shape, means for comparing the modified aligned shape to the shape model, means for determining a cost value based on the comparison, and means for repeating the modifying, comparing, and determining until the cost value satisfies a threshold value to generate a first order shape, wherein the first order shape comprises the modified aligned shape associated with the cost value that satisfies the threshold value, means for performing an elastic registration (ER) loop, wherein the means for performing the ER loop comprises means for receiving the first order shape and the shape model, means for determining respective cost values for each of a first set of plurality of estimated shape models based on the first order shape and respective plurality of estimated shape models, wherein the plurality of estimated shape models is generated based on the shape model, and means for determining a first estimated shape model of the plurality of estimated shape models associated with a cost value of the respective cost values that satisfies a first threshold value, wherein the estimated shape model comprises a first order shape model, and means for repeatedly performing the ICP loop and the ER loop until a cost value generated from an iteration of the ER loop satisfies a second threshold value to determine the pre-morbid shape of the anatomical object, wherein the means for repeatedly performing the ICP loop and the ER loop comprises means for receiving, for the ICP loop, an order shape model generated by a previous ER loop and an order shape generated by a previous ICP loop, means for generating, by the ICP loop, a current order shape based on the order shape model and the order shape, means for receiving, for the ER loop, the current order shape and at least one of shape model or the order shape model generated by the previous ER loop, means for generating a next set of plurality of estimated shape models based on at least one of the shape model or the order shape model generated by the previous ER loop, means for determining respective cost values for each of the second set of plurality of estimated shape models based on the order shape of the current order shape and respective second set of plurality of estimated shape models, and means for determining a current estimated shape model of the second set of plurality of estimated shape models associated with a cost value of the respective cost values that satisfies the first threshold value, wherein the current estimated shape model comprises a current order shape model generated by the ER loop.

In one example, the disclosure describes a method for determining a pre-morbid shape of an anatomical object of an orthopedic joint of a patient, the method comprising determining a plane through the anatomical object from the image data, wherein the plane is a plane that is substantially through a middle of the anatomical object, determining a normal of the plane, determining a transverse axis through representations of sagittal cuts through the anatomical object, wherein the transverse axis is orthogonal to the normal, determining a patient coordinate system based on the normal and the transverse axis, generating an initial aligned shape that initially aligns the anatomical object from the image data to a shape model, and generating information indicative of the pre-morbid shape of the anatomical object based on the initial aligned shape.

In one example, the disclosure describes a device for determining a pre-morbid shape of an anatomical object of an orthopedic joint of a patient, the device comprising memory configured to store image data and processing circuitry. The processing circuitry is configured to determine a plane through the anatomical object from the image data, wherein the plane is a plane that is substantially through a middle of the anatomical object, determine a normal of the plane, determine a transverse axis through representations of sagittal cuts through the anatomical object, wherein the transverse axis is orthogonal to the normal, determine a patient coordinate system based on the normal and the transverse axis, generate an initial aligned shape that initially aligns the anatomical object from the image data to a shape model, and generate information indicative of the pre-morbid shape of the anatomical object based on the initial aligned shape.

In one example, the disclosure describes a computer-readable storage medium storing instructions that when executed cause one or more processors to determine a plane through the anatomical object from the image data, wherein the plane is a plane that is substantially through a middle of the anatomical object, determine a normal of the plane, determine a transverse axis through representations of sagittal cuts through the anatomical object, wherein the transverse axis is orthogonal to the normal, determine a patient coordinate system based on the normal and the transverse axis, generate an initial aligned shape that initially aligns the anatomical object from the image data to a shape model, and generate information indicative of a pre-morbid shape of an anatomical object based on the initial aligned shape.

In one example, the disclosure describes a system for determining a pre-morbid shape of an anatomical object of an orthopedic joint of a patient, the system comprising means for determining a plane through the anatomical object from the image data, wherein the plane is a plane that is substantially through a middle of the anatomical object, means for determining a normal of the plane, means for determining a transverse axis through representations of sagittal cuts through the anatomical object, wherein the transverse axis is orthogonal to the normal, means for determining a patient coordinate system based on the normal and the transverse axis; means for generating an initial aligned shape that initially aligns the anatomical object from the image data to a shape model, and means for generating information indicative of the pre-morbid shape of the anatomical object based on the initial aligned shape.

The details of various examples of the disclosure are set forth in the accompanying drawings and the description

DETAILED DESCRIPTION

Figure 1:
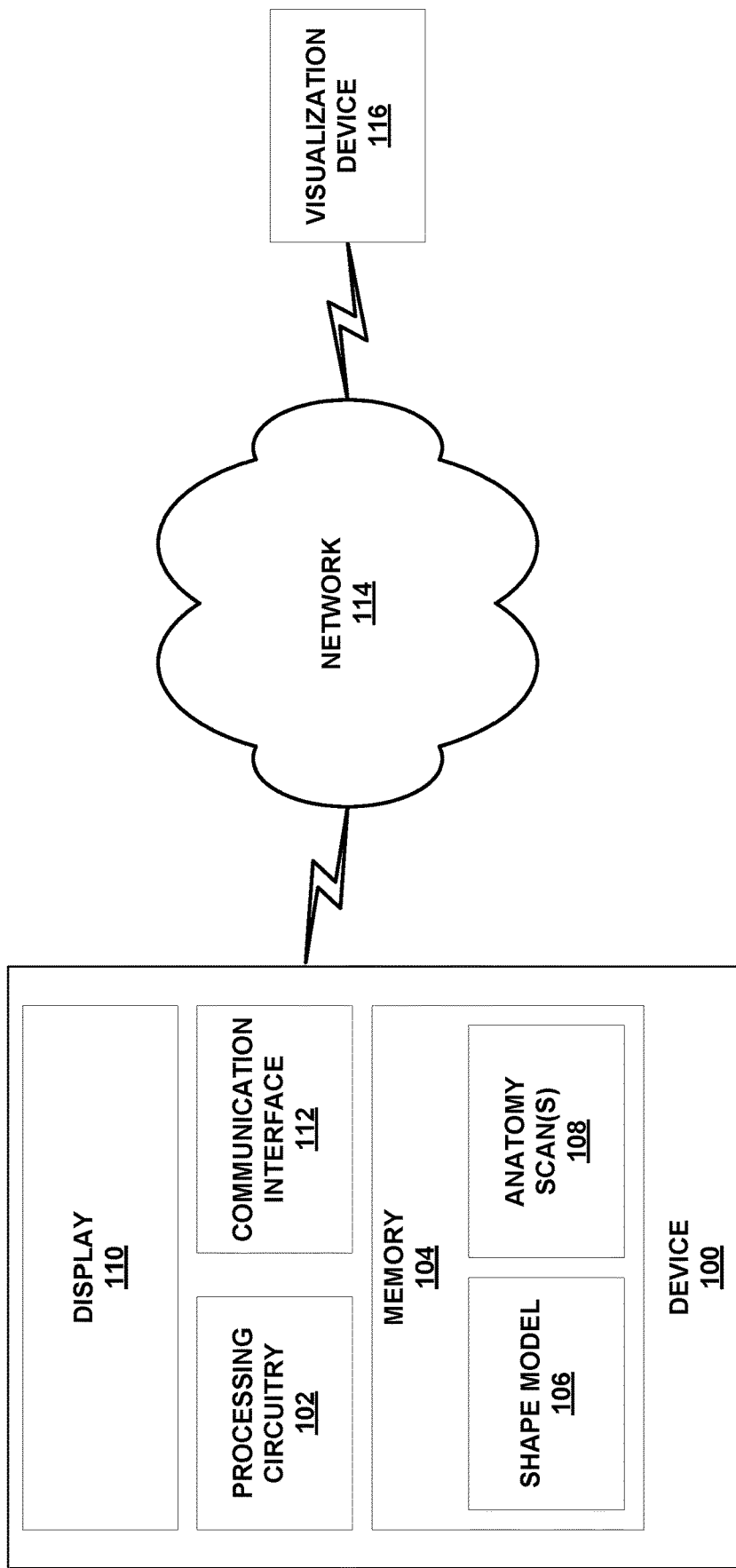
FIG. 1 is a block diagram illustrating an example computing device that may be used to implement the techniques of this disclosure.

A patient may suffer from a disease (e.g., aliment) that causes damage to the patient anatomy, or the patient may suffer an injury that causes damage to the patient anatomy. For shoulders, as an example of patient anatomy, a patient may suffer from primary glenoid humeral osteoarthritis (PGHOA), rotator cuff tear arthropathy (RCTA), instability, massive rotator cuff tear (HRCT), rheumatoid arthritis (RA), post-traumatic arthritis (PTA), osteoarthritis (OA), or acute fracture, as a few examples.

To address the disease or injury, a surgeon may perform a surgical procedure such as Reversed Arthroplasty (RA), Augmented Reverse Arthroplasty (RA), Standard Total Shoulder Arthroplasty (TA), Augmented Total Shoulder Arthroplasty (TA), or Hemispherical shoulder surgery, as a few examples. There may be benefits for the surgeon to determine, prior to the surgery, characteristics (e.g., size, shape, and/or location) of the patient anatomy. For instance, determining the characteristics of the patient anatomy may aid in prosthetic selection, design and/or positioning, as well as planning of surgical steps to prepare a surface of the damaged bone to receive or interact with a prosthetic. With advance planning, the surgeon can determine, prior to surgery, rather than during surgery, steps to prepare bone or tissue, tools that will be needed, sizes and shapes of the tools, the sizes and shapes or other characteristics of one or more prostheses that will be implanted and the like.

As described above, pre-morbid characterization refers to characterizing the patient anatomy as it existed prior to the patient suffering disease or injury. However, pre-morbid characterization of the anatomy is generally not available because the patient may not consult with a doctor or surgeon until after suffering the disease or injury.

In some cases, it may be possible to use one side of the patient (e.g., shoulder on one side) as representative of the pre-morbid characterization of the other side (e.g., shoulder on other side). However, the disease could be bilateral, meaning that there is impact on both sides. Also, the patient anatomy may not be symmetric (e.g., shoulders are not symmetric) and may not reflect the pre-morbid characteristics of the contralateral side.

Pre-morbid anatomy, also called native anatomy, refers to the anatomy prior to the onset of a disease or the occurrence of an injury. Even after disease or injury, there may be portions of the anatomy that are healthy and portions of the anatomy that are not healthy (e.g., diseased or damaged). The diseased or damaged portions of the anatomy are referred to as pathological anatomy, and the healthy portions of the anatomy are referred to as non-pathological anatomy.

This disclosure describes example techniques to determine a representation of a pre-morbid anatomical object (e.g., a predictor of the pre-morbid anatomical object) using statistical shape model (SSM), and particularly, determining a shape model representative of the patient anatomical object with current patient anatomy in accordance with a cost function. For example, the disclosure describes aligning a segmented shape representing the current patient anatomical object having the pathological and non-pathological anatomy to a coordinate system of an initial shape model. The initial shape model is an example of the SSM. As described in more detail, to perform such alignment to the coordinate system, a computing device may determine a coordinate system for the segmented shape even where not all image information or too much image information is available due to under- and over-segmentation.

After aligning the segmented shape to the coordinate system of the initial shape model, the computing device may deform the shape model through an iterative process to register the shape model to the segmented shape. The registration may include adjusting the size and shape of the shape model to the current patient anatomical objects and adjusting a location of the shape model to align with the current patient anatomical objects (e.g., register in 3D the shape model to the current patient anatomical objects). The result of the registration may be a shape model that is an approximation of the pre-morbid size and shape of the patient anatomical object.

The segmented shape is aligned to the initial shape model, which is an example of the SSM. For instance, a coordinate system of segmented shape is aligned to the coordinate system of the initial shape model so that the segmented shape is defined in the same space as the initial shape model. The result of the aligning is an aligned shape. Then, the initial shape models is modified in an iterative manner, to generate a final shape model that is a pre-morbid approximation of the anatomical object. For example, assume that the patient anatomical object includes an injured or diseased glenoid (e.g., pathological glenoid). The initial shape model is an SSM of the anatomical object but with non-pathological glenoid. With the example techniques described in this disclosure, the final shape model is registered to the patient anatomical object (e.g., so that the final shape model is approximately the same size and shape as the patient anatomical object). In this example, the non-pathological glenoid of the final shape model is an approximation of the pre-morbid size and shape of the patient glenoid.

The statistical shape model (SSM) may be a model generated from determining a mean shape from participants in a study. For example, using patient demographic information and various measurements extracted from the segmented image data, a computing device may select or generate the appropriate shape model for the patient. In some examples, the SSM may be constant for all patients, rather than generating an appropriate shape model for a particular patient. The shape model may be represented as a point cloud or a function with parameters for generating a point cloud.

As described above, a computing device may align the segmented shape (e.g., a representation of the current patient anatomical object) to the initial shape model. To perform the alignment, the computing device may determine a coordinate system for the segmented shape. However, because the anatomical object includes pathological anatomy that is diseased or damaged, it is possible that portions of the pathological anatomy, used for determining a coordinate system, are no longer present in the patient. Also, registration (e.g., deformation of the shape model to register the shape model to aligned shape) may be limited to comparison of the shape model to the non-pathological anatomy.

Moreover, imaging techniques may not properly capture the non-pathological anatomy. For instance, based on scans performed on the patient, such as computed tomography (CT) scans or radiographs such as x-ray, MM, and ultrasound, a computing device may generate image data of the patient anatomy. In under-segmentation, it is possible that certain portions of the patient anatomy (e.g., scapula) are not fully captured, and there are missing portions (e.g., in this case, a resulting segmented object does not include the entire actual anatomical object). This under-segmentation could be due to types of machines used to scan the patient, noise in the scans, bone-to-bone contact, etc.

In some cases, the radiologist tries to minimize patient's exposure to irradiation and stops the scanner once the anatomical object of interest is reached. For instance, the radiologist may stop scanning the patient anatomy when the glenoid is reached. In such cases, image information for other anatomical objects may be lost (e.g., lose the inferior and medial parts of the scapula).

In over-segmentation, it is possible that additional body parts are present in the scans that can impact the alignment (e.g., a resulting segmented object includes more than the actual anatomical objects). For instance, the scan of the scapula is needed, but due to over-segmentation, additional bony parts like the clavicle or the ribs may be included in the segmentation.

Non-pathological anatomy is desirable for aligning the segmented shape to the initial shape model to generate the aligned shape and to perform the registration of a shape model to the aligned shape. However, the non-pathological anatomy may not be available from the scans due to under- or over-segmentation. This disclosure describes example techniques to generate the pre-morbid characterization even when there is under- and/or over-segmentation of anatomical objects in image data.

As described above, a computing device may align the segmented shape (e.g., image data representing the current patient anatomical object) to a shape model to generate an aligned shape. In one or more examples, a computing device may determine a patient coordinate system from the segmented shape based on a best fit plane and transverse axis, as described in more detail below, so that the computing device does not need to rely on anatomical landmarks that may not be present in the scans due to under-segmentation or may not be discernible due to over-segmentation. With the determined patient coordinate system, a computing device may align the segmented shape to the shape model to generate an initial aligned shape (e.g., by performing transformations to the segmented shape generated from the image data so that the anatomical objects are aligned with the shape model).

However, due to under- or over-segmentation, there may be misalignment of the initial aligned shape relative to the actual anatomy of the patient. For example, a segmented shape may exclude one or more portions associated with an actual, anatomic object, in the case of under-segmentation, or include one or more portions not associated with the actual, anatomic object, in the case of over-segmentation. In one or more examples, a computing device may modify parameters of the initial aligned shape (e.g., to modify the shape and/or position of the initial aligned shape), using techniques described in more detail below, to generate an aligned shape. As one example, the computing device may modify the parameters of the initial aligned shape such that the initial aligned shape rotates around two anatomical axes (e.g., the superior axis and the axis perpendicular to the scapula's plane, which are two of the three axis in the 3D coordinate system). This may be because of insincerity about the computation of the transverse axis (e.g., the third axis in the 3D coordinate system), as described in more detail. The aligned shape is substantially proximal to the anatomy of the patient within the initial shape model coordinate system. In this case, substantially proximal refers to the aligned shape having approximately the same size (e.g., 3D volume) as the anatomical objects and having the same orientation of the anatomical objects. The aligned shape may be fairly close to be aligned to the segmented anatomical objects.

After generating the aligned shape, further updates, as described below, may be needed to generate a pre-morbid characterization of the patient anatomy (e.g., a graphical shape model that is a predictor of the patient's anatomy prior to damage). Hence, the aligned shape may be referred to as an intermediate aligned shape. For instance, the computing device may perform a multiple loop iterative process. For example, the computing device may be configured to perform an iterative closest point (ICP) algorithm. The initial input to the ICP algorithm is the aligned shape and the initial shape model (e.g., the SSM). The ICP algorithm deforms the aligned shape in an iterative process to register the aligned shape to the initial shape model (e.g., reshapes the aligned shape to generate a shape model that is approximately the same size and shape as the initial shape model). The example techniques for performing the ICP algorithm are described in more detail below. The output of the ICP algorithm is a first order shape.

The computing device may utilize the first order shape and the initial shape model (e.g., SSM) as an input for an elastic registration algorithm. The elastic registration algorithm is described in more detail below, and generally includes generating a plurality of estimated shape models based on the initial shape model (e.g., by deforming the initial shape model). The computing device may select one of the estimated shape models as a first order shape model based on a cost function value that relies upon distances and orientation between the estimated shape models and the first order shape, constraints on medialization of anatomy, and parameter weighting. The result of the elastic registration algorithm is a first order shape model. The first order shape model may be similar to in size and shape, but not exact as, the first order shape.

These example operations may conclude one iteration of the pre-morbid characterization algorithm. To summarize, in the first iteration of the pre-morbid characterization, the computing device performed the ICP algorithm. For the ICP algorithm, the computing device utilized the aligned shape and the initial shape model and deformed the aligned shape to register to the aligned shape to generate a first order shape. After the ICP algorithm, the computing device performed the elastic registration algorithm. For the elastic registration algorithm, the computing device utilized the initial shape model to generate a plurality of estimated shape models and determined one of the estimated shape models as a first order shape model based on distances and orientation between the estimated shape models and the first order shape, constraints on medialization of anatomy, and parameter weighting as the conclusion of a first iteration of the pre-morbid characterization algorithm.

Then, the computing device may perform a second iteration of the pre-morbid characterization algorithm. In the second iteration, the computing device may again perform the ICP algorithm. In this iteration, the input to the ICP algorithm is the first order shape, as previously determined, and the first order shape model, as previously determined. The computing device may deform the first order shape to register the first order shape to the first order shape model using the ICP algorithm to generate a second order shape (e.g., where the second order shape is approximately the same, in size and shape, as the first order shape model).

The computing device may then perform the elastic registration algorithm using the initial shape model or the first order shape model, as previously determined, and the second order shape, as now determined based on the ICP algorithm. For example, the computing device may determine a plurality of estimated shape models based on the initial shape model or the first order shape model. The computing device may determine one of the estimated shape models as a second order shape model based on a cost function value that relies upon distances and orientation between the estimated shape models and the second order shape, constraints on medialization of anatomy, and parameter weighting.

This may conclude a second iteration of the pre-morbid characterization algorithm. The iterations of the pre-morbid characterization algorithm keep repeating with next order shape models until the overall cost function value used for the elastic registration algorithm satisfies a threshold value (e.g., less than threshold value including example where cost function value is minimized). The result is a final shape model that is approximately the same size and shape as the current patient anatomical object prior to the disease or injury.

The computing device may output a graphical representation of the final shape model as the information indicative of the pre-morbid characterization of the anatomical object. As another example, the computing device may output length and shape information of the determined aligned shape model as information indicative of the pre-morbid characterization of the anatomy. For instance, the computing device may output for display information for final shape model and its anatomical measurements (e.g., version and inclination) displayed on top of the final shape model, as an example of the pre-morbid shape of the anatomical object that is now diseased or injured (e.g., pathological).

The surgeon may then use the pre-morbid characterization to plan the surgery. For example, with the pre-morbid shape, the surgeon may determine which implant to use and how to perform the implant surgery so that the result of the surgery is that the patient's experience (e.g., in ability of movement) is similar to before the patient experienced injury or disease.

FIG. 1 is a block diagram illustrating an example computing device that may be used to implement the techniques of this disclosure. FIG. 1 illustrates device 100, which is an example of a computing device configured to perform one or more example techniques described in this disclosure.

Device 100 may include various types of computing devices, such as server computers, personal computers, smartphones, laptop computers, and other types of computing devices. Device 100 includes processing circuitry 102, memory 104, and display 110. Display 110 is optional, such as in examples where device 100 is a server computer.

Examples of processing circuitry 102 include one or more microprocessors, digital signal processors (DSPs), application specific integrated circuits (ASICs), field programmable gate arrays (FPGAs), discrete logic, software, hardware, firmware or any combinations thereof. In general, processing circuitry 102 may be implemented as fixed-function circuits, programmable circuits, or a combination thereof. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Processing circuitry 102 may include arithmetic logic units (ALUs), elementary function units (EFUs), digital circuits, analog circuits, and/or programmable cores, formed from programmable circuits. In examples where the operations of processing circuitry 102 are performed using software executed by the programmable circuits, memory 104 may store the object code of the software that processing circuitry 102 receives and executes, or another memory within processing circuitry 102 (not shown) may store such instructions. Examples of the software include software designed for surgical planning.

Memory 104 may be formed by any of a variety of memory devices, such as dynamic random access memory (DRAM), including synchronous DRAM (SDRAM), magnetoresistive RAM (MRAM), resistive RAM (RRAM), or other types of memory devices. Examples of display 110 include a liquid crystal display (LCD), a plasma display, an organic light emitting diode (OLED) display, or another type of display device.

Device 100 may include communication interface 112 that allows device 100 to output data and instructions to and receive data and instructions from visualization device 116 via network 114. For example, after determining a pre-morbid characteristic of the anatomical object, using techniques described in this disclosure, communication interface 112 may output information of the pre-morbid characteristic to visualization device 116 via network 114. A surgeon may then view a graphical representation of the pre-morbid anatomical object with visualization device 116 (e.g., possibly with the pre-morbid anatomical object overlaid on top of image of the injured or diseased anatomical object). In some examples, viewing the pre-morbid anatomical object overlaid on top of image of the injured or diseased anatomical object gives the surgeon understanding of how to perform implantation so that the result of the implantation mimics the pre-morbid shape of the anatomical object.

Communication interface 112 may be hardware circuitry that enables device 100 to communicate (e.g., wirelessly or using wires) to other computing systems and devices, such as visualization device 116. Network 114 may include various types of communication networks including one or more wide-area networks, such as the Internet, local area networks, and so on. In some examples, network 114 may include wired and/or wireless communication links.

Visualization device 116 may utilize various visualization techniques to display image content to a surgeon. Visualization device 116 may be a mixed reality (MR) visualization device, virtual reality (VR) visualization device, holographic projector, or other device for presenting extended reality (XR) visualizations. In some examples, visualization device 116 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Visualization device 1116 may utilize visualization tools that are available to utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Technology, Inc. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

As illustrated, memory 104 stores data representative of a shape model 106 and data representative of anatomy scans 108. Anatomy scans 108 are examples of computed tomography (CT) scans of a patient, e.g., as represented by CT scan image data. Anatomy scans 108 may be sufficient to reconstruct a three-dimensional (3D) representation of the anatomy of the patient, such as the scapula and glenoid as examples of patient anatomy (e.g., by automated segmentation of the CT image data to yield segmented anatomical objects). One example way of automated segmentation is described in U.S. Pat. No. 8,971,606. There may be various other ways in which to perform automated segmentation, and the techniques are not limited to automated segmentation using techniques described in U.S. Pat. No. 8,971,606. As one example, segmentation of the CT image data to yield segmented objects includes comparisons of voxel intensity in the image data to determine bony anatomy and comparisons to estimated sizes of bony anatomy to determine a segmented object. Moreover, the example techniques may be performed with non-automated segmentation techniques, where a medical professional evaluates the CT image data to segment anatomical objects, or some combination of automation and user input for segmenting anatomical objects.

In one or more examples, anatomy scans 108 may be scans of anatomy that is pathological due to injury or disease. The patient may have an injured shoulder requiring surgery, and for the surgery or possibly as part of the diagnosis, the surgeon may have requested anatomy scans 108 to plan the surgery. A computing device (like device 100 or some other device) may generate segmentations of the patient anatomy so that the surgeon can view anatomical objects and the size, shape, and interconnection of the objects with other anatomy of the patient anatomy needing surgery.

In one or more examples, processing circuitry 102 may utilize image data of scans 108 to compare (e.g., size, shape, orientation, etc.) against a statistical shape model (SSM) as a way to determine characteristics of the patient anatomy prior to the patient suffering the injury or disease. In some examples, processing circuitry 102 may compare 3D point data of non-pathological points of anatomical objects of patient anatomy in the image data of scans 108 to points in SSM.

For instance, scans 108 provide the surgeon with a view of the current characteristics of the damaged or diseased anatomy. To reconstruct the anatomy (i.e., to represent a pre-morbid state), the surgeon may find it beneficial to have a model indicating the characteristics of the anatomy prior to the injury or disease. For instance, the model may be a predictor of the anatomy of the patient prior to damage or disease, which allows the surgeon to plan the surgery. For example, with pre-morbid model, the surgeon may determine the extent of the injury or progression of the disease, which can assist the surgeon in determining type of implant, location of implant, or other corrective actions to be taken. However, it may be likely the patient did not consult with the surgeon until after the injury occurred or disease progressed, and therefore, a model of the patient anatomy prior to the injury or disease (e.g., pre-morbid or native anatomy) may not be available. Using the SSM as a way to model the pre-morbid anatomy allows the surgeon to determine characteristics of the pre-morbid patient anatomy.

SSMs are a compact tool to represent shape variations among a population of samples (database). For example, a clinician or researcher may generate a database of image scans, such as CT image data, of different people representative of the population as a whole who do not suffer from damaged or diseased glenoid, humerus, or neighboring bones. The clinician or researcher may determine a mean shape for the patient anatomy from the shapes in the database. In FIG. 1, memory 104 stores information indicative of shape model 106. As one example, shape model 106 represents a mean shape for the anatomical object (e.g., glenoid, humeral head, etc.) of patient anatomy from the shapes in the database. Other examples of shape model 106 are possible, such as a mode or median of the shapes in the database. A weighted average is another possible example of shape model 106. Shape model 106 may be a surface or volume of points (e.g., a graphical surface or a volume of points that define a 3D model), and the information indicative of mean shape may be coordinate values for vertices of primitives that interconnect to form the surface. Techniques to generate an SSM like shape model 106 and values associated with generating shape model 106 can be found in various literature such as from: http://www.cmlab.csie.ntu.edu.tw/~cyy/learning/papers/PCA_ASM.pdf dated Aug. 22, 2006. Other ways in which to generate shape model 106 are possible.

With shape model 106, processing circuitry 102 may represent anatomy shape variations by adding points or values of shape model 106 to a covariance matrix. For example, the SSM can be interpreted as a linear equation:

$$s_i = s' + \Sigma_i b_i \sqrt{\lambda_i} \times v_i.$$

In the above equation, s' is shape model 106 (e.g., point cloud of mean shape as one example, where point cloud defines coordinates of points within shape model 106, such as vertices of primitives that form shape model 106). In the equation, is the eigenvalues and $v_i$ is the eigenvectors of the covariance matrix respectively (also called modes of variations). The covariance matrix represents the variance in a dataset. The element in the i, j position is the co-variance between the i-th and j-th elements of a dataset array.

SSM stands for constructing the covariance matrix of the database then performing "singular value decomposition" which extracts a matrix of principal vectors (also called eigenvectors) and another diagonal matrix of positive values (called eigenvalues). Eigenvectors ($v_i$ in the equation) are new coordinate system bases of the database. Eigenvalues ($\lambda$ in the equation) represent the variance around the eigenvectors ($v_i$). Together eigenvectors and eigenvalues may reflect the amount of variation around the corresponding axis.

This mathematical equation allows processing circuitry 102 to create an infinite number of instances of $s_j$ (e.g., different variations of the shape model) by simply changing the weights $b_i$ of the covariance matrix. For instance, to generate a new shape model, processing circuitry may determine a value of $b_i$, and determine a new value of $s_j$. In the above example, $\lambda_i$ and $v_i$ and s' are all known based on the manner in which s' was generated (e.g., based on the manner in which shape model 106 was generated). By selecting different values of processing circuitry 102 may determine different instances of a shape model (e.g., different $s_i$ which are different variations of the shape model 106).

The shape model(s) may represent what an anatomical object should look like for a patient. As described in more detail, processing circuitry 102 may compare points (e.g., in the 3D cloud of points) of the shape model of the anatomical object with anatomical points represented in the image data of scans 108, as anatomical points of the anatomical object that are not impacted or minimally impacted by the injury or disease (e.g., non-pathological points). Based on the comparison, processing circuitry 102 may determine a pre-morbid characterization of the anatomical object.

As an example, assume that the surgeon would like to determine the pre-morbid characteristics of the glenoid cavity for shoulder surgery. There is a correlation between the shape of the glenoid cavity and the bony zone around it, such as the medical glenoid vault, the acromion, and the coracoid. Shape model 106 may be the mean shape of the scapula that includes the glenoid cavity. Assume that in the patient the glenoid cavity is pathological (e.g., diseased or damaged).

In accordance with example techniques described in this disclosure, processing circuitry 102 may determine the instance of "s" (e.g., shape model of scapula with glenoid cavity) that best matches the non-pathological anatomy of the anatomical object of the patient (e.g., non-pathological portions of the scapula in scans 108). The glenoid cavity, in the instance of "s," that best matches the non-pathological anatomy (referred to as s* and represented by a point cloud similar to the shape model) may be indicative of the pre-morbid characterization of the pathological glenoid cavity.

Processing circuitry 102 may determine the instance of s* (e.g., shape model of scapula with glenoid cavity that best matches the non-pathological portions of the patient's scapula). The non-pathological portions may be portions of the anatomical object with minimal to no impact from the disease or injury, where the anatomical object and its surrounding anatomy are taken from the segmentation performed by scans 108 to segment out the anatomical object.

In some examples, to determine pre-morbid characterization of a particular anatomical object, anatomy beyond the anatomical object may be needed to align the shape model. For instance, to determine pre-morbid characterization of the glenoid, anatomy of the scapula may be needed to align the shape model. Then, the glenoid of the shape model represents the pre-morbid characterization of the patient's glenoid. Hence, the shape model may not be limited to modeling just the anatomical object of interest (e.g., glenoid) but may include additional anatomical objects.

Processing circuitry 102 may perform the following example operations: (1) initially align the segmented anatomical object from image data of scans 108 to a coordinate system of shape model 106 to generate an initial aligned shape; (2) compensate for errors in the initial alignment due to under and over segmentation, where under- and over-segmentation are due to imperfections in generating scans 108, to generate an aligned shape (also called intermediate aligned shape); and (3) perform iterative operations that includes iterative closest point (ICP) operations and elastic registration to determine the instance of s* (i.e., the instance of s' that most closely matches the patient anatomy as identified by the segmentation object). Example techniques to perform these operations are described in more detail below.

Accordingly, there may be a few technical problems with generating the pre-morbid characterization of the patient anatomy. One issue may be that due to under- or over-segmentation the image data needed from scans 108 is not available or distorted creating a challenge to align the segmented object to shape model 106. Another issue may be that once there is alignment to shape model 106, registration of shape model 106 to the segmented object may be poor, resulting in poor pre-morbid characterization.

This disclosure describes example techniques that allow alignment of the segmented object to shape model 106 even in situations where there is under- or over-segmentation. This disclosure also describes example techniques to register shape model 106 to the segmented object (e.g., in multiple level iterative processes that uses ICP and elastic registration). The example techniques described in this disclosure may be use separately or together. For instance, in one example, processing circuitry 102 may be configured to perform alignment of the segmented object to shape model 106 utilizing example techniques described in disclosure but perform registration of shape model 106 to the segmented object using some other techniques. In one example, processing circuitry 102 may utilize some other technique to perform alignment of the segmented object to shape model 106 but perform registration of shape model 106 to the segmented object using one or more example techniques described in this disclosure. In some examples, processing circuitry 102 may perform the example alignment and registration techniques described in this disclosure.

As described above, processing circuitry 102 may align the segmented object (e.g., as segmented using example techniques such as voxel intensity comparisons) to shape model 106. In this disclosure, the alignment refers to changes to the coordinate system of the segmented object so that the segmented object is in same coordinate system as shape model 106. As also described above, one example of shape model 106 is a shape model of the anatomy of the scapula with glenoid cavity, where the glenoid cavity is the injured or diseased anatomical object. For instance, shape model 106 is defined in its own coordinate system and may be different than the patient coordinate system (e.g., coordinate system to define the point cloud of 3D points in scans 108). The patient coordinate system is the coordinate system used to define points within the anatomy of the patient in scans 108 that includes non-pathological points and pathological points. The non-pathological points refer to the points in scans 108 for non-pathological anatomy, and the pathological points refer to points in scans 108 for pathological anatomy.

There may be various ways in which to determine pathological and non-pathological points. As one example, the surgeon may review the image data of scans 108 to identify pathological and non-pathological points. As another example, the surgeon may review a graphical representation of the segmented object to identify pathological and non-pathological points. As another example, there may be an assumption that certain anatomical points are rarely injured or diseased and are present in image data of scans 108. For instance, the medical glenoid vault, the acromion, and the coracoid, are a few examples. Additional examples include trigonum scapulae and angulus inferior. However, one or more both trigonum scapulae and angulus inferior may not be present or distorted in the image data of scans 108 due to the over- and under-segmentation.

In one or more examples, processing circuitry 102 may determine a patient coordinate system, which is the coordinate system recorded for the CT scan data of scans 108. Shape model 106 may be defined in its own coordinate system. Processing circuitry 102 may determine the coordinate system of shape model 106 based on the metadata stored with shape model 106, where the metadata was generated as part of determining the mean of the shapes in the database. Processing circuitry 102 may determine a transformation matrix based on the patient coordinate system and the coordinate system of shape model 106. The transformation matrix is a way by which processing circuitry 102 transforms the segmented object (e.g., points in the 3D volume of points) into the coordinate system of shape model 106. For example, points in the 3D volume of points of the segmented object may be defined with (x, y, z) coordinate values. The result of the transformation may be coordinates (x', y', z') coordinate values that are aligned to the coordinate system of shape model 106. Processing circuitry 102 calculates the transformation matrix through a close-form equation.

There are multiple ways to determine the transformation matrix. As one example, the coordinate system may be c=(x,y,z,o), where x, y and z are the orthogonal basis 3D vectors and o is the origin (c is a 4×4 homogeneous matrix with the last raw is (0,0,0,1)). The new coordinate system to which the segmented object is to be transformed is C=(X, Y,Z,O). In this example, the transformation matrix is then: T=c^−1×C.

Accordingly, processing circuitry 102 may determine the patient coordinate system. FIGS. 2 to 8 describe example ways in which processing circuitry 102 determines the patient coordinate system. As described in more detail, even after determining the patient coordinate system, further adjustment to shape model 106 may be needed to properly align the segmented object (e.g., patient anatomy) to shape model 106. For instance, because of over- or under-segmentation, missing or distorted image data cannot be used to determine the patient coordinate system. Therefore, processing circuitry 102 utilizes image data that is available to perform an initial alignment, but then may perform further operations to fully align the segmented object to shape model 106.

Figure 2:
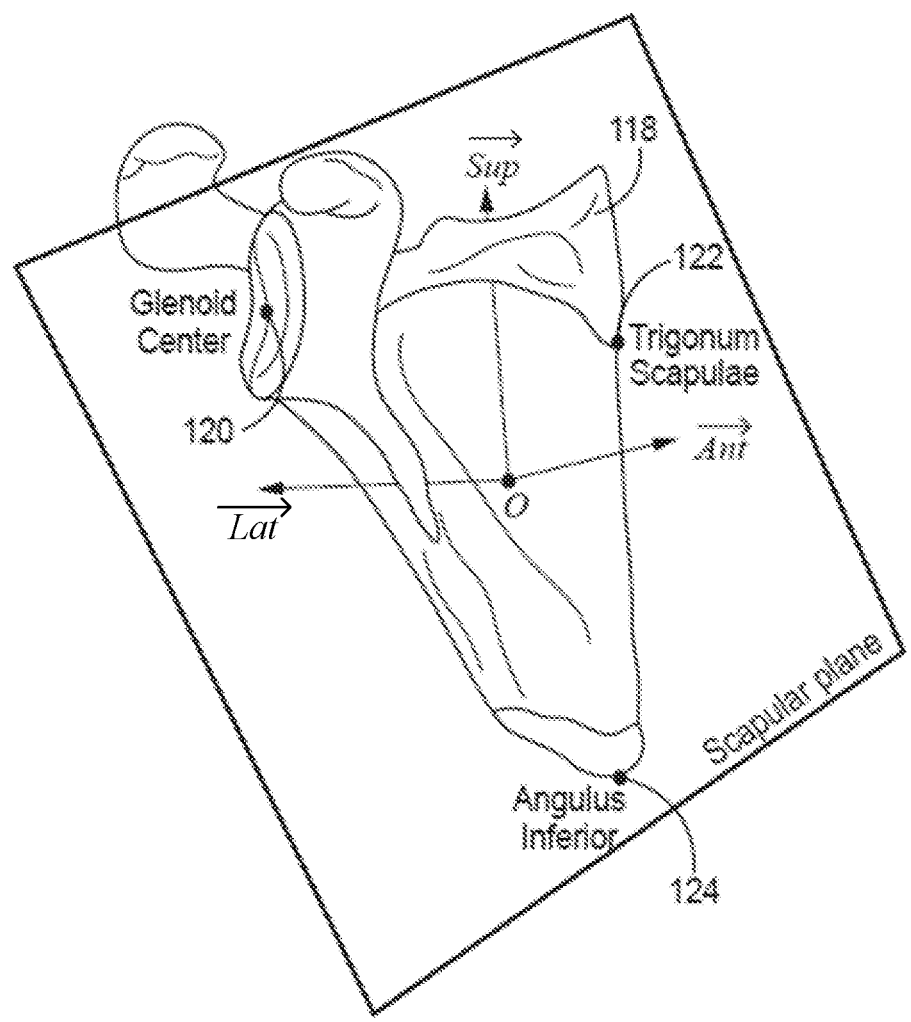
FIG. 2 is an illustration of a scapula having points of interest used to determine a coordinate system of a patient.

FIG. 2 is an illustration of a scapula having points of interest used to determine coordinate system of a patient. For instance, FIG. 2 illustrates scapula 118 having glenoid center 120, trigonum scapulae 122, and angulus inferior 124. Some techniques utilize glenoid center 120, trigonum scapulae 122, and angulus inferior 124 to determine the patient coordinate system. For instance, glenoid center 120, trigonum scapulae 122, and angulus inferior 126 may be considered as forming a triangle, and processing circuitry 102 may determine a center point (e.g., in 3D) of the triangle as the origin of the patient coordinate system.

However, such techniques may not be available in cases of over- and under-segmentation. As one example, in under-segmentation, scans 108 may be inferiorly and/or superiorly and/or medially truncated and trigonum scapulae 122 and angulus inferior 124 may not be present in the segmented objects extracted from the image data of scans 108. Therefore, processing circuitry 102 may not be able to utilize all three of glenoid center 120, trigonum scapulae 122, and angulus inferior 124 for purposes of determining patient coordinate system.

In one or more examples, where specific landmarks (e.g., glenoid center 120, trigonum scapulae 122, and angulus inferior 124) are not available as segmented anatomical objects in the image data of scans 108, processing circuitry 102 may define the patient coordinate system based on the scapula normal (e.g., a vector normal to scapula 118) and a transverse axis based on the 3D information of image data of scans 108. As described in more detail, processing circuitry 102 may determine the scapula normal based on the normal of the best fit plane to the body of scapula 118. Processing circuitry 102 may determine the transverse axis by fitting a line through the spongious region that lies between the supraspinatus fossa, the spine, and the scapula body. Using the spongious region, processing circuitry 102 may define a Cartesian (e.g., x, y, z) coordinate system (although other coordinate systems are possible). The origin of the coordinate system may be glenoid center 120; although other origins are possible.

In this manner, processing circuitry 102 may determine a coordinate system for the patient based on anatomical objects that are present in the image data of scans 108, even where there is over- or under-segmentation. Based on the coordinate system, processing circuitry 102 may align the segmentation objects to the coordinate system of shape model 106 (e.g., initial SSM) and iteratively deform shape model 106 to register a shape model (e.g., a deformed version of shape model 106) to the patient segmentation object to determine a pre-morbid characterization.

Figure 3A:
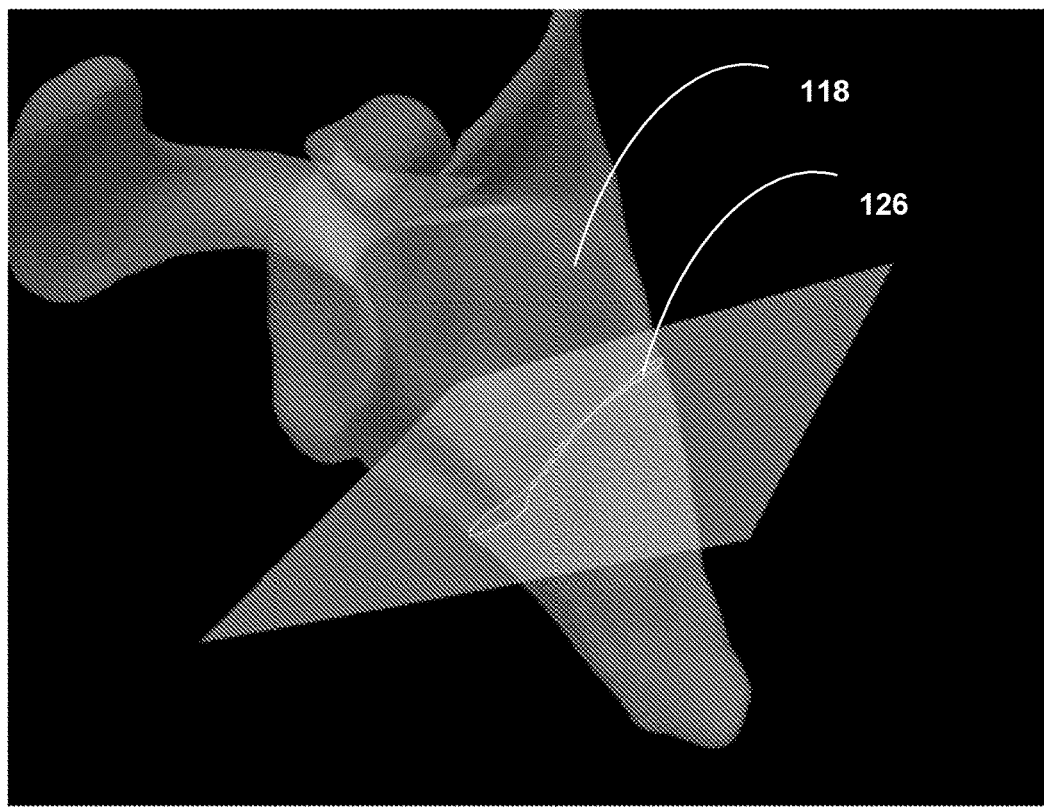
FIGS. 3A and 3B are illustrations of a planar cut through a scapula for determining a coordinate system of a patient.
Figure 3B:
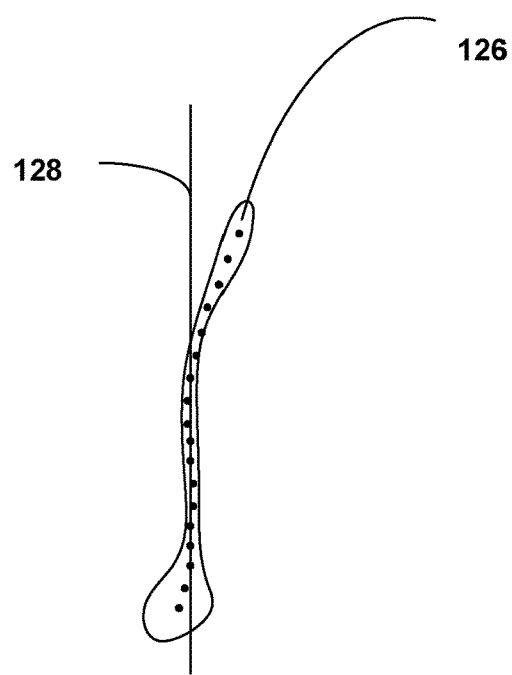

FIGS. 3A and 3B are illustrations of a planar cut through a scapula for determining a patient coordinate system that may not rely upon anatomical objects whose image data is unavailable due to over- or under-segmentation. For instance, unlike example of FIG. 2 that relied upon glenoid center 120, trigonum scapulae 122, and angulus inferior 124, which may not be available due to under- or over-segmentation, the example techniques illustrated with respect to FIGS. 3A and 3B may not rely on anatomical objects that are unavailable due to under- or over-segmentation.

As illustrated in FIG. 3A, one of scans 108 may be a scan of an axial cut through scapula 118, which shows scapula portion 126. FIG. 3B is a top view of scapula portion 126 of FIG. 3A through scapula 118.

FIG. 3B illustrates a plurality of dots, representing an intersecting plane through portion 136, that go through scapula portion 126. In one or more examples, processing circuitry 102 may determine a plane that intersects through scapula portion 126. The intersection of the plane through portion 126 is shown with the dots. For example, FIG. 3B illustrates line 128. Line 128 intersects a majority of the dots in scapula portion 126.

The dots in scapula portion 126 may be the "skeleton" of the surrounding contour. The skeleton is dots through the contour that are each the same distance to their respective nearest boundary. Although the skeleton is described, in some examples, the dots in scapula portion 126 may be center points, as another example.

Processing circuitry 102 may determine the image data that forms portion 126. Processing circuitry 102 may determine dots of portion 126 (e.g., skeleton dots or center dots as two non-limiting examples), as illustrated. Processing circuitry 102 may determine a plane that extends up from line 128 toward the glenoid and extends downward from line 128 toward the angulus inferior.

For example, although FIG. 3A illustrates one example axial cut, processing circuitry 102 may determine a plurality of axial cuts, and determine the points through the axial cuts, similar to FIG. 3B. The result may be a 2D points for each axial cut, and processing circuitry 102 may determine a line, similar to like 128, through each of the axial cuts. Processing circuitry 102 may determine a plane that extends through the lines for each axial cut through scapula 118. This plane is through scapula 118 and is illustrated in FIG. 4.

Figure 4:
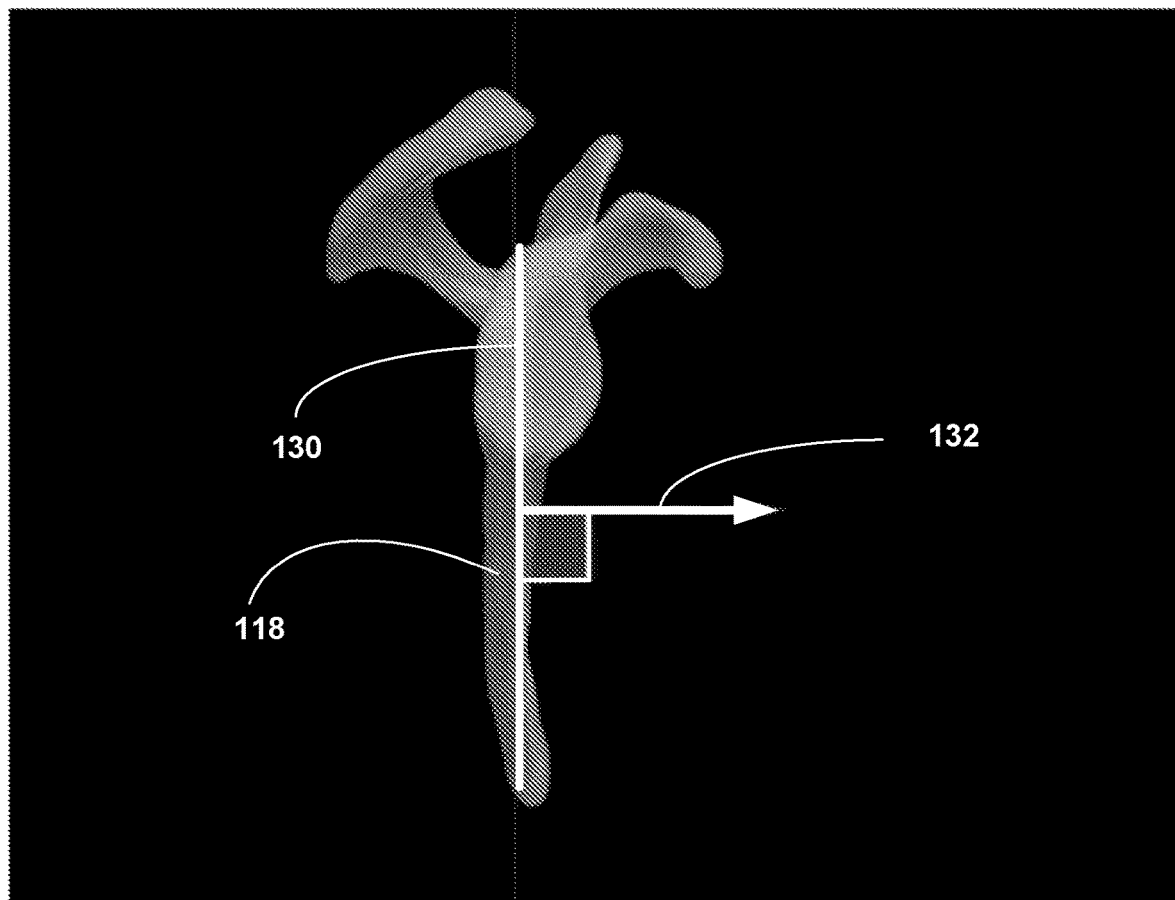
FIG. 4 is a conceptual diagram of a perspective view of a normal line to a plane through a scapula for determining a coordinate system of a patient.

FIG. 4 is a conceptual diagram of a perspective view of a normal line to a plane, as determined with the example illustrated in FIGS. 3A and 3B, through a scapula for determining a coordinate system of a patient. For instance, FIG. 4 illustrates plane 130. Plane 130 intersects line 128 illustrated in FIG. 3B. Plane 130 may be considered as the best fit plane to the body of scapula 118. Processing circuitry 102 may determine vector 132 that is normal to plane 130. In one or more examples, vector 132 may form one axis (e.g., x-axis) of the patient coordinate system. Techniques to determine the other axes is described in more detail below.

Figure 5:
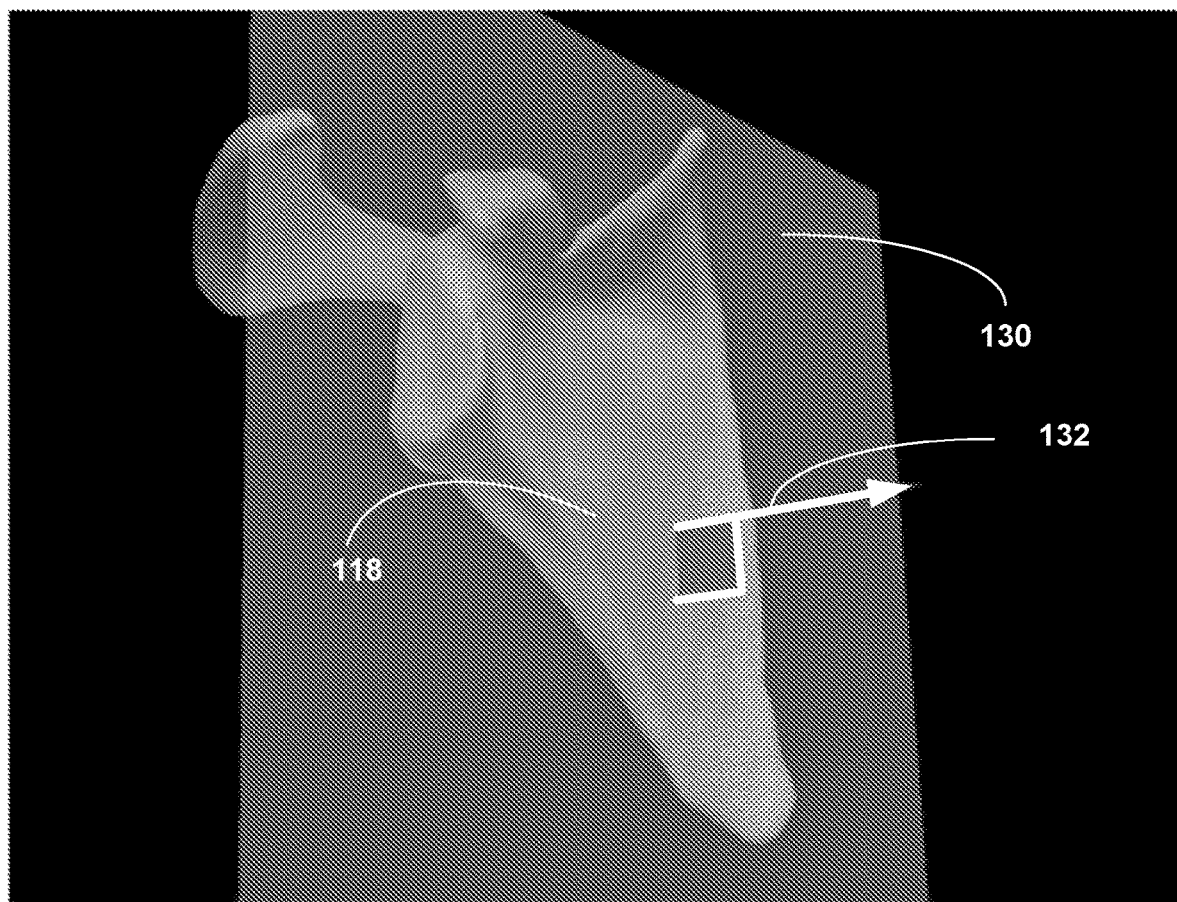
FIG. 5 is a conceptual diagram of another perspective view of a normal line to a plane through a scapula for determining a coordinate system of a patient.

FIG. 5 is a conceptual diagram of another perspective view of the example of FIG. 4 such as another perspective view of a normal line to a plane through a scapula for determining a coordinate system of a patient. FIG. 5 is similar to FIG. 4 but from a front perspective rather than the side perspective of FIG. 4. For example, FIG. 5 illustrates scapula 118 of the patient with the best fit plane 130 and the normal vector 132.

In this manner, processing circuitry 102 may determine a first axis of the patient coordinate system that is normal to scapula 118. Processing circuitry 102 may determine a second axis of the patient coordinate system as an axis that is transverse through scapula 118.

Figure 6:
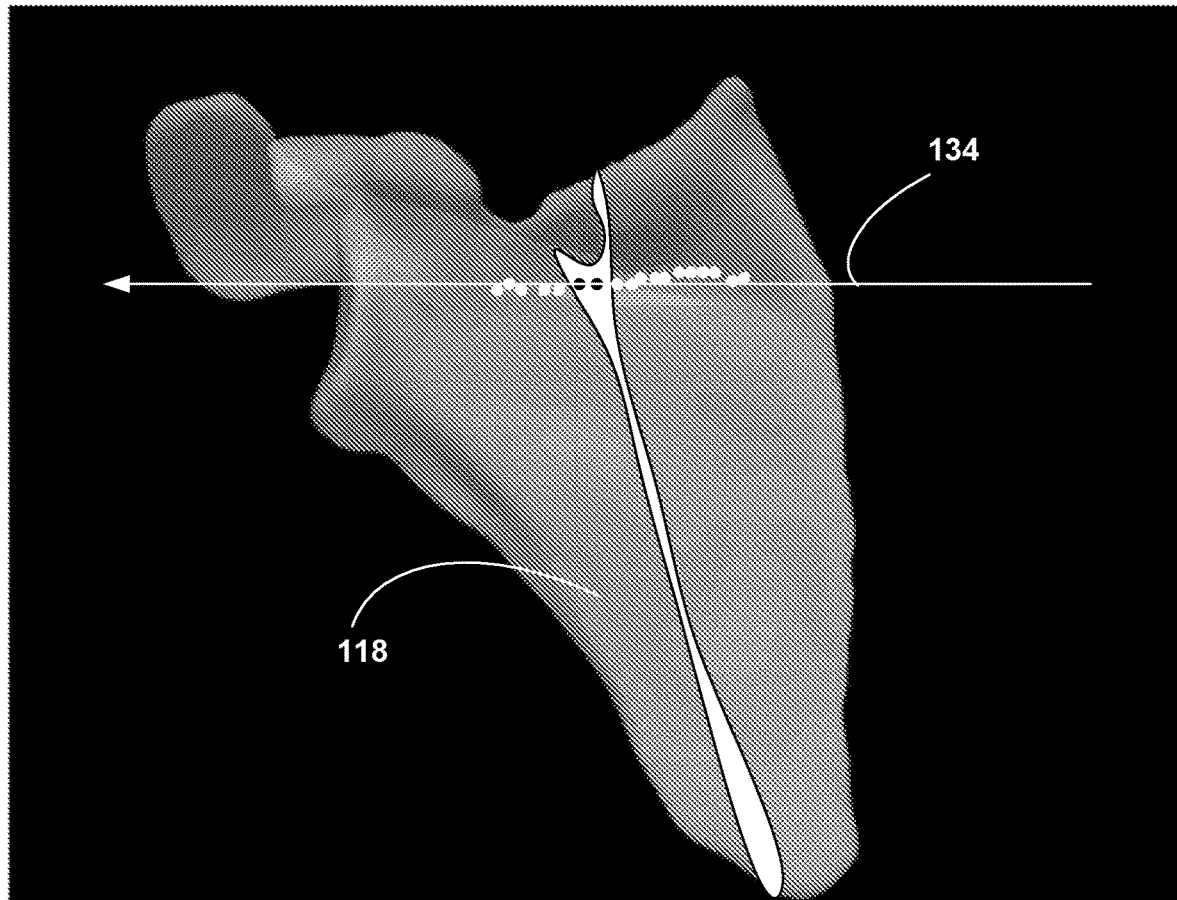
FIG. 6 is a conceptual diagram illustrating a transverse axis through a scapula for determining a coordinate system of a patient.

FIG. 6 is a conceptual diagram illustrating a transverse axis through a scapula for determining a coordinate system of a patient. For instance, FIG. 6 illustrates example to determine an axis, in addition to the one determined in FIGS. 4 and 5, for aligning shape model 106 to coordinate system of the image data of scans 108.

Figure 7B:
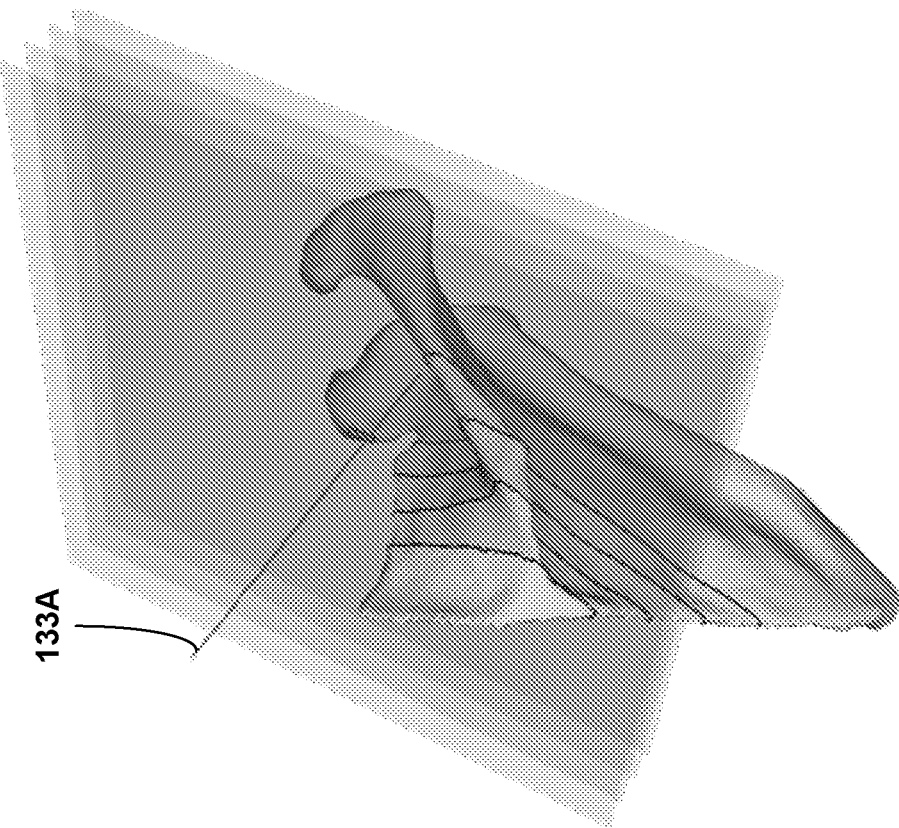
FIGS. 7A and 7B are conceptual diagrams illustrating an example of sagittal cuts through a scapula for determining the transverse axis of FIG. 6.
Figure 7A:
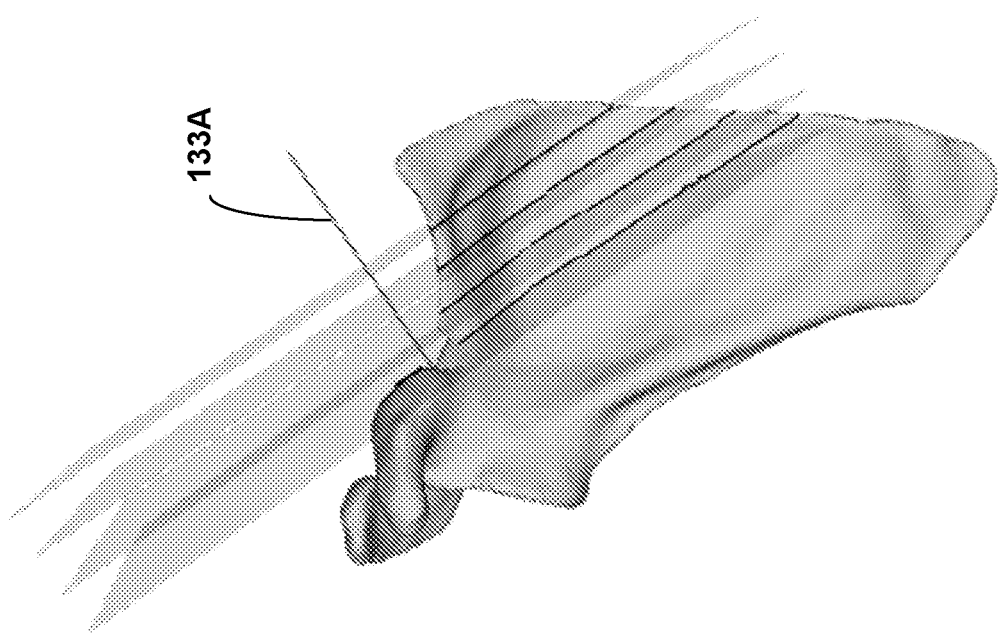

FIG. 6 illustrates transverse axis 134. Processing circuitry 102 may determine transverse axis 134 as a line that fits through the spongious region that lies between the supraspinatus fossa, the spine, and the scapula body. The example techniques to determine transverse axis 134 is described with respect to FIGS. 7A, 7B, FIGS. 8A-8C, and FIGS. 9A and 9B, and. Processing circuitry 102 may determine plurality of sagittal cuts through the scapula based on the image data of scan 108 as illustrated in FIGS. 7A and 7B. For instance, FIGS. 7A and 7B are different perspectives of sagittal cuts through scapula based on axis 133A. Processing circuitry 102 may utilize axis 133A based on an approximation of the spongious region that lies between supraspinatus fossa, the spine, and the scapula body, and may be pre-programmed with the estimated axis.

Figure 8C:
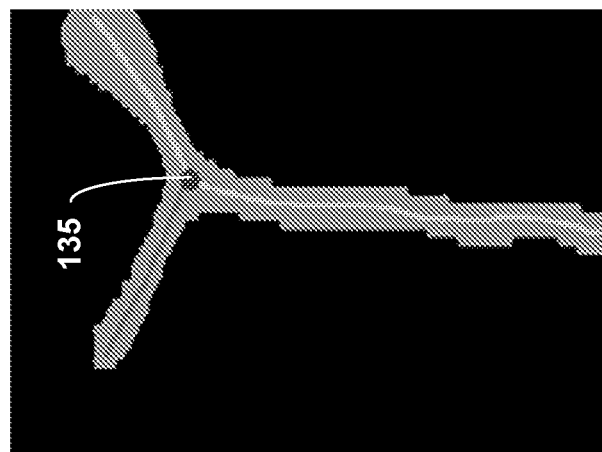
FIGS. 8A-8C are conceptual diagrams illustrating results of sagittal cuts through scapula for determining the transverse axis of FIG. 6.
Figure 8B:
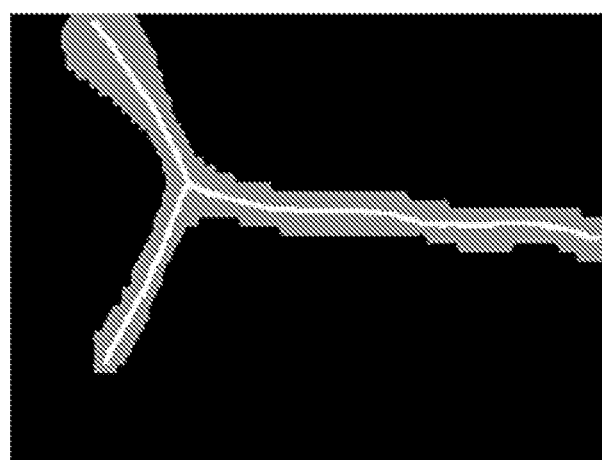
Figure 8A:

FIGS. 8A-8C illustrate the result of one of the sagittal cuts of the FIGS. 7A and 7B. For instance, the sagittal cuts from a "Y" shape, as illustrated in FIG. 8A. Processing circuitry 102 may determine a skeleton line through the Y shape, as illustrated in FIG. 8B. For instance, processing circuitry 102 may determine dots that are equidistant to nearest border through the Y shape and interconnect the dots to form the line through Y shape as shown in FIG. 8B. Again, rather than skeleton, other points may be used like center points. Processing circuitry 102 may determine an intersection of the lines through the skeleton, as illustrated by intersection point 135. For instance, intersection point 135 may be common to all of the lines that together form the Y shape.

Processing circuitry 102 may repeat these operations for each of the Y shapes in each of the sagittal cuts, and determine respective intersection points, like intersection point 135. Processing circuitry 102 may determine a line that that intersects the plurality of the respective intersection points to determine an initial transverse axis 133B illustrated in FIGS. 9A and 9B.

Figures 9A, 9B:
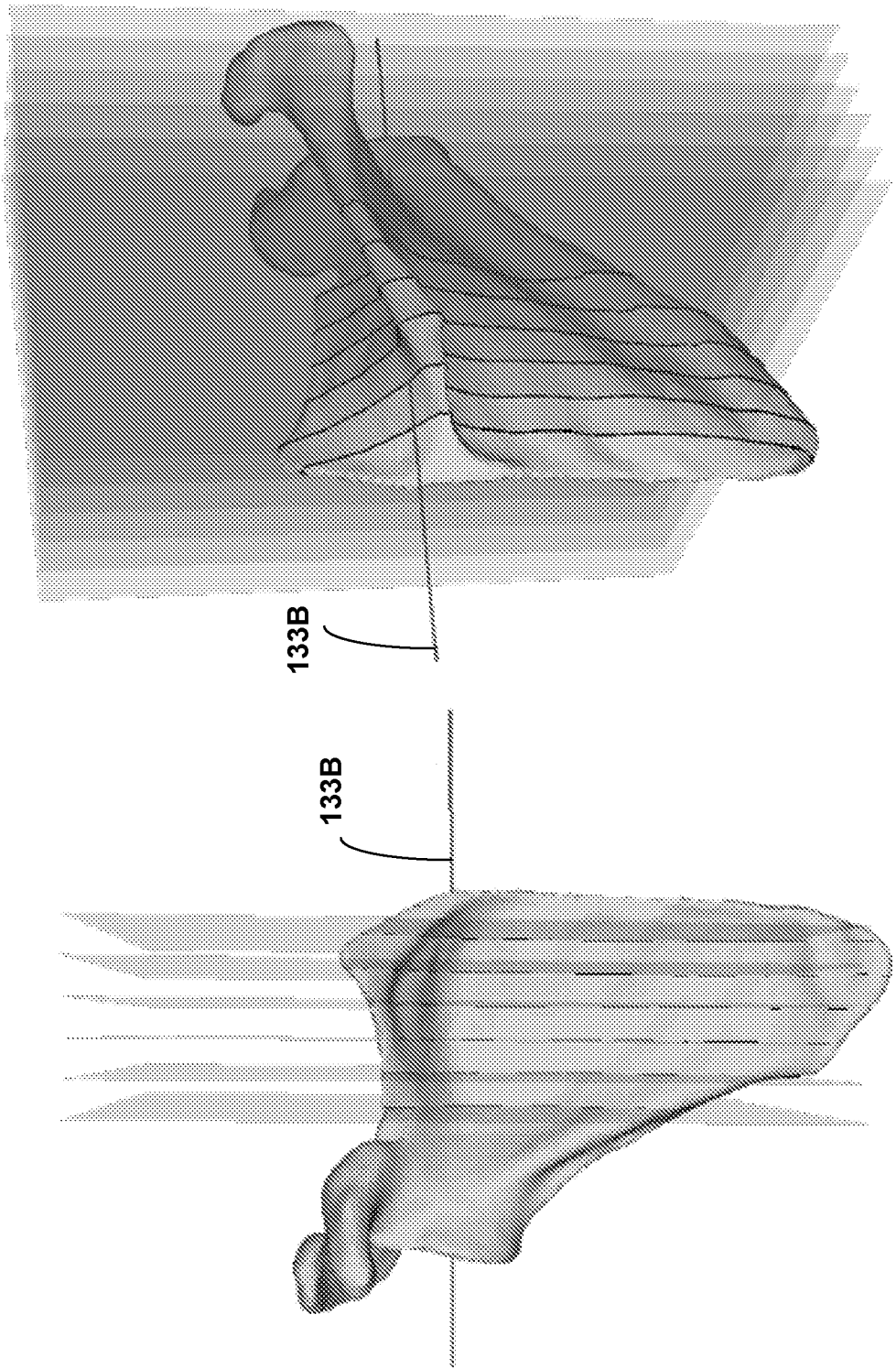
FIGS. 9A and 9B are conceptual diagrams illustrating another example of sagittal cuts through a scapula for determining the transverse axis of FIG. 6.

Processing circuitry 102 may determine sagittal cuts through the scapula using the initial transverse axis 133B. For instance, FIGS. 9A and 9B are different perspectives of sagittal cuts through scapula based on axis 133B. Processing circuitry 102 may repeat the operations described with respect to FIGS. 8A-8C to determine a plurality of intersection points for the sagittal cuts shown in FIGS. 9A and 9B. For example, similar to FIGS. 8A-8C, based on the sagittal cuts using axis 133B, each sagittal cut may form Y shapes, similar to FIG. 8A. Processing circuitry 102 may determine a skeleton line through the Y shapes, similar to FIG. 8B, and determine intersection points similar to FIG. 8C. Processing circuitry 102 may repeat these operations for each of the Y shapes in each of the sagittal cuts, and determine respective intersection points, similar to the description above for FIGS. 8A-8C. Processing circuitry 102 may determine a line that that intersects the plurality of the respective intersection points to determine transverse axis 134 illustrated in FIG. 6.

Figure 10:
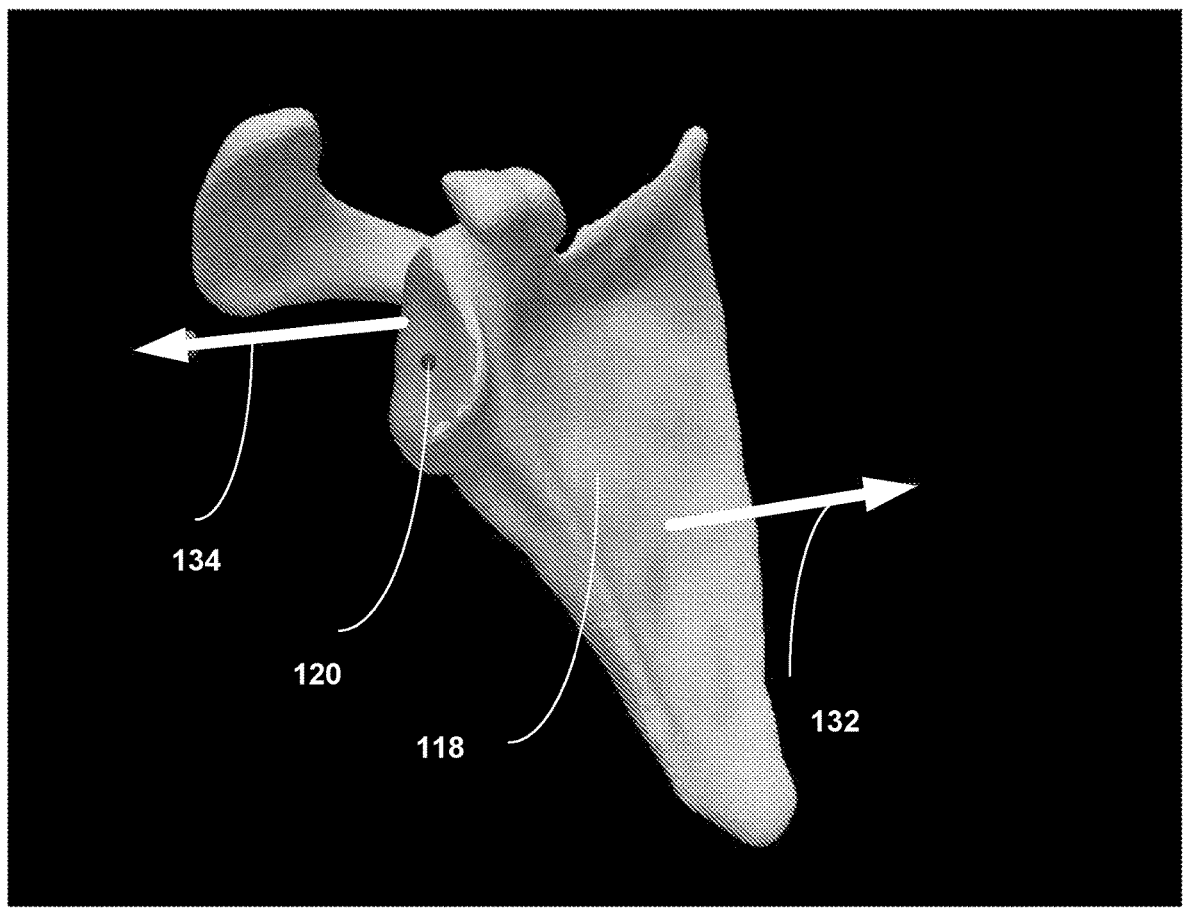
FIG. 10 is a conceptual diagram illustrating a transverse axis through a scapula and a normal line to a plane through the scapula for determining a coordinate system of a patient.

FIG. 10 is a conceptual diagram illustrating a transverse axis of FIG. 6 through a scapula and a normal line of FIGS. 4 and 5 to a plane through the scapula for determining a coordinate system of a patient. For example, FIG. 10 illustrates scapula 118 and glenoid center 120. FIG. 10 also illustrates vector 132 that is normal to plane 130 and illustrates transverse axis 134.

For example, as described above, an initial step for pre-morbid characterization is to determine a coordinate axis with which the segmented objects are aligned to shape model 106. With the example techniques described above, processing circuitry 102 may determine the x-axis (e.g., vector 132) and the z-axis (e.g., transverse axis 134). Processing circuitry 102 may further determine the y-axis using the below techniques. Once process circuitry 102 determines the coordinate system to represent and define location of anatomical objects determined from the segmentation of the image data of scans 108, processing circuitry 102 may be able to align the segmented object to the coordinate system of shape model 106.

Figure 11:
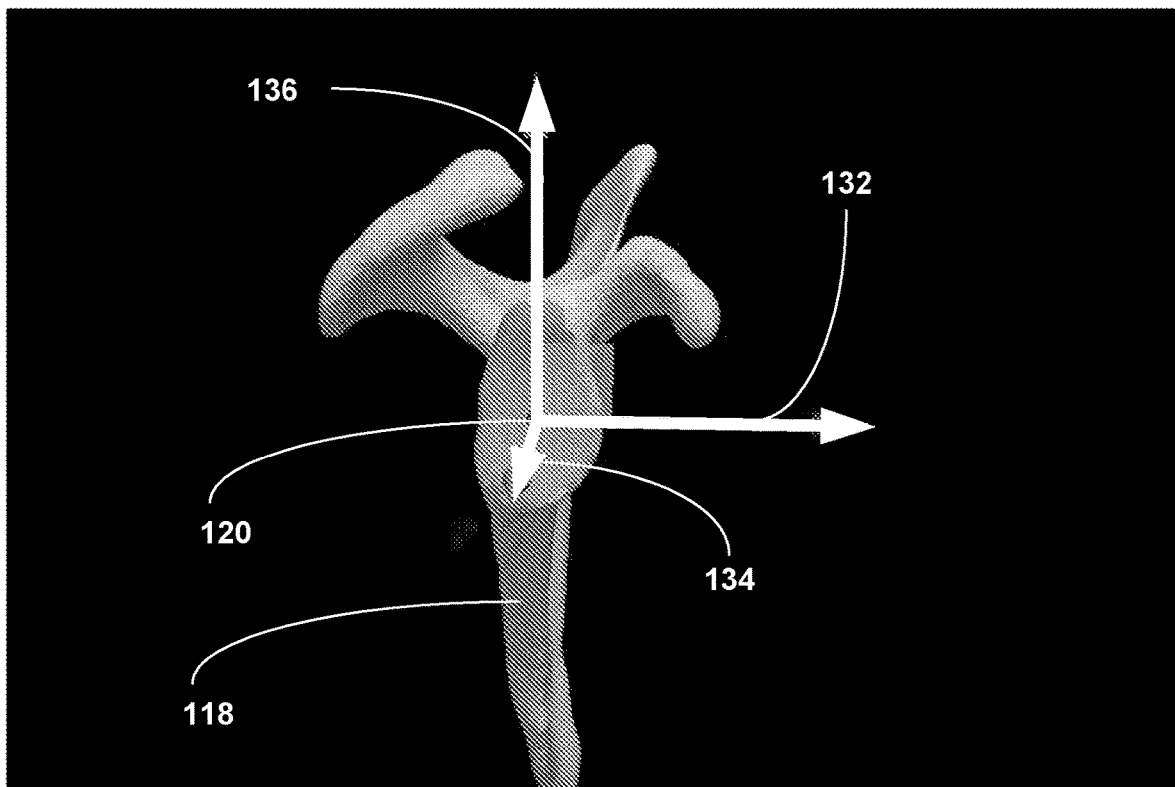
FIG. 11 is a conceptual diagram illustrating movement of a transverse axis through a scapula and a normal line to a plane through the scapula to a central location of a glenoid for determining a coordinate system of a patient.

FIG. 11 is a conceptual diagram illustrating movement (or extension) of a transverse axis through a scapula and a normal line to a plane through the scapula to a central location of a glenoid for determining a coordinate system of a patient. For instance, FIG. 8 illustrates the patient coordinate system centered around glenoid center 120. As illustrated, vector 132, as determined above, forms the x-axis of the patient coordinate system, transverse axis 134 forms the z-axis of the patient coordinate system, and axis 136 forms the y-axis of the patient coordinate system.

Processing circuitry 102 may determine a glenoid center based on a plurality of 2D and 3D operations. For example, processing circuitry 102 may determine a barycenter of the glenoid cavity and project the barycenter back to the glenoid cavity surface to determine glenoid center 120.

Processing circuitry 102 may then determine y-axis 136 based on x-axis 132, and z-axis 134. For example, processing circuitry 102 may determine y'=z*x, where * is the vector product. The y' is perpendicular to the plane defined by the x-axis 132 and the z-axis 134, but x-axis 132 and z-axis 134 need not necessarily be perfectly orthogonal. Accordingly, processing circuitry 102 may replace z-axis 134 by Z=x*y' or x-axis 132 by X=y'*z to have an orthogonal system (x, y', Z) or (X, y', z). In some examples, processing circuitry 102 may utilize Z=x*y' because the computation of x-axis 132 (e.g., the scapula normal) is more robust than the computation of z-axis 134 (e.g., transverse axis).

In this manner, processing circuitry 102 may determine the patient coordinate system. In some examples, such as those described above, processing circuitry 102 may determine the patient coordinate system without relying upon specific landmarks such as trigonum scapulae 122 and angulus inferior 124 that may not be present in segmentation of anatomical objects from the image data of scans 108 due to over or under segmentation. In particular, the example technique determine x, y, and z-axis without relying on specific anatomical objects, but rather, determine the x, y, and z-axis based on scapula 118 itself, which should be present in the image data of scans 108, whereas trigonum scapulae 122 and angulus inferior 124 may not be present in the image data of scans 108 due to under- or over-segmentation.

Figure 12:
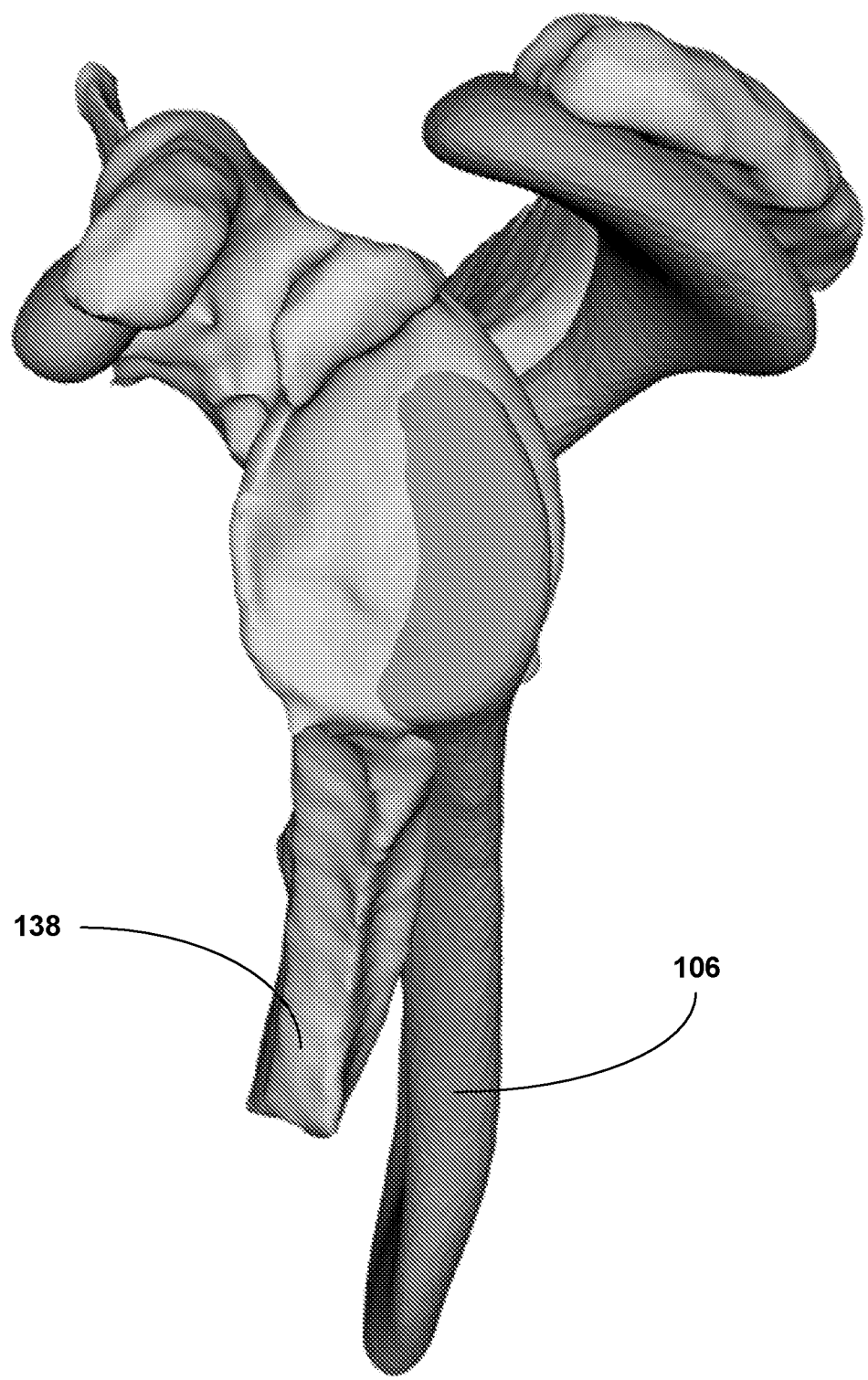
FIG. 12 is a conceptual diagram illustrating an example of an initial alignment of a segmentation object to a shape model.

After determining the patient coordinate system, processing circuitry 102 may determine the transformation matrix to align the patient coordinate system to shape model 106. As described above, one example way to determine the transformation matrix is using the coordinate system where c=(x,y,z,o), and where x, y and z are the orthogonal basis 3D vectors and o is the origin (c is a 4×4 homogeneous matrix with the last raw is (0,0,0,1)). The new coordinate system to which the segmented object is to be transformed is C=(X, Y,Z,O). In this example, the transformation matrix is then: T=c^−1×C Processing circuitry 102 may multiply the coordinates that define the segmentation object (e.g., where the coordinates are determined from the axes utilizing techniques described above) based on the image data from scans 108 with the transformation matrix to align the segmentation objects to shape model 106 (e.g., the SSM retrieved from memory 104). The result of this alignment may be an initial shape. For example, FIG. 12 illustrates initial aligned shape 138 that is aligned with shape model 106. Initial aligned shape 138 is shown as superimposed on shape model 106, in FIG. 12. Initial aligned shape 138 is generated based on the image data of scans 108 where certain portions of the anatomy may be missing (e.g., due to under-segmentation) or distorted (e.g., due to over-segmentation). For instance, initial aligned shape 138 may be generally positioned such that it has the same orientation on the x-, y-, and z-axis as shape model 106.

However, following transformation, initial aligned shape 138 may not be as closely aligned with shape model 106. In case the scapula is over-truncated inferiorly and/or medially (which may not be known but is the case in initial shape 138), there could be computational errors in determining the scapula body normal (e.g., vector 132) and the transverse axis 134. These computational errors may lead to misalignment between the shape model 106 and the patient anatomy (e.g., scapula 118), and therefore, initial aligned shape 138 may not be as closely aligned with shape model 106 as desirable. For example, as can be seen from FIG. 12, initial aligned shape 138 is rotated along z-axis (e.g., transverse axis) 134.

In one or more examples, because it may be unknown whether there is misalignment from over-truncated scapular 118, processing circuitry 102 may modify parameters of initial shape 138 to generate an aligned shape. The aligned shape is substantially proximal (e.g., in location, size, and orientation) to shape model 106. As one example, to modify parameters, processing circuitry 102 may iteratively adjust coordinates of initial aligned shape 138 so that the initial aligned shape model rotates along the z-axis (e.g., the points of initial aligned shape 138 rotate along the z-axis). At each adjustment, processing circuitry 102 may determine a distance between the initial aligned shape 138 and shape model 106 (e.g., points in the initial aligned shape and points represented in shape model 106).

For instance, processing circuitry 102 may determine the distances between points on initial aligned shape 138 (e.g., such as points of acromion and the coracoid) and corresponding points on shape model 106 (e.g., acromion and coracoid on shape model 106). The corresponding points refer to points in the initial aligned shape 138 and points in shape model 106 that identify the same patient anatomy. Processing circuitry 102 may keep rotating the initial aligned shape 138 until the distance between the initial aligned shape 138 and shape model 106 about the z-axis 134 satisfies a threshold (e.g., less than threshold including where distance is minimized). Then, processing circuitry 102 may rotate the initial aligned shape 138 along the y-axis 138 until the difference in points between initial aligned shape 138 and corresponding points in shape model 106 about the y-axis satisfies a threshold (e.g., less than threshold including where distance is minimized). Processing circuitry 102 may rotate the initial aligned shape model about the x-axis 132 until the difference in points between initial aligned shape 138 and corresponding points in shape model 106 along the x-axis 132 satisfies a threshold (e.g., less than threshold including where distance is minimized).

As one example, processing circuitry 102 may modify the parameters of the initial aligned shape 138 so that the initial aligned shape 138 rotates 5-degrees along an axis (e.g., a first instance of the initial aligned shape model) within a search range of [−45-degrees, 45-degrees] or [−27 degrees, 27 degrees]. Processing circuitry 102 may determine the distance between points of the first instance of the initial aligned shape 138 and corresponding points of shape model 106. Assuming the distance is not at a minimum or less than threshold, next, processing circuitry 102 may modify the parameters of the initial aligned shape 138 so that the initial aligned shape rotates 10-degrees along the axis (e.g., a second instance of the initial aligned shape 138) and determine the distance (e.g., between points of the second instance of the initial aligned shape 138 and corresponding points of shape model 106). Processing circuitry 102 may repeat these operations about each of the axes for each instance of the initial aligned shape 138. Processing circuitry 102 may keep repeating these operations until processing circuitry 102 determines an instance of the initial aligned shape 138 that resulted in a distance less than a threshold (such as the minimum distance). The instance of the initial aligned shape 138 that resulted in the distance being less than threshold (including example of minimum distance) among the various iterative instances is selected as aligned shape 140, illustrated in FIG. 13.

Figure 13:
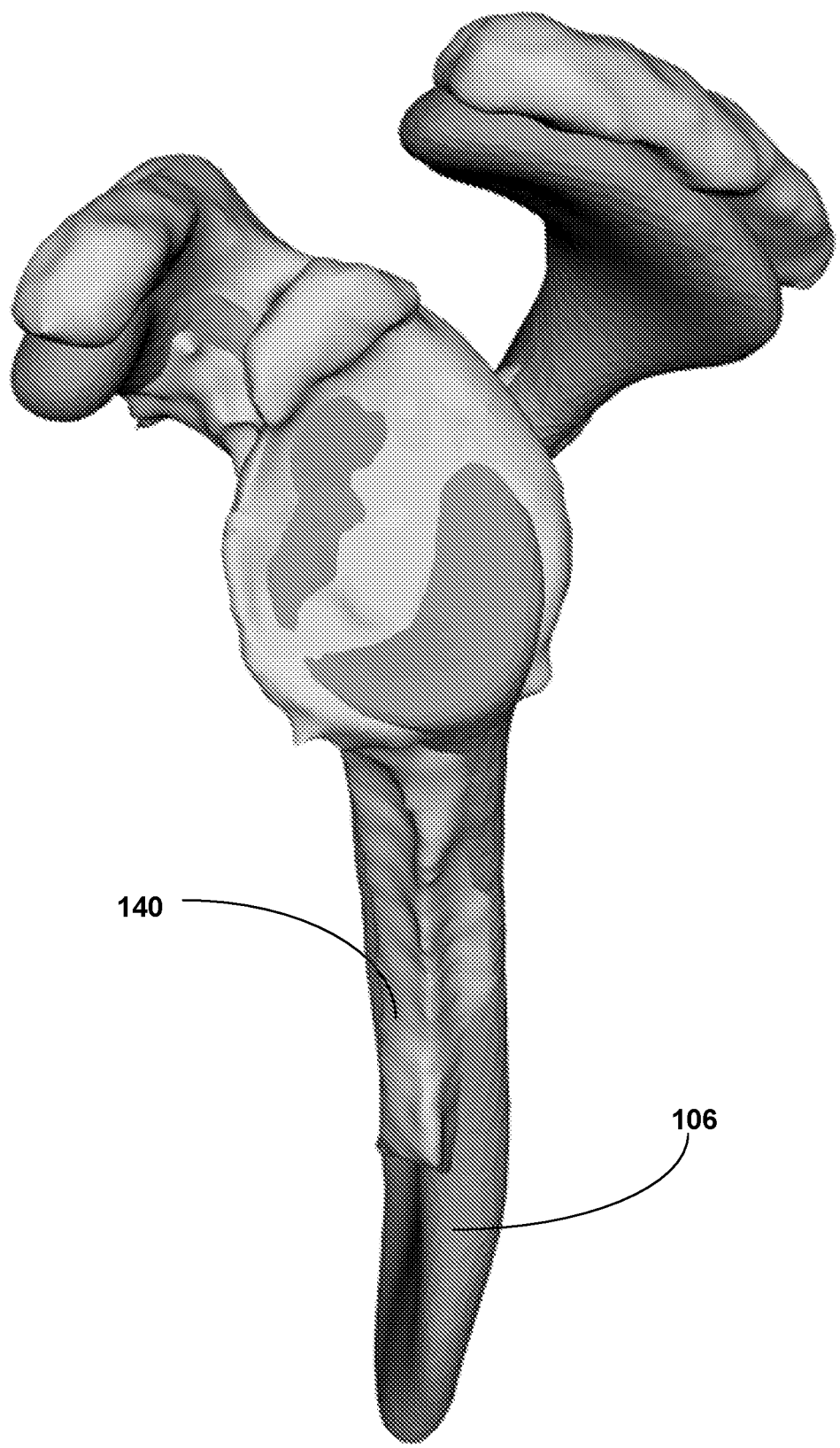
FIG. 13 is a conceptual diagram illustrating an example of an intermediate alignment of a segmentation object to a shape model.

The result of these operations may be the aligned shape (e.g., a model that has been rotated along the x, y, and z-axes). For example, FIG. 13 illustrates aligned shape 140 that is aligned to shape model 106. Aligned shape 140 is shown as superimposed on shape model 106, in FIG. 13. Aligned shape 140 (e.g., simply aligned shape 140) provides a better alignment to shape model 106 as compared to initial aligned shape 138. For instance, as shown in FIG. 13, aligned shape 140 is better aligned to shape model 106 than initial aligned shape 138 to shape model 106, as shown in FIG. 12.

For instance, initial aligned shape 138 and shape model 106 may be generally aligned. However, there may be some tilting or misorientation between the initial aligned shape 138 and shape model 106 due to the over or under segmentation of the image data of anatomical objects in scans 108. To address this, processing circuitry 102 may separately rotate initial aligned shape 138 about each axis (x, y, z) until the distance between initial aligned shape 138 and shape model 106 satisfies a threshold (e.g., minimized). Accordingly, by iteratively rotating initial aligned shape 138, processing circuitry 102 may generate aligned shape 140 (also called intermediate aligned shape 140). Because the distance between points on aligned shape 140 and corresponding points of shape model 106 may be minimized, aligned shape 140 (e.g., intermediate aligned shape 140) is substantially in the coordinate system of shape model 106.

Aligned shape 140 may be referred to as an intermediate aligned shape because in some examples, shape model 106 is deformed to the shape of aligned shape 140 to generate the pre-morbid characteristics of the patient anatomy. Processing circuitry 102 may utilize techniques described below to deform shape model 106 to register shape model 106 to aligned shape 140. However, in some examples, processing circuitry 102 may utilize some other techniques to deform shape model 106 to register to aligned shape 140. Also, for the example techniques to register shape model 106 to aligned shape 140, it may be possible that such techniques are preformed where aligned shape 140 is generated using techniques other than those described above.

As described above, processing circuitry 102 may be configured to register shape model 106 to aligned shape 140. Registering shape model 106 to aligned shape 140 may refer to iteratively deforming shape model 106 until a cost function value is below a threshold (e.g., minimized). The registering algorithm is a global loop that includes two inner iterative loops referred to as iterative closest point (ICP) loop and elastic registration (ER) loop. There may be other example ways in which to perform the registering algorithm, and the use of two loops within a global loop is just one example way in which to perform the registering algorithm. For instance, in some examples, it may be possible to bypass the ICP loop and only perform the ER loop. In some examples, it may be possible to perform only the ICP loop and bypass the ER loop.

In the ICP loop for the first iteration of the global loop, the initial input is aligned shape 140 and shape model 106. For the ICP loop in the first iteration of the global loop, processing circuitry 102 iteratively modifies aligned shape 140 based on a comparison of aligned shape 140 to shape model 106 to generate a first order shape. For example, for each iteration through the ICP loop, processing circuitry 102 determines a cost value, and the modified aligned shape that results in the cost value less than a threshold (e.g., minimized) is the output of the ICP loop and is referred to a first order shape. An example of the ICP algorithm is described in more detail below.

The first order shape is an input into the ER loop for the first iteration of the global loop. Another input into the ER loop, for the first iteration of the global loop, is shape model 106. For the ER loop in the first iteration of the global loop, processing circuitry 102 may deform shape model 106 to generate a plurality of estimated shape models (e.g., one for each time through the ER loop). For each loop of the ER loop, processing circuitry 102 may determine a total cost value, and determine which iteration of the ER loop utilized the estimated shape model having the total cost value that satisfies the threshold (e.g., less than threshold including where minimized). The result of the ER loop (e.g., the estimated shape model having the total cost value that satisfies the threshold) is a first order registered shape model. This completes one iteration of the global loop. The total cost value, for the first iteration of the global loop, may be based on distances and orientation between the estimated shape models and the first order shape, constraints on medialization of anatomy, and parameter weighting.

For example, assume that S1 is the first order shape model that processing circuitry 102 is to determine using the ER loop in the first iteration of the global loop. For the ER loop, processing circuitry 102 may generate S11, S12, S13, and so forth, where each one of S11, S12, S13, and so forth is a deformed version of shape model 106 and S11, S12, S13, and so forth are each an example of an estimated shape model. For each of one of S11, S12, S13, and so forth, processing circuitry 102 may determine a total cost value (e.g., S11 total cost value, S12 total cost value, S13 total cost value, and so forth). Processing circuitry 102 may determine which of the total cost values is the less than a threshold (e.g., minimized). The estimated shape model (e.g., one of S11, S12, S13, and so forth) having the total cost value that is below a threshold (e.g., minimized) is S1 (e.g., the first order registered shape model). After this, the first iteration of the global loop is complete.

For the second iteration of the global loop, processing circuitry 102 performs the operations of the ICP loop. In the second iteration of the global loop, for the ICP loop, one input is the first order shape model, generated from the ER loop, and the other input is the first order shape, generated by the previous ICP loop. In the second iteration of the global loop, for the ICP loop, processing circuitry 102 iteratively modifies the first order shape based on a comparison of the first order shape to the first order shape model. For instance, for each iteration through the ICP loop, processing circuitry 102 determines a cost value, and the modified first order shape that results in the cost value less than a threshold (e.g., minimized) is the output of the ICP loop and is referred to a second order shape.

The second order shape is an input into the ER loop for the second iteration of the global loop. Another input into the ER loop, for the second iteration of the global loop, is shape model 106 and/or the first order shape model. Where shape model 106 is used, the values of $b_i$ may range within [−b+b]. Where the first order shape model is used, the values of $b_i$ may range within [−b+b_prev b+b_prev], where b_prev is the value found in the previous iteration (e.g., used to determine the first order shape model).

For the ER loop in the second iteration of the global loop, processing circuitry 102 may deform shape model 106 and/or the first order shape model to generate a plurality of estimated shape models (e.g., one for each iteration of the ER loop). For each iteration of the ER loop, processing circuitry 102 may determine a total cost value, and determine which iteration of the ER loop utilized the estimated shape model having the total cost value that satisfies the threshold (e.g., minimized). The result of the ER loop, in the second iteration of the global loop, (e.g., the estimated shape model having the total cost value that satisfies the threshold) is a second order shape model. This completes a second iteration of the global loop. The total cost value, for the second iteration of the global loop, may be based on distances and orientation between the estimated shape models and the second order shape, constraints on medialization of anatomy, and parameter weighting.

For example, assume that S2 is the second order shape model that processing circuitry 102 is to determine using the ER loop in the second iteration of the global loop. For the ER loop, processing circuitry 102 may generate S21, S22, S23, and so forth, where each one of S21, S22, S23, and so forth is a deformed version of shape model 106 and/or the first shape model and S21, S22, S23, and so forth are each an example of an estimated shape model. For each of one of S21, S22, S23, and so forth, processing circuitry 102 may determine a total cost value (e.g., S21 total cost value, S22 total cost value, S23 total cost value, and so forth). Processing circuitry 102 may determine which of the total cost values is the less than a threshold (e.g., minimized). The estimated shape model (e.g., one of S21, S22, S23, and so forth) having the total cost value that is below a threshold (e.g., minimized) is S2 (e.g., the second order registered shape model). After this, the second iteration of the global loop is complete.

In the above example, processing circuitry 102 generated S11, S12, S13, and so forth (e.g., first set of estimated shape models) for the first iteration of the global loop and generated S21, S22, S23, and so forth (e.g., second set of estimated shape models) for the second iteration of the global loop. In some examples, the number of estimated shape models in the first and second set of estimated shape models may be the same. In some examples, the number of estimated shape models in the first and second set of estimated shape models may be different (e.g., 6 estimated shape models in the first set of estimated shape models and 14 estimated shape models in the second set of estimated shape models). One reason for having different numbers of estimated shape models in different iterations of the global loop is that by increasing the number of estimated shape models in subsequent iterations of the global loop, it may be possible to more accurately determine a global minimum as compared to if the same or fewer number of estimated shape models is used. That is, processing circuitry 102 may gradually increase the number of unknowns (e.g., modes and scale factors) used to generate the estimated shape models through multiple ER loops.

This process keeps repeating until the total cost value is below a threshold (e.g., minimized). The registered shape model (e.g., $N^{th}$ order registered shape model) that provides the total cost value below a threshold (e.g., minimized) provides a pre-morbid characterization of the patient anatomy. Some additional processing may be needed to bring back the pre-morbid characterization into the patient coordinate system.

As described above, for determining the pre-morbid characterization, there is a global loop that includes an ICP loop and an ER loop. The following describes an example of the ICP loop. In the ICP loop, there is a source point clout and a target point cloud. The target point cloud remains fixed and processing circuitry 102 modifies (e.g., transforms) the source point cloud such that the transformed point cloud matches the target point cloud. A difference between the transformed point cloud and the target point cloud indicates how well of a match the transformed point cloud is to the source cloud. In one or more examples, processing circuitry 102 keeps transforming the source point cloud until the difference is below a threshold. For instance, processing circuitry 102 keeps transforming the source point cloud until the difference is minimized.

In one or more examples, in the first iteration of the global loop, for the ICP loop, the target point cloud is shape model 106 and the source point cloud is aligned shape 140. Processing circuitry 102 may determine distances between points on aligned shape 140 and corresponding points on shape model 106. The points on aligned shape 140 that are used may be points that are known not be pathological (e.g., medial glenoid vault, the acromion, and the coracoid, as a few non-limiting examples). Other examples include various other points on the scapula that are present in the image data of scans 108. Processing circuitry 102 may find points for the same anatomy on shape model 106.

Figure 14:
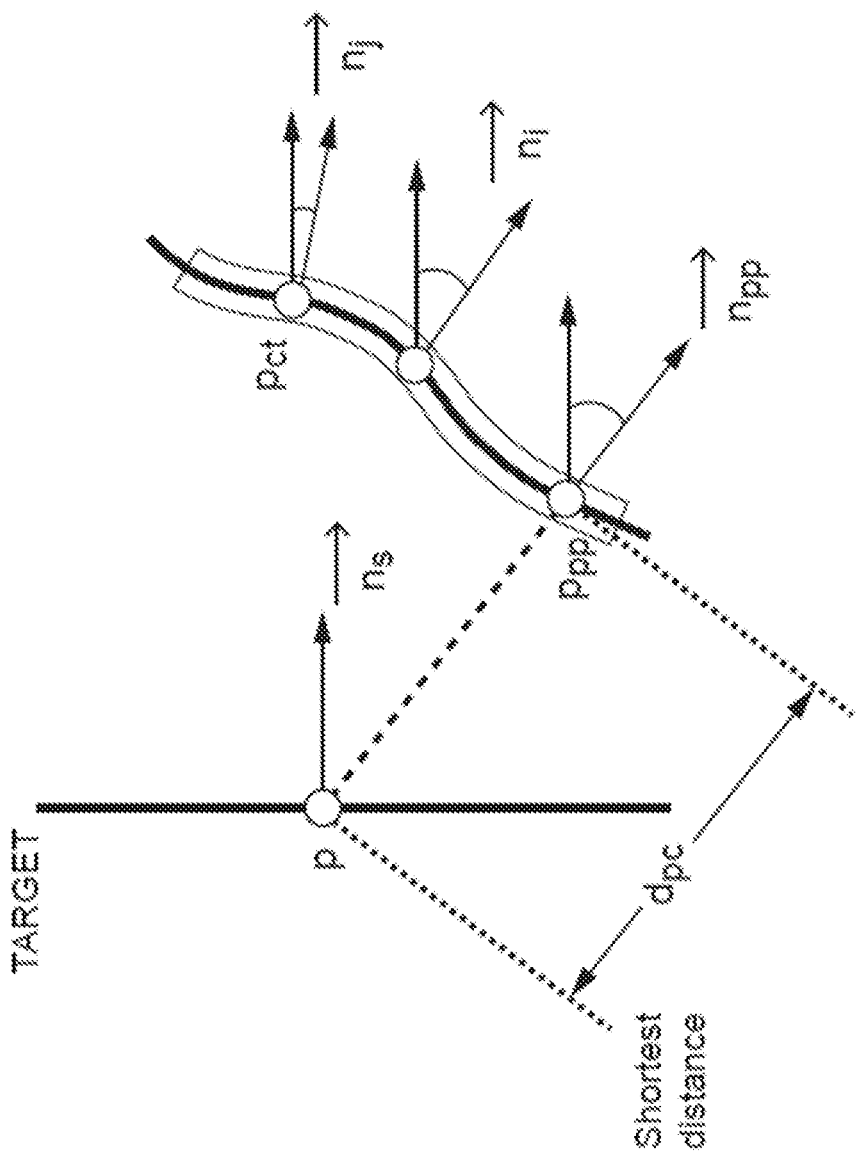
FIG. 14 is a conceptual diagram illustrating an example for determining difference values for iterative closest point (ICP) algorithm.

FIG. 14 is a conceptual diagram illustrating an example for determining difference values for ICP algorithm. For example, processing circuitry 102 may determine a point (p) on target point cloud (e.g., shape model 106). Processing circuitry 102 may then determine closest point to point p on aligned shape 140, which in the example of FIG. 14 is point $p_{pp}$. Processing circuitry 102 may determine a set number of points (e.g., 10 points) that are proximate to point $p_{pp}$ on aligned shape 140 such as pa, illustrated in FIG. 14.

For point p on shape model 106 and each of these points (e.g., closest point and proximate points on aligned shape 140), processing circuitry 102 may determine a normal vector. For example, vector ns is the normal vector for point p, vector $n_{pp}$ is the normal vector for point $p_{pp}$, and vector nj is the normal vector for point $p_{ct}$. One way to determine the normal vectors is based on vectors orthogonal to a tangential plane to the point. Another way to compute a point's normal is to calculate the normal of each triangle that shares that point and then attribute the mean normal. In order to overcome local noise, normals are smoothed by computing the mean normal of points within a specific vicinity.

Processing circuitry 102 may determine an orientation and distance difference between point p on shape model 106 and points on aligned shape 140 based on the following equation:

$$\text{Difference} = \text{norm}(p_s - p_t)^2 + w * \text{norm}(n_s - n_t)^2.$$

In the above equation, $p_s$ is a source point (e.g., point p on shape model 106), pt is point on aligned shape 140 (e.g., closest point and proximate points such as point $p_{pp}$ or $p_{ct}$), ns is the normal vector of point $p_s$ (e.g., ns as shown in FIG. 14), nt is the normal vector of point on aligned shape 140 (e.g., $n_{pp}$ and nj), and w is a pre-programmed weighting factor. Typically, w equals 1 to give equal weights between distance and orientation. In some examples, high/low curvature regions may require higher/lower values of 'w'. The value of 'w' may be defined empirically.

Processing circuitry 102 may determine which of the difference values resulted in the smallest different value. For example, assume that a first difference value is based on p, ns, $p_{pp}$, and $n_{pp}$ and a second difference value is based on p, ns, $p_{ct}$, and $n_j$. In this example, the second difference value may be smaller than the first difference value. Processing circuitry 102 may determine pa on aligned shape 140 as a corresponding point to point p on shape model 106.

Although FIG. 14 illustrates one point p on shape model 106, there may be plurality (e.g., N number) of points on shape model 106, and processing circuitry 102 may perform operations similar to those described above to identify N corresponding points on aligned shape 140 for each of the N points on shape model 106. Accordingly, there may be N difference values. Processing circuitry 102 may sum together the N difference values and divide the result by N. If the resulting value is greater than a threshold (e.g., including examples where the resulting value is not minimized), processing circuitry 102 may continue with the ICP loop.

With the N points on shape model 106 and the N points on aligned shape, processing circuitry 102 may determine a rotation matrix, R, and a translation vector, t. Based on the rotation matrix and the translation vector, processing circuitry 102 may rotate and translate the points on aligned shape 140 (e.g., −R multiplied by (points on aligned shape) plus translation vector). The result is a first intermediate first order shape. One example way of generating the rotation matrix R and the translation vector t is described in Berthold K. P. Horn (1987), "Closed-form solution of absolute orientation using unit quaternions," https://pdfs.semanticscholar.org/3120/a0e44d325c477397afcf94ea7f285a29684a.pdf.

This may conclude one instance of the ICP loop. Processing circuitry 102 may then repeat these operations where processing circuit 102 uses the first intermediate first order shape, in place of aligned shape 140, and shape model 106. Processing circuitry 102 may determine N difference values for each of the N points on shape model 106 and the N points on the intermediate first order shape. Processing circuitry 102 may sum together the N difference values and divide by N. If the resulting value is greater a threshold (or not minimized), processing circuitry 102 may determine the rotation matrix and the translation vector and determine a second intermediate first order shape. This may conclude a second iteration through the ICP loop.

Processing circuitry 102 may keep repeating these operations until processing circuitry 102 determines a value resulting from the sum of N difference values between the N points on shape model 106 and the N points on the Xth intermediate first order shape being divided by N where the value satisfies a threshold (such as when the value is minimized). In this case, the ICP loop is concluded and processing circuitry 102 determines that the Xth intermediate first order shape is the first order shape.

The first order shape becomes an input into the elastic registration (ER) loop. Another input in the ER loop is shape model 106. In the ER loop, processing circuitry 102 may determine a plurality of estimated shape models based on shape model 106. For instance, processing circuitry 102 may determine a new shape model ($s_i$) based on the following equation:

$$s_i = s' + \Sigma_i b_i \sqrt{\lambda_i} \times v_i.$$

In the above equation, s' is shape model 106 (e.g., point cloud of mean shape as one example, where point cloud defines coordinates of points within shape model 106, such as vertices of primitives that form shape model 106). In the equation, X4 is the eigenvalues and $v_i$ is the eigenvectors of the covariance matrix respectively (also called modes of variations). The covariance matrix represents the variance in a dataset. The element in the i, j position is the co-variance between the i-th and j-th elements of a dataset array.

Processing circuitry 102 may determine the plurality of estimated shape models by selecting different values of $b_i$. In the above, $b_i$ is a scaling factor to scale the eigenvalues or eigenvectors. The eigenvalue ($\lambda_i$) the eigenvector ($v_i$) are known from the generation of shape model 106 (e.g., s'). For ease of illustration, assume that processing circuitry 102 determined 10 estimated shape models based on 10 selected (e.g., randomly or pre-programmed) values of bi. There may be more or fewer than 10 estimated shape models.

In the ER loop, processing circuitry 102 may perform the following operations on the estimated shape models. As part of the ER loop, processing circuitry 102 may determine which of the estimated shape models produces a cost function value that is below a threshold (e.g., minimized). The cost function value may be based on three sub-cost function values, although more or fewer than the three sub-cost function values are possible. For example, assume that the first sub-cost function value is Cf1, the second sub-cost function value is Cf2, and the third sub-cost function value is Cf3. In some examples, the cost function value (Cf) is equal to Cf1+Cf2+Cf3. In some examples, weights may be applied, such that Cf=w1*Cf1+w2*Cf2+w3*Cf3, 0<wi<1 and 0≤Cfi≤1. The weights (wi) may be pre-programmed. To complete the ER loop, processing circuitry 102 may determine which of the estimated shape model generates a Cf value that satisfies a threshold (e.g., less than threshold including minimized).

A first sub-cost function value (Cf1) is based on distances and orientation between the estimated shape models (e.g., generated based on different values for bi) and the first order shape generated by the ICP loop. For instance, for each of the estimated shape models, processing circuitry 102 may determine a Cf1 value. The equation for Cf1 may the same as the equation used for the ICP loop.

For example, $Cf1=\Sigma norm(p_s-p_t)^2+w*norm(n_s-n_t)^2/N$. However, in this case, $p_s$ and $n_s$ are for points and vectors of those points on each of the estimated shape models, and $p_t$ and $n_t$ are for points and vectors of those point on the first order shape. N refers to the number of points on the first order shape and on each of the estimated shape models.

Processing circuitry 102 may determine the value for Cf1 using the above example techniques described for the ICP loop. For example, for a first estimated shape model, processing circuitry 102 may determine a value of Cf1 (e.g., first Cf1), for a second estimated shape model, processing circuitry 102 may determine a value for Cf1 (e.g., second Cf1), and so forth. In this case, processing circuitry 102 may not perform any translation or rotation of any of the estimated shape models but utilize the calculation of Cf1 for each of the estimated shape models to select one of the estimated shape models.

The value of Cf1 is one of the sub-cost function values used to determine the cost function value of the ER loop. In some examples, it may be possible to determine the estimated shape model that minimizes the Cf1 value and end the ER loop. However, simply minimizing the difference (e.g., distance of points) between the output of the ICP loop and the estimated shapes generated from shape model 106 may not be sufficient to determine the pre-morbid characterization of the patient anatomy. For example, there may be logical constraints on the location of the shape generated by the ICP loop (e.g., the first order shape after the initial conclusion of the ICP loop) relative to the patient's body and minimizing the difference (e.g., distances) between the first order shape and the estimated shapes may possibly violate such logical constraints. For example, the sub-cost function value, Cf1, can be non-convex for some cases and therefore may lead to a local minimum that is incorrect. With additional sub-cost function values, processing circuitry 102 may correct for the non-convexity of the total cost function value, Cf.

For example, when predicting the pre-morbid characterization of the glenoid, the glenoid of the estimated shape models should not be more medialized than the current patient glenoid. In this disclosure, medialized or medial means towards the center of the patient's body. When the patient suffers injury or disease at the glenoid, the bone erosion may cause the pathological glenoid to be more medial (e.g., shift closer to the middle of the patient's body) than prior to the injury or aliment. Therefore, a glenoid on an instance of one of the estimated shape models that is more medial than the current glenoid is more than likely not a proper estimate of the pre-morbid patient anatomy. Again, the injury or disease may have caused the glenoid to become more medial, and therefore, if one of the estimated shape models includes a glenoid that is more medial than the current position of the glenoid, the instance of the estimated shape model may not have the pre-morbid characteristics of the patient anatomy.

That is, assume that a first estimated shape model, generated from shape model 106, minimized the value of Cf1 based on distances and orientation between the first estimated shape model and the first order shape generated by the ICP loop. In this example, if the glenoid of the first estimated shape model is more medial than the current position of the glenoid, the first estimated shape model may not be the correct or best estimate of the pre-morbid shape of the pathological anatomy.

To ensure that medialized instances of the estimated shape models are not used to determine the pre-morbid characterization, processing circuitry 102 may determine the value of Cf2. The value of Cf2 indicates whether the estimated shape model is more or less medial than the patient anatomy. That is, a second example sub-cost function value is Cf2. The value of Cf2 is a measure of constraints on medialization of anatomy.

Figure 15A:
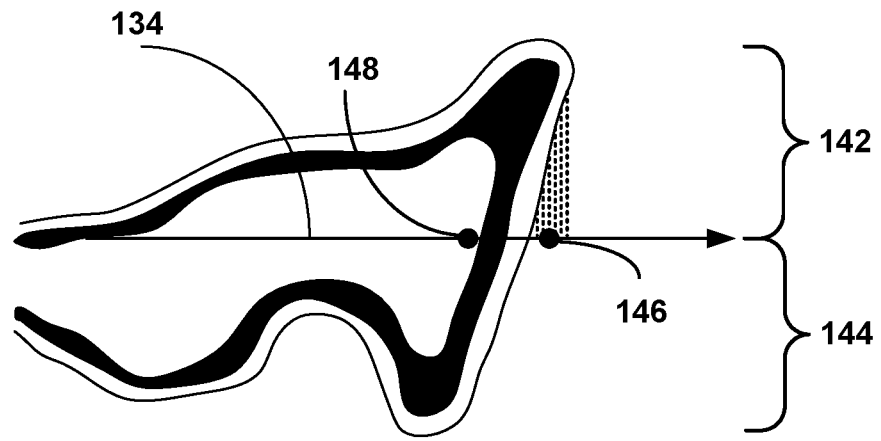
FIGS. 15A and 15B are conceptual diagrams illustrating portions of a glenoid for determining parameters of a cost function used to determine a pre-morbid shape of anatomy of a patient.
Figure 15B:
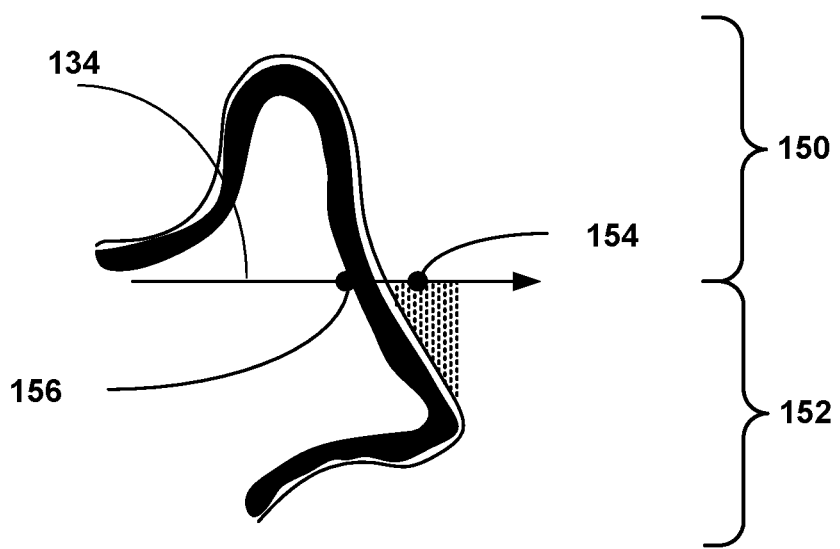

To determine the value of Cf2, processing circuitry 102 may determine a threshold point ($p_{th}$) laying on transverse axis 134 of the patient anatomy (e.g., pathological scapula). The point $p_{th}$ represents a threshold of the glenoid medialization that should be crossed by an instance of the intermediate shape model used to determine the pre-morbid characterizations. FIGS. 15A and 15B illustrate example ways in which to determine $p_{th}$. For example, processing circuitry 102 may divide image data from scans 108 of the glenoid into four quarters of interest (e.g., superior, posterior, inferior, and anterior).

FIGS. 15A and 15B are conceptual diagrams illustrating portions of a glenoid for determining parameters of a cost function used to determine a pre-morbid shape of anatomy of a patient. As described in more detail, with the illustrated portions of the glenoid in FIGS. 15A and 15B, processing circuitry 102 may determine a value of $p_{th}$. Processing circuitry 102 may also determine medialization values for each of the estimated shape models (e.g., generated from shape model 106 using values for bi and based on the eigenvalues and eigenvectors as described above). Based on the value of $p_{th}$ and the medialization values, processing circuitry 102 may determine a sub-cost value for Cf2.

FIG. 15A illustrates transverse axis 134 (e.g., as described above) that divides a glenoid surface into anterior side 142 and posterior side 144. FIG. 15B illustrates transverse axis 134 that divides a glenoid surface into superior side 150 and inferior side 152. For instance, referring back to FIG. 6, processing circuitry 102 determined transverse axis 134. Then, processing circuitry 102 may determine anterior side 142, posterior side 144, superior side 150, and inferior side 152 based on axial or sagittal cuts through scapula 118. The result may be the example illustrated in FIGS. 15A and 15B.

Processing circuitry 102 may project points on the glenoid surface for each of the portions (e.g., anterior and posterior sides of FIG. 15A and superior and inferior sides of FIG. 15B) to transverse axis 134 and determine a center of mass of the projected points of each portion. Point projection onto a line is the closest point on that line. The line and the vector defined by the point and its projection are perpendicular. This can be calculated by choosing a random point on the line which forms a hypotenuse with the point to be projected. Using trigonometry, the projection is the hypotenuse length multiplied by the cosine of the angle defined by the hypotenuse and the line. The center of mass is the mean point of the projected points on that line and can also be considered as the barycenter.

For example, point 146 in FIG. 15A is an example of the center of mass of projected points for anterior side 142. Point 148 in FIG. 15A is an example of the center of mass of projected points for posterior side 144. Point 154 in FIG. 15B is an example of the center of mass of projected points for superior side 150. Point 156 in FIG. 15B is an example of the center of mass of projected points for inferior side 152.

In one or more examples, processing circuitry 102 may determine a most lateral barycenter point (e.g., the point that is furthest away from the center of the patient's body) from points 146, 148, 154, and 156. Processing circuitry 102 may set the most lateral barycenter point as the threshold point $p_{th}$. Processing circuitry 102 may also determine the most lateral quarter as $Q_{th}$. In some examples, the most lateral barycenter point need not necessarily be in the most lateral quarter. For example, assume that the point 156 is the most lateral barycenter point (e.g., threshold point $p_{th}$). In this example, the most lateral quarter ($Q_{th}$) may be inferior side 152 if the most lateral barycenter point were in the most lateral quarter. However, it is possible that the most lateral barycenter point is not in the most lateral quarter.

Processing circuitry 102 may determine a corresponding quarter in the instance of the estimated shape models with the $Q_{th}$ quarter (e.g., most lateral quarter). Processing circuitry 102 may project the points of the quarter of the instance of the estimated shape models to transverse axis 134. For example, for each of the estimated shape models, processing circuitry 102 may determine points like points 146, 148, 154, and 156 for each of the estimated shape models. However, because of the different medialization of the estimated shape models (e.g., due to the different values of bi used to generate the estimated shape models), the respective projected points may be at different locations on the transverse axis 134.

For example, processing circuitry 102 may determine an anchor point on transverse axis 134. This anchor point is in the same location on transverse axis 134 for each of the estimated shape models. Processing circuitry 102 may determine distances of the projected points to the anchor point. In some examples, $p_{th}$ may be the anchor point.

Processing circuitry 102 may determine the distance of the projected points to $p_{th}$. Processing circuitry 102 may determine an average of the distances of the projected points as a value equal to $d_{med}$.

If the value of $d_{med}$ is zero or positive, it means that the instance of the estimated shape model is more medial than the current patient anatomy (e.g., glenoid and scapula), and therefore not a good predictor for the pre-morbid characteristics of the patient anatomy. If the value of $d_{med}$ is negative, it means that the instance of the estimated shape model is less medial than the current patient anatomy, and therefore may be a possible predictor for the pre-morbid characteristics of the patient anatomy.

In some examples, processing circuitry 102 may set Cf2 equal to a value based on $d_{med}$ (e.g., Cf2 is a function of dined). For example, the function used to calculate Cf2 based on $d_{med}$ may be an increasing function for values of $d_{med}$ greater than zero and a decreasing function for values of $d_{med}$ less than zero. As one example, if $d_{med}$ is greater than or equal to 0, processing circuitry 102 may set Cf2 equal to $d_{med}$ and set Cf2 equal to 0 if $d_{med}$ is less than zero. In this way, if the instance of the estimated shape models is more medial than the current patient anatomy, the value of Cf2 is a positive number, and the overall cost value of the cost function will increase. Again, the cost function (Cf) is equal to Cf1 plus Cf2 plus Cf3 (and possibly updated with weights w1, w2, and w3), and if Cf2 is a positive number, the value of Cf will increase as compared to if the value of Cf2 is zero. Because processing circuitry 102 is determining cost value that satisfies a threshold (e.g., minimizing the cost function), having a positive value of Cf2 causes processing circuitry 102 to not use instances of the estimated shape models that are more medial than the current patient anatomy for determining the pre-morbid characteristics.

In some examples, the cost function value (Cf) may be based only on Cf1 and Cf2. For instance, for the ER loop, processing circuitry 102 may determine which estimated shape model results in minimizing Cf. However, it may be possible that in such cases that the estimated shape model is one with high variation (e.g., has a lower probability of representing pre-morbid characteristics in the general population). Accordingly, in some examples, for the ER loop, processing circuitry 102 may determine a parameter weighting value (e.g., Cf3). The parameter weighting value weights more likely estimated shape models as having a higher probability of being a representation of the pre-morbid anatomy and weights less like estimated shape models as having a lower probability of being a representation of the pre-morbid anatomy.

For example, in some examples, processing circuitry 102 may also determine a sub-cost function value, Cf3, that is used to penalize against more complex solutions within an increasing variance in the data errors. For instance, processing circuitry 102 may determine a gradient smoothing term using eigenvalues to penalize the participating modes of variation according to the following equation.

$$Cf3 = \sum_i^N \frac{\sum_j^i \lambda_j}{\sum_j^N \lambda j} \times b_i^2$$

In the above equation, N is the number of modes used to build an instance of the estimated shape model. Cf3 may not be necessary in all examples. For example, in the equation for Cf3, if an instance of the estimated shape model has many modes, then there will be a larger number of values to sum together, as compared to if the instance of the estimated shape model had fewer modes. Therefore, the result of the sum (e.g., value of Cf3) will be greater for those estimated shape models having larger modes than those estimated shape models having fewer modes. Accordingly, a larger value of Cf3 will cause the cost function value, Cf, to be bigger than a smaller value of Cf3. Because processing circuitry 102 may be minimizing the value of Cf, estimated shape models having a larger value of Cf3 are less likely to be determined as the pre-morbid shape of the patient anatomy as compared to estimated shape models having a smaller value of Cf3.

In general, Cf3 is composed of two terms: a coarse or hard term and a fine or smooth one. Eigenvalues are the diagonal positive values of the decomposition matrix. Their order reflects the occurrence of the corresponding eigenvectors into the database. Means that first eigenvalues represent the most "important" or frequent variation in the database, while the last eigenvalues represent the least frequent ones (usually representing noise). In the coarse term of Cf3, processing circuitry 102 may drop those eigenvectors that participate to the least important K % of the database variance (i.e. bi=0 if lambda(i)>q where $v_i$ for i<=q represents (100−K) % of the database variance). In the fine term of Cf3, processing circuitry 102 may gradually disadvantage higher eigenvectors. As a result the algorithm avoids complex or noisy solutions. In general, the terminology "smooth" is used to indicate addition of aa regularization term to an optimization method.

Processing circuitry 102 may determine the estimated shape model for which w1*Cf1+w2*Cf2+w3*Cf3 is less than a threshold (e.g., minimized). This estimated shape model is a first order shape model for the first iteration through the global loop.

For example, for the first iteration through the global loop, for the ER loop, assume processing circuitry 102 determines the following estimated shape models based on shape model 106 and different values of bi. For example, a first estimated shape model may be s11, where s11 is equal to s'+$\Sigma_i$b11$_i$ $\sqrt{\lambda_i} \times v_i$, where s' is shape model 106, λ is the eigenvalues used to determine shape model 106, and $v_i$ is the eigenvectors used to determine shape model 106. In this example, b11$_i$ is a first weighting parameter. Processing circuitry 102 may determine a second estimated shape model (e.g., s12), where s12 is equal to s'+$\Sigma_i$b12$_i\sqrt{\lambda_i} \times v_i$, where b12$_i$ is a second weighting parameter. In this manner, processing circuitry 102 may determine a plurality of estimated shape models (e.g., s11, s12, s13, and so forth).

For each of the estimated shape model, processing circuitry 102 may determine a value of Cf1, Cf2, and Cf3. Again, not all of Cf1, Cf2, and Cf3 are needed. For example, processing circuitry 102 may determine s11_Cf1 based on estimated shape model s11 and the first order shape generated by the ICP loop. Processing circuitry 102 may determine s12_Cf1 based on estimated shape model s12 and the first order shape generated by the ICP loop, and so forth. Processing circuitry 102 may determine s11_Cf2, s12_Cf3, and so forth as described above for the example techniques to determine Cf2. Similarly, processing circuitry 102 may determine s11_Cf3, s12_Cf3, and so forth as described above for the example techniques to determine Cf3.

Processing circuitry 102 may determine s11_Cf as: w1*s11_Cf1+w2*s11_Cf2+w3*s11_Cf3, determine s12_Cf as: w1*s12_Cf1+w2*s12_Cf2+w3*s13_Cf3, and so forth. The weights applied to the Cf1, Cf2, and Cf3 may be different for each of s11, s12, s13, and so forth, or the weights may be the same. Processing circuitry 102 may determine which one of s11_Cf, s12_Cf, s13_Cf, and so forth is the minimum (or possibly less than a threshold). Assume that s12_Cf is the minimum. In this example, processing circuitry 102 may determine estimated shape model s12 as the result of the ER loop, which for the first iteration of the global loop is the first order shape model.

This may conclude the first iteration of the global loop. For example, in the first iteration of the global loop, the ICP loop generated a first order shape and the ER loop generated a first order shape model. Then, for the second iteration of the global loop, the input to the ICP loop is the first order shape model generated from the previous ER loop and the first order shape generated from the previous ICP loop. In the ICP loop for the second iteration of the global loop, processing circuitry 102, based on the first order shape model and the first order shape, generates a second order shape. The second order shape is an input to the ER loop in the second iteration of the global loop. Also, in the ER loop, in the second iteration of the global loop, processing circuitry 102 may determine estimated shape models (e.g., s21, s22, s23, and so forth) based on shape model 106 and/or based on the first order shape model (e.g., s12 in this example). The output of the ER loop may be a second order shape model, and this may conclude the second iteration of the global loop.

This process repeats until processing circuitry 102 determines an instance of the estimated shape model that minimizes the Cf value. For instance, assume that after the first iteration of the global loop, processing circuitry 102 outputted estimated shape model s12 having cost value of s12_Cf. After the second iteration of the global loop, processing circuitry 102 outputted estimated shape model s23 having cost value of s23_Cf. After the third iteration of the global loop, processing circuitry 102 outputted estimated shape model s36 having cost value of s36_Cf. In this example, processing circuitry 102 may determine which one of s12_Cf, s23_Cf, or s36_Cf is the minimum value, and determine the estimated shape associated with the minimum Cf value as the pre-morbid anatomy of the patient. For example, assume that s23_Cf was the minimum. In this example, processing circuitry 102 may determine that estimated shape model s23 is represents the pre-morbid characteristics of the patient.

In the above examples, processing circuitry 102 may loop through the global loop until the value of Cf is minimized. However, in some examples, processing circuitry 102 may be configured to loop through the global loop for a set number of iterations. Processing circuitry 102 may then determine which one of the estimated shape models resulted in the minimum value of Cf. In some examples, processing circuitry 102 may loop through the global loop until the value of Cf is below a threshold.

As described above, processing circuitry 102 may determine a minimum for the cost function value, Cf Minimizing the value of Cf or determining the minimum Cf value from a plurality of Cf values are two example ways in which to satisfy the cost function. There may be other ways in which to satisfy the cost function. As one example, satisfying the cost function may mean that the cost value of the cost function is less than a threshold. Also, it may be possible to reconfigure the cost function so that satisfying the cost function means maximizing the cost function. For instance, one of the factors in the cost function may be a distance between points of the estimated shape models and corresponding points in the output from the ICP loop. In some examples, processing circuitry 102 may minimize the distance between the estimated shape models and output from ICP loop and may generate a number that is inversely correlated to distance (e.g., the closer the distance, the larger the number processing circuitry 102 generates). In this example, to satisfy the cost function, processing circuitry 102 may maximize the cost value that that is inversely correlated to the distance. Therefore, although the examples are described with respect to minimizing as part of the global loop and the ICP loop, in some examples, to satisfy (e.g., optimize) the cost function, processing circuitry 102 may maximize the value of Cf Such techniques are contemplated by this disclosure. For example, a cost value satisfying a threshold value means determining cost value is less than threshold value where cost value being less than threshold value is indicative of pre-morbid shape or greater than threshold value where cost value being greater than threshold value is indicative of pre-morbid shape.

Figure 16:
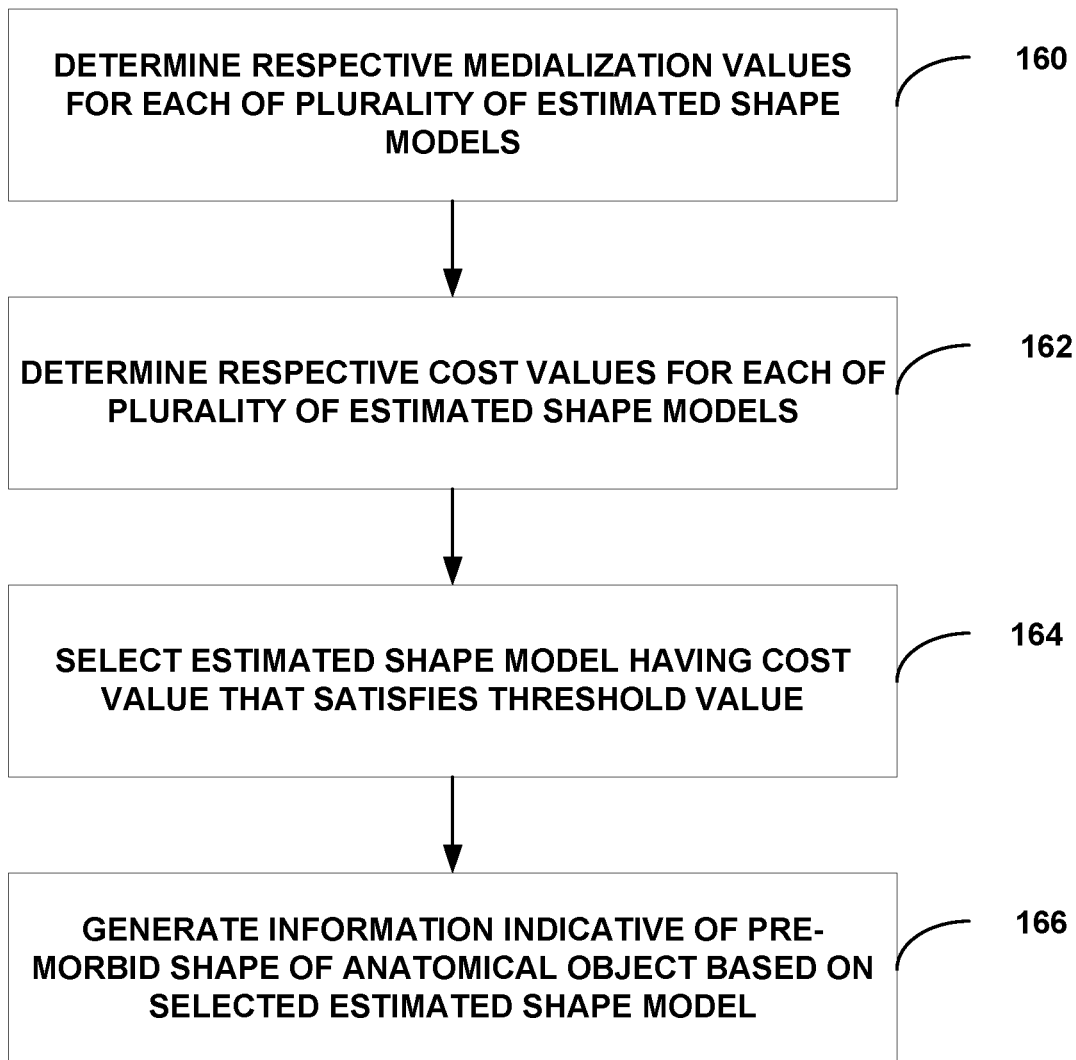
FIG. 16 is a flowchart illustrating an example method of operation in accordance with one or more example techniques described in this disclosure.

FIG. 16 is a flowchart illustrating an example method of operation in accordance with one or more example techniques described in this disclosure. For instance, FIG. 16 illustrates an example manner in which processing circuitry 102 may perform the ER loop. Memory 104 may store shape model 106, and information used to determine shape model 106 such as the eigenvalues and eigenvectors. In some examples, processing circuitry 102 may determine estimated shape models (e.g., by selecting different scaling factors (130 and store the estimated shape models in memory 104. In some examples, the estimated shape models may be pre-generated and stored in memory 104.

Processing circuitry 102 may determine respective medialization values (e.g., Cf2) for each of the plurality of estimated shape models (160). As described, the plurality of estimated shape models is generated from shape model 106. In some examples, the estimated shape models may be generated from the result of the ICP loop. Each of the medialization values is indicative of an amount by which each respective one of the estimated shape models is medialized relative to a current position of the anatomical object.

Processing circuitry 102 may determine respective cost values (Cf) for each of the plurality of estimated shape models based at least in part on the respective determined medialization values (Cf2) for each of the plurality of estimated shape models (162). In some examples, rather than just relying on Cf2, processing circuitry 102 may determine Cf1 and possibly Cf3. For example, processing circuitry 102 may determine a shape based on shape model 106 and an aligned shape generated from image data of the anatomical object. In this example, the shape determined based on shape model 106 and the aligned shape may be the result of the ICP loop. Processing circuitry 102 may determine respective distance and orientation difference values (Cf1) for each of the plurality of estimated shape models. Each of the respective distance and orientation difference values is indicative of a difference in distance and orientation between respective estimated shape models and the determined shape. Processing circuitry 102 may determine respective cost values for each of the plurality of estimated shape models based at least in part on the respective determined medialization values (Cf2) for each of the plurality of estimated shape models and the respective determined distance and orientation difference values (Cf1).

In some examples, processing circuitry 102 may determine respective weighting values (Cf3) based on a likelihood of each of the respective estimated shape models being representative of the pre-morbid shape of the anatomical object. In such examples, processing circuitry 102 may determine respective cost values (Cf) for each of the plurality of estimated shape models based at least in part on the respective determined medialization values (Cf2) for each of the plurality of estimated shape models and one or more of the respective determined distance and orientation difference values (Cf1) and the respective weighting values (Cf3).

To determining the respective weighting values (Cf3), processing circuitry 102 may be configured to perform $$\sum_i^N \frac{\sum_j^i \lambda_j}{\sum_j^N \lambda_j} \times b_i^2.$$

N equals a number of modes used to build respective plurality of estimated shape models, λ equals eigenvalues of the shape model, and b equals a scaling factor used to determine respective plurality of estimated shape models.

To determine respective distance and orientation difference values (Cf1) for each of the plurality of estimated shape models, processing circuitry 102 may be configured to determine respective distances between corresponding points on respective estimated shape models and the determined shape, determine respective angular differences between normal vectors for the corresponding points on respective estimated shape models and the determined shape, and determine respective distance and orientation difference values based on the determine respective distances and the determined respective angular differences.

To determine respective medialization values for each of the plurality of estimated shape models, processing circuitry 102 may be configured to divide image data of the anatomical object into a plurality of portions, project points from each of the plurality of portions to a transverse axis, determine a threshold point from one of the projected points, determine a most lateral portion from the plurality of portions, determine a portion in each of the plurality of estimated shape models that corresponds to the determined most lateral position, project points from the determined portion in each of the plurality of estimated shape models to the transverse axis, determining distances from the projected points to the threshold point, and determine respective medialization values for each of the plurality of estimated shape models based on the determined distances.

Processing circuitry 102 may be configured to select an estimated shape model from the plurality of estimated shape models having (e.g., associated with) a cost value of the respective cost values that satisfies a function for the cost value (e.g., less than threshold value), including the example where the cost value is minimized (164). In this example, the estimated shape model having the cost value less than a threshold value is the result of the ER loop. Processing circuitry 102 may generate information indicative of the pre-morbid shape of the anatomical object based on the selected estimated shape model (166). For example, the output of the ER loop may be an input into the next operations of the ICP loop, and the ER loop and ICP loop may repeat until the cost value satisfies a threshold (e.g., less than threshold including minimized).

Figure 17:
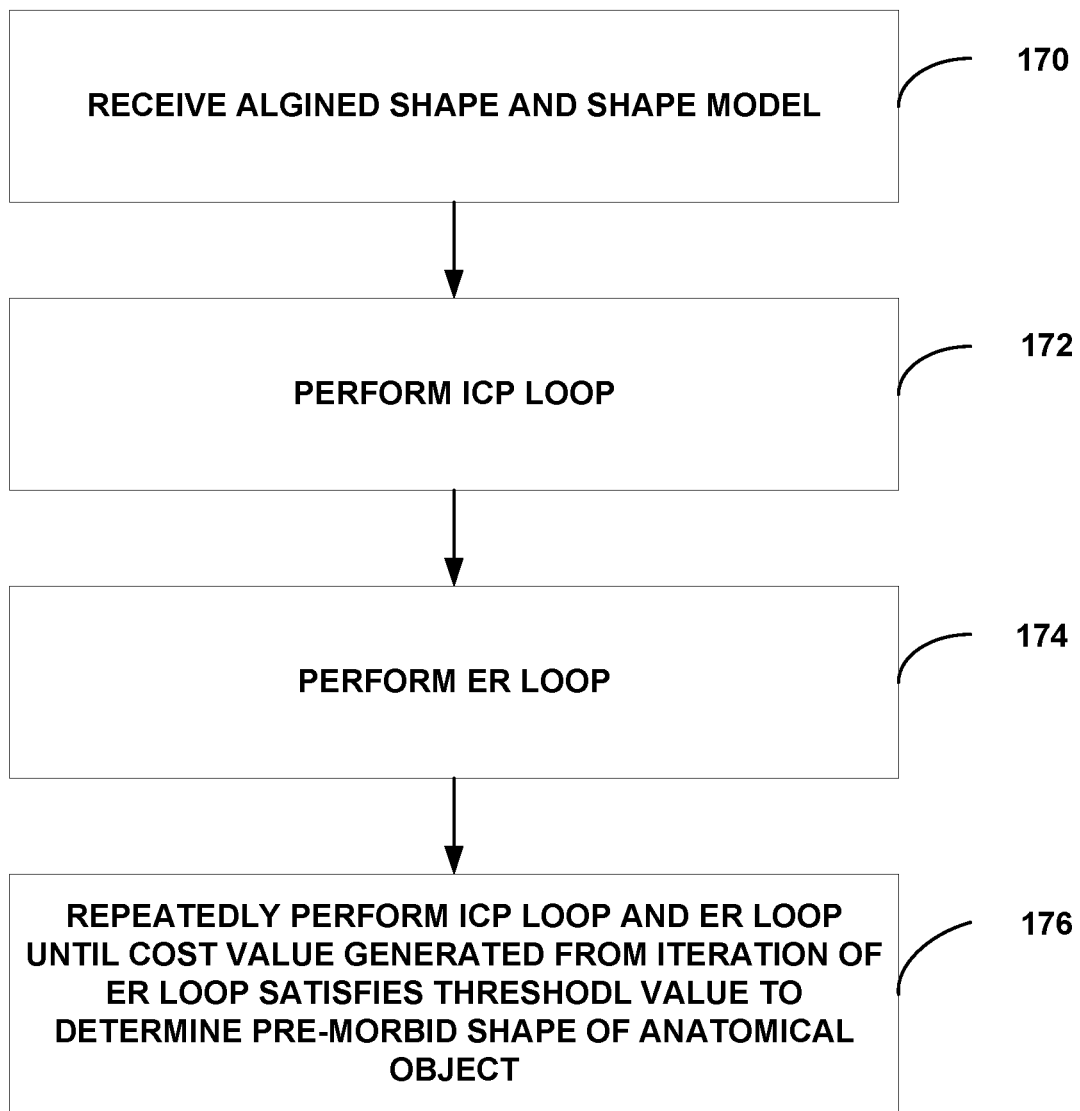
FIG. 17 is a flowchart illustrating an example method of operation in accordance with one or more example techniques described in this disclosure.

FIG. 17 is a flowchart illustrating an example method of operation in accordance with one or more example techniques described in this disclosure. For example, FIG. 17 illustrates an example of the global loop that includes the ICP loop and the ER loop. Processing circuitry 102 may receive an aligned shape and shape model 106 (170). Techniques to determine the aligned shape are described above and with FIG. 18.

Processing circuitry 102 perform the ICP loop (172). For example, to perform the ICP loop, processing circuitry 102 may be configured to modify the aligned shape, compare the modified aligned shaped to shape model 106, and determine a cost value based on the comparison. As also part of the ICP loop, processing circuitry 102 may repeat the modifying, comparing, and determining until the cost value satisfies a threshold value to generate a first order shape. The first order shape comprises the modified aligned shape associated with the cost value that satisfies the threshold value.

Processing circuitry 102 may perform the ER loop (174). To perform the ER loop, processing circuitry 102 may receive the first order shape and shape model 106. Processing circuitry 102 may determine respective cost values for each of a first set of plurality of estimated shape models based on the first order shape and respective plurality of estimated shape models. The plurality of estimated shape models may be generated based on the shape model 106. For example, processing circuitry 102 may determine value of Cf for each of the estimated shape models based on Cf1, Cf2, and/or Cf3 as described above. Processing circuitry 102 may determine a first estimated shape model of the plurality of estimated shape models associated with a cost value of the respective cost values that satisfies a first threshold value. The estimated shape model comprises a first order shape model.

The first order shape model from the ER loop may be fed back to the ICP loop and the ICP loop may utilize the first order shape model and the first order shape generated from the previous ICP loop to generate a second order shape. The second order shape is fed to the ER loop, and processing circuitry 102 utilizes the second order shape and the first order shape model and/or shape model 106 to generate a second order shape model that is fed back to the ICP loop, and this process repeats until the Cf value generated from the ER loop is below a threshold (e.g., minimized).

For example, processing circuitry 102 may repeatedly perform the ICP loop and the ER loop until a cost value generated from an iteration of the ER loop satisfies a second threshold value to determine the pre-morbid shape of the anatomical object (176). To repeatedly perform the ICP loop and the ER loop, processing circuitry 102 may be configured to receive, for the ICP loop, an order shape model generated by a previous ER loop and an order shape generated by a previous ICP loop, generate, by the ICP loop, a current order shape based on the order shape model and the order shape, receive, for the ER loop, the current order shape and at least one of shape model or the order shape model generated by the previous ER loop, generate a next set of plurality of estimated shape models based on at least one of the shape model or the order shape model generated by the previous ER loop, determine respective cost values for each of the second set of plurality of estimated shape models based on the order shape of the current order shape and respective second set of plurality of estimated shape models, and determine a current estimated shape model of the second set of plurality of estimated shape models associated with a cost value of the respective cost values that satisfies the first threshold value. The current estimated shape model is a current order shape model generated by the ER loop that is fed back to the ICP loop.

Figure 18:
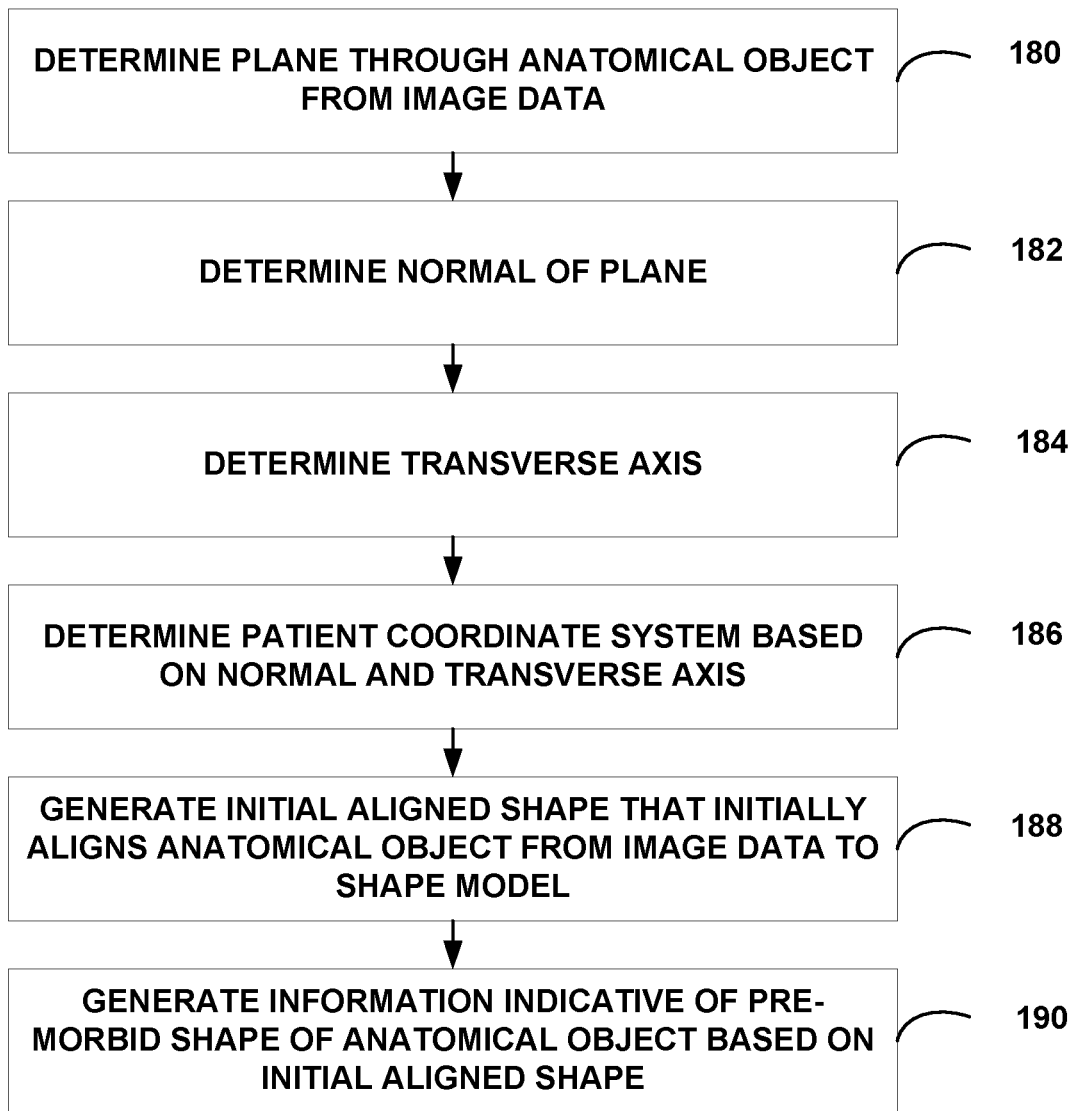
FIG. 18 is a flowchart illustrating an example method of operation in accordance with one or more example techniques described in this disclosure.

FIG. 18 is a flowchart illustrating an example method of operation in accordance with one or more example techniques described in this disclosure. For example, FIG. 18 illustrates an example manner in which to determine initial aligned shape 138 and aligned shape 140 based on a patient coordinate system.

Processing circuitry 102 may determine a plane 130 through the anatomical object from the image data. Plane 130 is a plane that is substantially through a middle of the anatomical object (180). Processing circuitry 102 may determine a normal (e.g., vector 132) of plane 130 (182). In addition, processing circuitry 102 may determine a transverse axis 134 through representations of sagittal cuts (e.g., as illustrated in FIGS. 7A, 7B, 9A, and 9B) through the anatomical object (184). Transverse axis 134 is orthogonal to the normal (e.g., vector 132).

Processing circuitry 102 may determine a patient coordinate system based on the normal (e.g., vector 132) and the transverse axis 134 (186). For example, processing circuitry 102 may determine the third axis, where vector 132 and transverse axis 134 form two of the three axes for defining 3D space, based on the vector 132 and transverse axis 134 as described above.

Processing circuitry 102 may generate an initial aligned shape that initially aligns the anatomical object from the image data to shape model 106 (188). For example, processing circuitry 102 may generate a transformation matrix and generate coordinates for anatomical objects that are in the coordinate system for shape model 106.

Processing circuitry 102 may generate information indicative of the pre-morbid shape of the anatomical object based on the initial aligned shape (190). For example, with initial aligned shape (e.g., initial aligned shape 138), processing circuitry 102 may iteratively adjust coordinates of the initial aligned shape to rotate the initial aligned shape until a distance between the initial aligned shape and the shape model satisfies a threshold value to generate an aligned shape 140. To generate information indicative of the pre-morbid shape of the anatomical object, processing circuitry 102 may generate information indicative of the pre-morbid shape based on the aligned shape 140. For example, aligned shape 140 may be an input into the global loop that includes the ICP loop and ER loop used to determine the pre-morbid shape.

The following describes one or more examples that may be used separately or in combination. The following examples should not be considered limiting.

Example 1

A method for determining a pre-morbid shape of an anatomical object of an orthopedic joint of a patient, the method comprising determining respective medialization values for each of a plurality of estimated shape models, wherein the plurality of estimated shape models is generated from a shape model, and wherein each of the medialization values is indicative of an amount by which each respective one of the estimated shape models is medialized relative to a current position of the anatomical object, determining respective cost values for each of the plurality of estimated shape models based at least in part on the respective determined medialization values for each of the plurality of estimated shape models, selecting an estimated shape model from the plurality of estimated shape models having a cost value of the respective cost values that satisfies a function for the cost value, and generating information indicative of the pre-morbid shape of the anatomical object based on the selected estimated shape model.

Example 2

The method of example 1, further comprising determining a shape based on the shape model and an aligned shape generated from image data of the anatomical object, and determining respective distance and orientation difference values for each of the plurality of estimated shape models, wherein each of the respective distance and orientation difference values is indicative of a difference in distance and orientation between respective estimated shape models and the determined shape, wherein determining respective cost values for each of the plurality of estimated shape models comprises determining respective cost values for each of the plurality of estimated shape models based at least in part on the respective determined medialization values for each of the plurality of estimated shape models and the respective determined distance and orientation difference values.

Example 3

The method of any of examples 1 and 2, further comprising determining respective weighting values based on a likelihood of each of the respective estimated shape models being representative of the pre-morbid shape of the anatomical object, wherein determining respective cost values for each of the plurality of estimated shape models comprises determining respective cost values for each of the plurality of estimated shape models based at least in part on the respective determined medialization values for each of the plurality of estimated shape models and one or more of the respective determined distance and orientation difference values and the respective weighting values.

Example 4

The method of example 3, wherein determining the respective weighting values comprises performing $$\sum_{i}^{N} \frac{\sum_{j}^{i} \lambda_{j}}{\sum_{j}^{N} \lambda j} \times b_{i}^{2},$$

wherein N equals a number of modes used to build respective plurality of estimated shape models, wherein λ equals eigenvalues of the shape model, and b equals a scaling factor used to determine respective plurality of estimated shape models.

Example 5

The method of any of examples 2-4, wherein determining respective distance and orientation difference values for each of the plurality of estimated shape models comprises determining respective distances between corresponding points on respective estimated shape models and the determined shape, determining respective angular differences between normal vectors for the corresponding points on respective estimated shape models and the determined shape, and determining respective distance and orientation difference values based on the determine respective distances and the determined respective angular differences.

Example 6

The method of any of examples 1-5, wherein determining respective medialization values for each of the plurality of estimated shape models comprises dividing image data of the anatomical object into a plurality of portions, projecting points from each of the plurality of portions to a transverse axis, determining a threshold point from one of the projected points, determining a most lateral portion from the plurality of portion, determining a portion in each of the plurality of estimated shape models that corresponds to the determined most lateral position, projecting points from the determined portion in each of the plurality of estimated shape models to the transverse axis, determining distances from the projected points to the threshold point, and determining respective medialization values for each of the plurality of estimated shape models based on the determined distances.

Example 7

A device for determining a pre-morbid shape of an anatomical object of an orthopedic joint of a patient, the device comprising a memory configured to store one or more of a shape model and a plurality of estimated shape model and processing circuitry configured to determine respective medialization values for each of the plurality of estimated shape models, wherein the plurality of estimated shape models is generated from the shape model, and wherein each of the medialization values is indicative of an amount by which each respective one of the estimated shape models is medialized relative to a current position of the anatomical object, determine respective cost values for each of the plurality of estimated shape models based at least in part on the respective determined medialization values for each of the plurality of estimated shape models, select an estimated shape model from the plurality of estimated shape models having a cost value of the respective cost values that satisfies a function for the cost value, and generate information indicative of the pre-morbid shape of the anatomical object based on the selected estimated shape model.

Example 8

The device of example 7, wherein the processing circuitry is further configured to determine a shape based on the shape model and an aligned shape generated from image data of the anatomical object, and determine respective distance and orientation difference values for each of the plurality of estimated shape models, wherein each of the respective distance and orientation difference values is indicative of a difference in distance and orientation between respective estimated shape models and the determined shape, wherein to determine respective cost values for each of the plurality of estimated shape models, the processing circuitry is configured to determine respective cost values for each of the plurality of estimated shape models based at least in part on the respective determined medialization values for each of the plurality of estimated shape models and the respective determined distance and orientation difference values.

Example 9

The device of any of examples 7 and 8, wherein the processing circuitry is configured to determine respective weighting values based on a likelihood of each of the respective estimated shape models being representative of the pre-morbid shape of the anatomical object, wherein to determine respective cost values for each of the plurality of estimated shape models, the processing circuitry is configured to determine respective cost values for each of the plurality of estimated shape models based at least in part on the respective determined medialization values for each of the plurality of estimated shape models and one or more of the respective determined distance and orientation difference values and the respective weighting values.

Example 10

The device of example 9, wherein to determine the respective weighting values, the processing circuitry is configured to perform $$\sum_{i}^{N} \frac{\sum_{j}^{i} \lambda_{j}}{\sum_{j}^{N} \lambda j} \times b_{i}^{2},$$

wherein N equals a number of modes used to build respective plurality of estimated shape models, wherein λ equals eigenvalues of the shape model, and b equals a scaling factor used to determine respective plurality of estimated shape models.

Example 11

The device of any of examples 8-10, wherein to determine respective distance and orientation difference values for each of the plurality of estimated shape models, the processing circuitry is configured to determine respective distances between corresponding points on respective estimated shape models and the determined shape, determine respective angular differences between normal vectors for the corresponding points on respective estimated shape models and the determined shape, and determine respective distance and orientation difference values based on the determine respective distances and the determined respective angular differences.

Example 12

The device of any of examples 7-11, wherein to determine respective medialization values for each of the plurality of estimated shape models, the processing circuitry is configured to divide image data of the anatomical object into a plurality of portions, project points from each of the plurality of portions to a transverse axis, determine a threshold point from one of the projected points, determine a most lateral portion from the plurality of portion, determine a portion in each of the plurality of estimated shape models that corresponds to the determined most lateral position, project points from the determined portion in each of the plurality of estimated shape models to the transverse axis, determine distances from the projected points to the threshold point, and determine respective medialization values for each of the plurality of estimated shape models based on the determined distances.

Example 13

A computer-readable storage medium storing instructions thereon that when executed cause one or more processors to determine respective medialization values for each of a plurality of estimated shape models, wherein the plurality of estimated shape models is generated from a shape model, and wherein each of the medialization values is indicative of an amount by which each respective one of the estimated shape models is medialized relative to a current position of the anatomical object, determine respective cost values for each of the plurality of estimated shape models based at least in part on the respective determined medialization values for each of the plurality of estimated shape models, select an estimated shape model from the plurality of estimated shape models having a cost value of the respective cost values that satisfies a function for the cost value, and generate information indicative of a pre-morbid shape of an anatomical object based on the selected estimated shape model.

Example 14

The computer-readable storage medium of example 13, further comprising instructions that cause the one or more processors to determine a shape based on the shape model and an aligned shape generated from image data of the anatomical object, and determine respective distance and orientation difference values for each of the plurality of estimated shape models, wherein each of the respective distance and orientation difference values is indicative of a difference in distance and orientation between respective estimated shape models and the determined shape, wherein the instructions that cause the one or more processors to determine respective cost values for each of the plurality of estimated shape models comprise instructions that cause the one or more processors to determine respective cost values for each of the plurality of estimated shape models based at least in part on the respective determined medialization values for each of the plurality of estimated shape models and the respective determined distance and orientation difference values.

Example 15

The computer-readable storage medium of any of examples 13 and 14, further comprising instructions that cause the one or more processors to determine respective weighting values based on a likelihood of each of the respective estimated shape models being representative of the pre-morbid shape of the anatomical object, wherein the instructions that cause the one or more processors to determine respective cost values for each of the plurality of estimated shape models comprise instructions that cause the one or more processors to determine respective cost values for each of the plurality of estimated shape models based at least in part on the respective determined medialization values for each of the plurality of estimated shape models and one or more of the respective determined distance and orientation difference values and the respective weighting values.

Example 16

The computer-readable storage medium of example 15, wherein the instructions that cause the one or more processors to determine the respective weighting values comprise instructions that cause the one or more processors to perform $$\sum_{i}^{N} \frac{\sum_{j}^{i} \lambda_j}{\sum_{j}^{N} \lambda j} \times b_i^2,$$

wherein N equals a number of modes used to build respective plurality of estimated shape models, wherein λ equals eigenvalues of the shape model, and b equals a scaling factor used to determine respective plurality of estimated shape models.

Example 17

The computer-readable storage medium of any of examples 14-16, wherein the instructions that cause the one or more processors to determine respective distance and orientation difference values for each of the plurality of estimated shape models comprise instructions that cause the one or more processors to determine respective distances between corresponding points on respective estimated shape models and the determined shape, determine respective angular differences between normal vectors for the corresponding points on respective estimated shape models and the determined shape, and determine respective distance and orientation difference values based on the determine respective distances and the determined respective angular differences.

Example 18

The computer-readable storage medium of any of examples 13-17, wherein the instructions that cause the one or more processors to determine respective medialization values for each of the plurality of estimated shape models comprise instructions that cause the one or more processors to divide image data of the anatomical object into a plurality of portions, project points from each of the plurality of portions to a transverse axis, determine a threshold point from one of the projected points, determine a most lateral portion from the plurality of portion, determine a portion in each of the plurality of estimated shape models that corresponds to the determined most lateral position, project points from the determined portion in each of the plurality of estimated shape models to the transverse axis, determine distances from the projected points to the threshold point, and determine respective medialization values for each of the plurality of estimated shape models based on the determined distances.

Example 19

A system for determining a pre-morbid shape of an anatomical object of an orthopedic joint of a patient, the system comprising means for determining respective medialization values for each of a plurality of estimated shape models, wherein the plurality of estimated shape models is generated from a shape model, and wherein each of the medialization values is indicative of an amount by which each respective one of the estimated shape models is medialized relative to a current position of the anatomical object, means for determining respective cost values for each of the plurality of estimated shape models based at least in part on the respective determined medialization values for each of the plurality of estimated shape models, means for selecting an estimated shape model from the plurality of estimated shape models having a cost value of the respective cost values that satisfies a function for the cost value, and means for generating information indicative of the pre-morbid shape of the anatomical object based on the selected estimated shape model.

Example 20

The system of example 19, further comprising means for determining a shape based on one of the shape model and an aligned shape generated from image data of the anatomical object, and means for determining respective distance and orientation difference values for each of the plurality of estimated shape models, wherein each of the respective distance and orientation difference values is indicative of a difference in distance and orientation between respective estimated shape models and the determined shape, wherein the means for determining respective cost values for each of the plurality of estimated shape models comprises means for determining respective cost values for each of the plurality of estimated shape models based at least in part on the respective determined medialization values for each of the plurality of estimated shape models and the respective determined distance and orientation difference values.

Example 21

The system of any of examples 19 and 20, further comprising means for determining respective weighting values based on a likelihood of each of the respective estimated shape models being representative of the pre-morbid shape of the anatomical object, wherein the means for determining respective cost values for each of the plurality of estimated shape models comprises means for determining respective cost values for each of the plurality of estimated shape models based at least in part on the respective determined medialization values for each of the plurality of estimated shape models and one or more of the respective determined distance and orientation difference values and the respective weighting values.

Example 22

The system of example 21, wherein the means for determining the respective weighting values comprises means for performing $$\sum_{i}^{N} \frac{\sum_{j}^{i} \lambda_j}{\sum_{j}^{N} \lambda_j} \times b_i^2,$$

wherein N equals a number of modes used to build respective plurality of estimated shape models, wherein λ equals eigenvalues of the shape model, and b equals a scaling factor used to determine respective plurality of estimated shape models.

Example 23

The system of any of examples 20-22, wherein the means for determining respective distance and orientation difference values for each of the plurality of estimated shape models comprises means for determining respective distances between corresponding points on respective estimated shape models and the determined shape, means for determining respective angular differences between normal vectors for the corresponding points on respective estimated shape models and the determined shape, and means for determining respective distance and orientation difference values based on the determine respective distances and the determined respective angular differences.

Example 24

The system of any of examples 19-23, wherein the means for determining respective medialization values for each of the plurality of estimated shape models comprises means for dividing image data of the anatomical object into a plurality of portions, means for projecting points from each of the plurality of portions to a transverse axis, means for determining a threshold point from one of the projected points, means for determining a most lateral portion from the plurality of portion, means for determining a portion in each of the plurality of estimated shape models that corresponds to the determined most lateral position, means for projecting points from the determined portion in each of the plurality of estimated shape models to the transverse axis, means for determining distances from the projected points to the threshold point, and means for determining respective medialization values for each of the plurality of estimated shape models based on the determined distances.

Example 25

A method for determining a pre-morbid shape of an anatomical object of an orthopedic joint of a patient, the method comprising receiving an aligned shape and a shape model, performing an iterative closest point (ICP) loop, wherein performing the ICP loop comprises modifying the aligned shape, comparing the modified aligned shape to the shape model, determining a cost value based on the comparison, and repeating the modifying, comparing, and determining until the cost value satisfies a threshold value to generate a first order shape, wherein the first order shape comprises the modified aligned shape associated with the cost value that satisfies the threshold value, performing an elastic registration (ER) loop, wherein performing the ER loop comprises receiving the first order shape and the shape model, determining respective cost values for each of a first set of plurality of estimated shape models based on the first order shape and respective plurality of estimated shape models, wherein the plurality of estimated shape models is generated based on the shape model, and determining a first estimated shape model of the plurality of estimated shape models associated with a cost value of the respective cost values that satisfies a first threshold value, wherein the estimated shape model comprises a first order shape model, and repeatedly performing the ICP loop and the ER loop until a cost value generated from an iteration of the ER loop satisfies a second threshold value to determine the pre-morbid shape of the anatomical object, wherein repeatedly performing the ICP loop and the ER loop comprises receiving, for the ICP loop, an order shape model generated by a previous ER loop and an order shape generated by a previous ICP loop, generating, by the ICP loop, a current order shape based on the order shape model and the order shape, receiving, for the ER loop, the current order shape and at least one of shape model or the order shape model generated by the previous ER loop, generating a next set of plurality of estimated shape models based on at least one of the shape model or the order shape model generated by the previous ER loop, determining respective cost values for each of the second set of plurality of estimated shape models based on the order shape of the current order shape and respective second set of plurality of estimated shape models, and determining a current estimated shape model of the second set of plurality of estimated shape models associated with a cost value of the respective cost values that satisfies the first threshold value, wherein the current estimated shape model comprises a current order shape model generated by the ER loop.

Example 26

The method of example 25, wherein determining respective cost values for each of the second set of plurality of estimated shape models comprises determining respective distance and orientation difference values for each of the second set of plurality of estimated shape models, wherein each of the respective distance and orientation difference values is indicative of a difference in distance and orientation between respective second set of estimated shape models and the current order shape, determining respective medialization values for each of the second set of plurality of estimated shape models, wherein each of the medialization values is indicative of an amount by which each respective one of the second set of plurality of estimated shape models is medialized relative to a current position of the anatomical object, and determining respective cost values based on the respective distance and orientation difference values and the respective medialization values.

Example 27

The method of example 26, further comprising determining a respective weighting values based on a likelihood of each of the respective second set of the plurality of estimated shape models being representative of the pre-morbid shape of the anatomical object, wherein determining respective cost values for each of the second set of the plurality of estimated shape models comprises determining respective cost values for each of the second set of the plurality of estimated shape models based at least in part on the respective distance and orientation difference values, the respective medialization values, and the respective weighting values.

Example 28

The method of any of examples 25-27, further comprising any combination of examples 1-6.

Example 29

A device for determining a pre-morbid shape of an anatomical object of an orthopedic joint of a patient, the device comprising a memory configured to store a shape model and processing circuitry configured to receive an aligned shape and a shape model, perform an iterative closest point (ICP) loop, wherein to perform the ICP loop, the processing circuitry is configured to modify the aligned shape, compare the modified aligned shape to the shape model, determine a cost value based on the comparison, and repeat the modifying, comparing, and determining until the cost value satisfies a threshold value to generate a first order shape, wherein the first order shape comprises the modified aligned shape associated with the cost value that satisfies the threshold value, perform an elastic registration (ER) loop, wherein to perform the ER loop, the processing circuitry is configured to receive the first order shape and the shape model, determine respective cost values for each of a first set of plurality of estimated shape models based on the first order shape and respective plurality of estimated shape models, wherein the plurality of estimated shape models is generated based on the shape model, and determine a first estimated shape model of the plurality of estimated shape models associated with a cost value of the respective cost values that satisfies a first threshold value, wherein the estimated shape model comprises a first order shape model, and repeatedly perform the ICP loop and the ER loop until a cost value generated from an iteration of the ER loop satisfies a second threshold value to determine the pre-morbid shape of the anatomical object, wherein to repeatedly perform the ICP loop and the ER loop, the processing circuitry is configured to receive, for the ICP loop, an order shape model generated by a previous ER loop and an order shape generated by a previous ICP loop, generate, by the ICP loop, a current order shape based on the order shape model and the order shape, receive, for the ER loop, the current order shape and at least one of shape model or the order shape model generated by the previous ER loop, generate a next set of plurality of estimated shape models based on at least one of the shape model or the order shape model generated by the previous ER loop, determine respective cost values for each of the second set of plurality of estimated shape models based on the order shape of the current order shape and respective second set of plurality of estimated shape models, and determine a current estimated shape model of the second set of plurality of estimated shape models associated with a cost value of the respective cost values that satisfies the first threshold value, wherein the current estimated shape model comprises a current order shape model generated by the ER loop.

Example 30

The device of example 29, wherein to determine respective cost values for each of the second set of plurality of estimated shape models, the processing circuitry is configured to determine respective distance and orientation difference values for each of the second set of plurality of estimated shape models, wherein each of the respective distance and orientation difference values is indicative of a difference in distance and orientation between respective second set of estimated shape models and the current order shape, determine respective medialization values for each of the second set of plurality of estimated shape models, wherein each of the medialization values is indicative of an amount by which each respective one of the second set of plurality of estimated shape models is medialized relative to a current position of the anatomical object, and determine respective cost values based on the respective distance and orientation difference values and the respective medialization values.

Example 31

The device of example 30, wherein the processing circuitry is configured to determine a respective weighting values based on a likelihood of each of the respective second set of the plurality of estimated shape models being representative of the pre-morbid shape of the anatomical object, wherein to determine respective cost values for each of the second set of the plurality of estimated shape models, the processing circuitry is configured to determine respective cost values for each of the second set of the plurality of estimated shape models based at least in part on the respective distance and orientation difference values, the respective medialization values, and the respective weighting values.

Example 32

The device of any of examples 29-31, wherein the processing circuitry is configured to perform the features of any of examples 7-12.

Example 33

A computer-readable storage medium storing instructions thereon that when executed cause one or more processors to receive an aligned shape and a shape model, perform an iterative closest point (ICP) loop, wherein the instructions that cause the one or more processors to perform the ICP loop comprise instructions that cause the one or more processors to modify the aligned shape, compare the modified aligned shape to the shape model, determine a cost value based on the comparison, and repeat the modifying, comparing, and determining until the cost value satisfies a threshold value to generate a first order shape, wherein the first order shape comprises the modified aligned shape associated with the cost value that satisfies the threshold value, perform an elastic registration (ER) loop, wherein the instructions that cause the one or more processors to perform the ER loop comprise instructions that cause the one or more processors to receive the first order shape and the shape model, determine respective cost values for each of a first set of plurality of estimated shape models based on the first order shape and respective plurality of estimated shape models, wherein the plurality of estimated shape models is generated based on the shape model, and determine a first estimated shape model of the plurality of estimated shape models associated with a cost value of the respective cost values that satisfies a first threshold value, wherein the estimated shape model comprises a first order shape model, and repeatedly perform the ICP loop and the ER loop until a cost value generated from an iteration of the ER loop satisfies a second threshold value to determine a pre-morbid shape of an anatomical object, wherein the instructions that cause the one or more processors to repeatedly perform the ICP loop and the ER loop comprise instructions that cause the one or more processors to receive, for the ICP loop, an order shape model generated by a previous ER loop and an order shape generated by a previous ICP loop, generate, by the ICP loop, a current order shape based on the order shape model and the order shape, receive, for the ER loop, the current order shape and at least one of shape model or the order shape model generated by the previous ER loop, generate a next set of plurality of estimated shape models based on at least one of the shape model or the order shape model generated by the previous ER loop, determine respective cost values for each of the second set of plurality of estimated shape models based on the order shape of the current order shape and respective second set of plurality of estimated shape models, and determine a current estimated shape model of the second set of plurality of estimated shape models associated with a cost value of the respective cost values that satisfies the first threshold value, wherein the current estimated shape model comprises a current order shape model generated by the ER loop.

Example 34

The computer-readable storage medium of example 33, wherein the instructions that cause the one or more processors to determine respective cost values for each of the second set of plurality of estimated shape models comprise instructions that cause the one or more processors to determine respective distance and orientation difference values for each of the second set of plurality of estimated shape models, wherein each of the respective distance and orientation difference values is indicative of a difference in distance and orientation between respective second set of estimated shape models and the current order shape, determine respective medialization values for each of the second set of plurality of estimated shape models, wherein each of the medialization values is indicative of an amount by which each respective one of the second set of plurality of estimated shape models is medialized relative to a current position of the anatomical object, and determine respective cost values based on the respective distance and orientation difference values and the respective medialization values.

Example 35

The computer-readable storage medium of example 34, further comprising instructions that cause the one or more processors to determine a respective weighting values based on a likelihood of each of the respective second set of the plurality of estimated shape models being representative of the pre-morbid shape of the anatomical object, wherein the instructions that cause the one or more processors to determine respective cost values for each of the second set of the plurality of estimated shape models comprise instructions that cause the one or more processors to determine respective cost values for each of the second set of the plurality of estimated shape models based at least in part on the respective distance and orientation difference values, the respective medialization values, and the respective weighting values.

Example 36

The computer-readable storage medium of any of examples 33-35, further comprising instructions that cause the one or more processors to perform the features of any combination of examples 13-18.

Example 37

A system for determining a pre-morbid shape of an anatomical object of an orthopedic joint of a patient, the system comprising means for receiving an aligned shape and a shape model, means for performing an iterative closest point (ICP) loop, wherein the means for performing the ICP loop comprises means for modifying the aligned shape, means for comparing the modified aligned shape to the shape model, means for determining a cost value based on comparison, and means for repeating the modifying, comparing, and determining until the cost value satisfies a threshold value to generate a first order shape, wherein the first order shape comprises the modified aligned shape associated with the cost value that satisfies the threshold value, means for performing an elastic registration (ER) loop, wherein the means for performing the ER loop comprises means for receiving the first order shape and the shape model, means for determining respective cost values for each of a first set of plurality of estimated shape models based on the first order shape and respective plurality of estimated shape models, wherein the plurality of estimated shape models is generated based on the shape model, and means for determining a first estimated shape model of the plurality of estimated shape models associated with a cost value of the respective cost values that satisfies a first threshold value, wherein the estimated shape model comprises a first order shape model, and means for repeatedly performing the ICP loop and the ER loop until a cost value generated from an iteration of the ER loop satisfies a second threshold value to determine the pre-morbid shape of the anatomical object, wherein the means for repeatedly performing the ICP loop and the ER loop comprises means for receiving, for the ICP loop, an order shape model generated by a previous ER loop and an order shape generated by a previous ICP loop, means for generating, by the ICP loop, a current order shape based on the order shape model and the order shape, means for receiving, for the ER loop, the current order shape and at least one of shape model or the order shape model generated by the previous ER loop, means for generating a next set of plurality of estimated shape models based on at least one of the shape model or the order shape model generated by the previous ER loop, means for determining respective cost values for each of the second set of plurality of estimated shape models based on the order shape of the current order shape and respective second set of plurality of estimated shape models, and means for determining a current estimated shape model of the second set of plurality of estimated shape models associated with a cost value of the respective cost values that satisfies the first threshold value, wherein the current estimated shape model comprises a current order shape model generated by the ER loop.

Example 38

The system of example 37, wherein the means for determining respective cost values for each of the second set of plurality of estimated shape models comprises means for determining respective distance and orientation difference values for each of the second set of plurality of estimated shape models, wherein each of the respective distance and orientation difference values is indicative of a difference in distance and orientation between respective second set of estimated shape models and the current order shape, means for determining respective medialization values for each of the second set of plurality of estimated shape models, wherein each of the medialization values is indicative of an amount by which each respective one of the second set of plurality of estimated shape models is medialized relative to a current position of the anatomical object, and means for determining respective cost values based on the respective distance and orientation difference values and the respective medialization values.

Example 39

The system of example 38, further comprising means for determining a respective weighting values based on a likelihood of each of the respective second set of the plurality of estimated shape models being representative of the pre-morbid shape of the anatomical object, wherein the means for determining respective cost values for each of the second set of the plurality of estimated shape models comprises means for determining respective cost values for each of the second set of the plurality of estimated shape models based at least in part on the respective distance and orientation difference values, the respective medialization values, and the respective weighting values.

Example 40

The system of any of examples 37-39, further comprising means for performing any combination of examples 19-24.

Example 41

A method for determining a pre-morbid shape of an anatomical object of an orthopedic joint of a patient, the method comprising determining a plane through the anatomical object from the image data, wherein the plane is a plane that is substantially through a middle of the anatomical object, determining a normal of the plane, determining a transverse axis through representations of sagittal cuts through the anatomical object, wherein the transverse axis is orthogonal to the normal, determining a patient coordinate system based on the normal and the transverse axis, generating an initial aligned shape that initially aligns the anatomical object from the image data to a shape model, and generating information indicative of the pre-morbid shape of the anatomical object based on the initial aligned shape.

Example 42

The method of example 41, further comprising iteratively adjusting coordinates of the initial aligned shape to rotate the initial aligned shape until a distance between the initial aligned shape and the shape model satisfies a threshold value to generate an aligned shape, wherein generating information indicative of the pre-morbid shape of the anatomical object comprises generating information indicative of the pre-morbid shape based on the aligned shape.

Example 43

The method of any of examples 41 and 42, wherein generating information indicative of the pre-morbid shape comprises generating information indicative of the pre-morbid shape based on features of any of examples 1-6 and 25-28.

Example 44

A device for determining a pre-morbid shape of an anatomical object of an orthopedic joint of a patient, the device comprising memory configured to store image data and processing circuitry configured to determine a plane through the anatomical object from the image data, wherein the plane is a plane that is substantially through a middle of the anatomical object, determine a normal of the plane, determine a transverse axis through representations of sagittal cuts through the anatomical object, wherein the transverse axis is orthogonal to the normal, determine a patient coordinate system based on the normal and the transverse axis, generate an initial aligned shape that initially aligns the anatomical object from the image data to a shape model, and generate information indicative of the pre-morbid shape of the anatomical object based on the initial aligned shape.

Example 45

The device of example 44, wherein the processing circuitry is configured to iteratively adjust coordinates of the initial aligned shape to rotate the initial aligned shape until a distance between the initial aligned shape and the shape model satisfies a threshold value to generate an aligned shape, wherein to generate information indicative of the pre-morbid shape of the anatomical object, the processing circuitry is configured to generate information indicative of the pre-morbid shape based on the aligned shape.

Example 46

The device of any of examples 44 and 45, wherein to generate information indicative of the pre-morbid shape, the processing circuitry is configured to generate information indicative of the pre-morbid shape based on features of any of examples 7-12 and 29-32.

Example 47

A computer-readable storage medium storing instructions that when executed cause one or more processors to determine a plane through the anatomical object from the image data, wherein the plane is a plane that is substantially through a middle of the anatomical object, determine a normal of the plane, determine a transverse axis through representations of sagittal cuts through the anatomical object, wherein the transverse axis is orthogonal to the normal, determine a patient coordinate system based on the normal and the transverse axis, generate an initial aligned shape that initially aligns the anatomical object from the image data to a shape model, and generate information indicative of a pre-morbid shape of an anatomical object based on the initial aligned shape.

Example 48

The computer-readable storage medium of example 47, further comprising instructions that cause the one or more processors to iteratively adjust coordinates of the initial aligned shape to rotate the initial aligned shape until a distance between the initial aligned shape and the shape model satisfies a threshold value to generate an aligned shape, wherein the instructions that cause the one or more processors to generate information indicative of the pre-morbid shape of the anatomical object comprise instructions that cause the one or more processors to generate information indicative of the pre-morbid shape based on the aligned shape.

Example 49

The computer-readable storage medium of any of examples 47 and 48, wherein the instructions that cause the one or more processors to generate information indicative of the pre-morbid shape comprise instructions that cause the one or more processors to generate information indicative of the pre-morbid shape based on features of any of examples 13-18 and 33-36.

Example 50

A system for determining a pre-morbid shape of an anatomical object of an orthopedic joint of a patient, the system comprising means for determining a plane through the anatomical object from the image data, wherein the plane is a plane that is substantially through a middle of the anatomical object, means for determining a normal of the plane, means for determining a transverse axis through representations of sagittal cuts through the anatomical object, wherein the transverse axis is orthogonal to the normal, means for determining a patient coordinate system based on the normal and the transverse axis, means for generating an initial aligned shape that initially aligns the anatomical object from the image data to a shape model, and means for generating information indicative of the pre-morbid shape of the anatomical object based on the initial aligned shape.

Example 51

The system of example 50, further comprising means for iteratively adjusting coordinates of the initial aligned shape to rotate the initial aligned shape until a distance between the initial aligned shape and the shape model satisfies a threshold value to generate an aligned shape, wherein the means for generating information indicative of the pre-morbid shape of the anatomical object comprises means for generating information indicative of the pre-morbid shape based on the aligned shape.

Example 52

The system of any of examples 50 and 51, wherein the means for generating information indicative of the pre-morbid shape comprises means for generating information indicative of the pre-morbid shape based on features of any of examples 19-24 and 37-40.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

The invention claimed is:

1. A method for determining a pre-morbid shape of an anatomical object of an orthopedic joint of a patient, the method comprising:
   determining respective medialization values for each of a plurality of estimated shape models, wherein the plurality of estimated shape models is generated from a first shape model, and wherein each of the medialization values is indicative of an amount by which each respective one of the estimated shape models is medialized relative to a current position of the anatomical object;
   determining respective cost values for each of the plurality of estimated shape models based at least in part on the respective determined medialization values for each of the plurality of estimated shape models;
   selecting an estimated shape model from the plurality of estimated shape models having a cost value of the respective cost values that satisfies a function for the cost value; and
   generating information indicative of the pre-morbid shape of the anatomical object based on the selected estimated shape model.

2. The method of claim 1, further comprising:
   determining a shape based on the first shape model and an aligned shape generated from image data of the anatomical object; and
   determining respective distance and orientation difference values for each of the plurality of estimated shape models, wherein each of the respective distance and orientation difference values is indicative of a difference in distance and orientation between respective estimated shape models and the determined shape,
   wherein determining the respective cost values for each of the plurality of estimated shape models comprises determining the respective cost values for each of the plurality of estimated shape models based at least in part on the respective determined medialization values for each of the plurality of estimated shape models and the respective determined distance and orientation difference values.

3. The method of claim 2, wherein determining the respective distance and orientation difference values for each of the plurality of estimated shape models comprises:
   determining respective distances between corresponding points on respective estimated shape models and the determined shape;
   determining respective angular differences between normal vectors for the corresponding points on respective estimated shape models and the determined shape; and
   determining the respective distance and orientation difference values based on the determined respective distances and the determined respective angular differences.

4. The method of claim 1, further comprising:
   determining respective weighting values based on a likelihood of each of the respective estimated shape models being representative of the pre-morbid shape of the anatomical object,
   wherein determining the respective cost values for each of the plurality of estimated shape models comprises determining the respective cost values for each of the plurality of estimated shape models based at least in part on the respective determined medialization values for each of the plurality of estimated shape models and the respective weighting values.

5. The method of claim 4, wherein determining the respective weighting values comprises performing $$\sum_{i}^{N} \frac{\sum_{j}^{i} \lambda_j}{\sum_{j}^{N} \lambda j} \times b_i^2,$$

wherein N equals a number of modes used to build respective plurality of estimated shape models, wherein equals eigenvalues of the first shape model, and b equals a scaling factor used to determine respective plurality of estimated shape models.

6. The method of claim 1, wherein determining respective medialization values for each of the plurality of estimated shape models comprises:
dividing image data of the anatomical object into a plurality of portions;
projecting points from each of the plurality of portions to a transverse axis;
determining a threshold point from one of the projected points;
determining a most lateral portion from the plurality of portion;
determining a portion in each of the plurality of estimated shape models that corresponds to the determined most lateral position;
projecting points from the determined portion in each of the plurality of estimated shape models to the transverse axis;
determining distances from the projected points to the threshold point; and
determining the respective medialization values for each of the plurality of estimated shape models based on the determined distances.

7. The method of claim 1, wherein determining the respective medialization values for each of the plurality of estimated shape models comprises:
projecting points from the anatomical object to a transverse axis;
projecting respective points from each of the plurality of estimated shape models to the transverse axis; and
determining the respective medialization values for each of the plurality of estimated shape models based on the projected points from the anatomical object to the transverse axis and the respective projected points from each of the plurality of estimated shape models to the transverse axis.

8. A device for determining a pre-morbid shape of an anatomical object of an orthopedic joint of a patient, the device comprising:
a memory configured to store one or more of a first shape model and a plurality of estimated shape models; and
processing circuitry configured to:
determine respective medialization values for each of the plurality of estimated shape models, wherein the plurality of estimated shape models is generated from the first shape model, and wherein each of the medialization values is indicative of an amount by which each respective one of the estimated shape models is medialized relative to a current position of the anatomical object;
determine respective cost values for each of the plurality of estimated shape models based at least in part on the respective determined medialization values for each of the plurality of estimated shape models;
select an estimated shape model from the plurality of estimated shape models having a cost value of the respective cost values that satisfies a function for the cost value; and
generate information indicative of the pre-morbid shape of the anatomical object based on the selected estimated shape model.

9. The device of claim 8, wherein the processing circuitry is further configured to:
determine a shape based on the first shape model and an aligned shape generated from image data of the anatomical object; and
determine respective distance and orientation difference values for each of the plurality of estimated shape models, wherein each of the respective distance and orientation difference values is indicative of a difference in distance and orientation between respective estimated shape models and the determined shape,
wherein to determine the respective cost values for each of the plurality of estimated shape models, the processing circuitry is configured to determine the respective cost values for each of the plurality of estimated shape models based at least in part on the respective determined medialization values for each of the plurality of estimated shape models and the respective determined distance and orientation difference values.

10. The device of claim 9, wherein to determine the respective distance and orientation difference values for each of the plurality of estimated shape models, the processing circuitry is configured to:
determine respective distances between corresponding points on respective estimated shape models and the determined shape;
determine respective angular differences between normal vectors for the corresponding points on respective estimated shape models and the determined shape; and
determine the respective distance and orientation difference values based on the determined respective distances and the determined respective angular differences.

11. The device of claim 8, wherein the processing circuitry is configured to:
determine respective weighting values based on a likelihood of each of the respective estimated shape models being representative of the pre-morbid shape of the anatomical object,
wherein to determine the respective cost values for each of the plurality of estimated shape models, the processing circuitry is configured to determine the respective cost values for each of the plurality of estimated shape models based at least in part on the respective determined medialization values for each of the plurality of estimated shape models and the respective weighting values.

12. The device of claim 11, where to determine the respective weighting values, the processing circuitry is configured to perform $$\sum_{i}^{N} \frac{\sum_{j}^{i} \lambda_j}{\sum_{j}^{N} \lambda j} \times b_i^2,$$

wherein N equals a number of modes used to build respective plurality of estimated shape models, wherein λ equals eigenvalues of the first shape model, and b equals a scaling factor used to determine respective plurality of estimated shape models.

13. The device of claim 8, wherein to determine respective medialization values for each of the plurality of estimated shape models, the processing circuitry is configured to:
divide image data of the anatomical object into a plurality of portions;
project points from each of the plurality of portions to a transverse axis;
determine a threshold point from one of the projected points;
determine a most lateral portion from the plurality of portion;
determine a portion in each of the plurality of estimated shape models that corresponds to the determined most lateral position;
project points from the determined portion in each of the plurality of estimated shape models to the transverse axis;
determine distances from the projected points to the threshold point; and
determine the respective medialization values for each of the plurality of estimated shape models based on the determined distances.

14. The device of claim 8, wherein to determine the respective medialization values for each of the plurality of estimated shape models, the processing circuitry is configured to:
project points from the anatomical object to a transverse axis;
project respective points from each of the plurality of estimated shape models to the transverse axis; and
determine the respective medialization values for each of the plurality of estimated shape models based on the projected points from the anatomical object to the transverse axis and the respective projected points from each of the plurality of estimated shape models to the transverse axis.

15. A non-transitory computer-readable storage medium storing instructions thereon that when executed cause one or more processors to:
determine respective medialization values for each of a plurality of estimated shape models, wherein the plurality of estimated shape models is generated from a first shape model, and wherein each of the medialization values is indicative of an amount by which each respective one of the estimated shape models is medialized relative to a current position of an anatomical object;
determine respective cost values for each of the plurality of estimated shape models based at least in part on the respective determined medialization values for each of the plurality of estimated shape models;
select an estimated shape model from the plurality of estimated shape models having a cost value of the respective cost values that satisfies a function for the cost value; and
generate information indicative of a pre-morbid shape of the anatomical object based on the selected estimated shape model.

16. The computer-readable storage medium of claim 15, further comprising instructions that cause the one or more processors to:
determine a shape based on the first shape model and an aligned shape generated from image data of the anatomical object; and
determine respective distance and orientation difference values for each of the plurality of estimated shape models, wherein each of the respective distance and orientation difference values is indicative of a difference in distance and orientation between respective estimated shape models and the determined shape,
wherein the instructions that cause the one or more processors to determine the respective cost values for each of the plurality of estimated shape models comprise instructions that cause the one or more processors to determine the respective cost values for each of the plurality of estimated shape models based at least in part on the respective determined medialization values for each of the plurality of estimated shape models and the respective determined distance and orientation difference values.

17. The computer-readable storage medium of claim 16, wherein the instructions that cause the one or more processors to determine the respective distance and orientation difference values for each of the plurality of estimated shape models comprise instructions that cause the one or more processors to:
determine respective distances between corresponding points on respective estimated shape models and the determined shape;
determine respective angular differences between normal vectors for the corresponding points on respective estimated shape models and the determined shape; and
determine the respective distance and orientation difference values based on the determined respective distances and the determined respective angular differences.

18. The computer-readable storage medium of claim 15, further comprising instructions that cause the one or more processors to:
determine respective weighting values based on a likelihood of each of the respective estimated shape models being representative of the pre-morbid shape of the anatomical object,
wherein the instructions that cause the one or more processors to determine the respective cost values for each of the plurality of estimated shape models comprise instructions that cause the one or more processors to determine the respective cost values for each of the plurality of estimated shape models based at least in part on the respective determined medialization values for each of the plurality of estimated shape models and the respective weighting values.

19. The computer-readable storage medium of claim 18, wherein the instructions that cause the one or more processors to determine the respective weighting values comprise instructions that cause the one or more processors to perform $$\sum_i^N \frac{\sum_j^i \lambda_j}{\sum_j^N \lambda_j} \times b_i^2,$$

wherein N equals a number of modes used to build respective plurality of estimated shape models, wherein $\lambda$ equals eigenvalues of the first shape model, and b equals a scaling factor used to determine respective plurality of estimated shape models.

20. The computer-readable storage medium of claim 15, wherein the instructions that cause the one or more processors to determine respective medialization values for each of the plurality of estimated shape models comprise instructions that cause the one or more processors to:
- divide image data of the anatomical object into a plurality of portions;
- project points from each of the plurality of portions to a transverse axis;
- determine a threshold point from one of the projected points;
- determine a most lateral portion from the plurality of portion;
- determine a portion in each of the plurality of estimated shape models that corresponds to the determined most lateral position;
- project points from the determined portion in each of the plurality of estimated shape models to the transverse axis;
- determine distances from the projected points to the threshold point; and
- determine the respective medialization values for each of the plurality of estimated shape models based on the determined distances.

21. A system for determining a pre-morbid shape of an anatomical object of an orthopedic joint of a patient, the system comprising:
- means for determining respective medialization values for each of a plurality of estimated shape models, wherein the plurality of estimated shape models is generated from a first shape model, and wherein each of the medialization values is indicative of an amount by which each respective one of the estimated shape models is medialized relative to a current position of the anatomical object;
- means for determining respective cost values for each of the plurality of estimated shape models based at least in part on the respective determined medialization values for each of the plurality of estimated shape models;
- means for selecting an estimated shape model from the plurality of estimated shape models having a cost value of the respective cost values that satisfies a function for the cost value; and
- means for generating information indicative of the pre-morbid shape of the anatomical object based on the selected estimated shape model.

22. The system of claim 21, further comprising:
- means for determining a shape based on one of the first shape model and an aligned shape generated from image data of the anatomical object; and
- means for determining respective distance and orientation difference values for each of the plurality of estimated shape models, wherein each of the respective distance and orientation difference values is indicative of a difference in distance and orientation between respective estimated shape models and the determined shape,
- wherein the means for determining the respective cost values for each of the plurality of estimated shape models comprises means for determining the respective cost values for each of the plurality of estimated shape models based at least in part on the respective determined medialization values for each of the plurality of estimated shape models and the respective determined distance and orientation difference values.

23. The system of claim 22, wherein the means for determining the respective distance and orientation difference values for each of the plurality of estimated shape models comprises:
- means for determining respective distances between corresponding points on respective estimated shape models and the determined shape;
- means for determining respective angular differences between normal vectors for the corresponding points on respective estimated shape models and the determined shape; and
- means for determining the respective distance and orientation difference values based on the determined respective distances and the determined respective angular differences.

24. The system of claim 21, further comprising:
- means for determining respective weighting values based on a likelihood of each of the respective estimated shape models being representative of the pre-morbid shape of the anatomical object,
- wherein the means for determining the respective cost values for each of the plurality of estimated shape models comprises means for determining the respective cost values for each of the plurality of estimated shape models based at least in part on the respective determined medialization values for each of the plurality of estimated shape models and the respective weighting values.

25. The system of claim 24, wherein the means for determining the respective weighting values comprises means for performing $$\sum_i^N \frac{\sum_j^i \lambda_j}{\sum_j^N \lambda j} \times b_i^2,$$

wherein N equals a number of modes used to build respective plurality of estimated shape models, wherein λ equals eigenvalues of the first shape model, and b equals a scaling factor used to determine respective plurality of estimated shape models.

26. The system of claim 21, wherein the means for determining respective medialization values for each of the plurality of estimated shape models comprises:
- means for dividing image data of the anatomical object into a plurality of portions;
- means for projecting points from each of the plurality of portions to a transverse axis;
- means for determining a threshold point from one of the projected points;
- means for determining a most lateral portion from the plurality of portion;
- means for determining a portion in each of the plurality of estimated shape models that corresponds to the determined most lateral position;
- means for projecting points from the determined portion in each of the plurality of estimated shape models to the transverse axis;
- means for determining distances from the projected points to the threshold point; and
- means for determining the respective medialization values for each of the plurality of estimated shape models based on the determined distances.

* * * * *